US008962588B2

(12) United States Patent
Olson et al.

(10) Patent No.: US 8,962,588 B2
(45) Date of Patent: *Feb. 24, 2015

(54) MICRO-RNAS THAT CONTROL MYOSIN EXPRESSION AND MYOFIBER IDENTITY

(71) Applicant: The Board of Regents, The University of Texas System, Austin, TX (US)

(72) Inventors: Eric N. Olson, Dallas, TX (US); Eva van Rooij, Utrecht (NL)

(73) Assignee: The Board of Regents, The University of Texas System, Austin, TX (US)

( * ) Notice: Subject to any disclaimer, the term of this patent is extended or adjusted under 35 U.S.C. 154(b) by 147 days.

This patent is subject to a terminal disclaimer.

(21) Appl. No.: 13/796,884

(22) Filed: Mar. 12, 2013

(65) Prior Publication Data
US 2013/0245092 A1 Sep. 19, 2013

Related U.S. Application Data

(63) Continuation of application No. 12/671,436, filed as application No. PCT/US2008/071837 on Jul. 31, 2008, now Pat. No. 8,481,507.

(60) Provisional application No. 60/952,911, filed on Jul. 31, 2007, provisional application No. 60/980,113, filed on Oct. 15, 2007, provisional application No. 60/980,314, filed on Oct. 16, 2007.

(51) Int. Cl.
*C12N 15/11* (2006.01)
*C07H 21/02* (2006.01)
*C07H 21/04* (2006.01)

(52) U.S. Cl.
USPC ...................... 514/44 A; 536/24.5

(58) Field of Classification Search
None
See application file for complete search history.

(56) References Cited

U.S. PATENT DOCUMENTS

| | | | |
|---|---|---|---|
| 7,232,806 B2 | 6/2007 | Tuschl et al. |
| 2005/0059005 A1 | 3/2005 | Tuschl et al. |
| 2005/0261218 A1 | 11/2005 | Esau et al. |
| 2006/0019286 A1 | 1/2006 | Horvitz et al. |
| 2006/0185027 A1 | 8/2006 | Bartel et al. |
| 2007/0287179 A1 | 12/2007 | Tuschl et al. |
| 2007/0292878 A1 | 12/2007 | Raymond |
| 2008/0050744 A1 | 2/2008 | Brown et al. |
| 2008/0176766 A1 | 7/2008 | Brown et al. |
| 2008/0214437 A1 | 9/2008 | Mohapatra et al. |
| 2009/0137504 A1 | 5/2009 | Echwald et al. |
| 2009/0143326 A1 | 6/2009 | Obad et al. |
| 2009/0286969 A1 | 11/2009 | Esau et al. |
| 2009/0291906 A1 | 11/2009 | Esau et al. |
| 2009/0291907 A1 | 11/2009 | Esau et al. |
| 2009/0293148 A1 | 11/2009 | Ren et al. |
| 2009/0317369 A1 | 12/2009 | Hosoda et al. |
| 2009/0326049 A1 | 12/2009 | Aristarkhov et al. |
| 2010/0029003 A1 | 2/2010 | Bartel et al. |
| 2010/0280094 A1 | 11/2010 | Beuvink et al. |

FOREIGN PATENT DOCUMENTS

| | | |
|---|---|---|
| EP | 1777301 A2 | 4/2007 |
| EP | 1959012 A2 | 8/2008 |
| EP | 2113567 A1 | 11/2009 |
| JP | 2004-522411 | 7/2004 |
| JP | 2006-502693 | 1/2006 |
| JP | 2006-101790 | 4/2006 |
| WO | WO 02/10453 A2 | 2/2002 |
| WO | WO 03/065993 A2 | 8/2003 |
| WO | WO 2005/013901 A2 | 2/2005 |
| WO | WO 2005/017145 A1 | 2/2005 |
| WO | WO 2005/078096 A2 | 8/2005 |
| WO | WO 2005/078139 A2 | 8/2005 |
| WO | WO 2005/079397 A2 | 9/2005 |
| WO | WO 2005/118806 A2 | 12/2005 |
| WO | WO 2006/013561 A2 | 2/2006 |
| WO | WO 2006/047454 A2 | 5/2006 |
| WO | WO 2006/063356 A1 | 6/2006 |
| WO | WO 2006/111512 A1 | 10/2006 |
| WO | WO 2006/137941 A2 | 12/2006 |
| WO | WO 2007/000668 A2 | 1/2007 |
| WO | WO 2007/035684 A2 | 3/2007 |
| WO | WO 2007/070483 A2 | 6/2007 |
| WO | WO 2007/073737 A1 | 7/2007 |
| WO | WO 2007/090073 A2 | 8/2007 |
| WO | WO 2007/112754 A2 | 10/2007 |
| WO | WO 2008/016924 A2 | 2/2008 |
| WO | WO 2008/042231 A2 | 4/2008 |

(Continued)

OTHER PUBLICATIONS

Chang, "International Search Report," 4 pages, from International Patent Appl. No. PCT/US2008/071837, Korean Intellectual Property Office, Daejon, Republic of Korea (mailed Nov. 27, 2009).

Cheng et al., "MicroRNAs are Aberrantly Expressed in Hypertrophic Heart," Am. J. Pathol. 170(6):1831-1840 (2007).

Sayed et al., "MicroRNAs Play and Essential Role in the Development of Cardiac Hypertrophy," Circ. Res. 100(3):416-424 (2007).

Tatsuguchi et al., "Expression of MicroRNAs is Dynamically Regulated During Cardiomyocyte Hypertrophy," J. Mol. Cell. Cardiol. 42(6):1137-1141 (2007).

(Continued)

*Primary Examiner* — Richard Schnizer
(74) *Attorney, Agent, or Firm* — Cooley LLP

(57) ABSTRACT

The present invention relates to the identification of two microRNAs, miR-499 and miR-208b, that repress fast skeletal muscle contractile protein genes. Expression of miR-499 and/or miR-208b can be used to repress fast fiber genes and activate slow fiber genes in the treatment of musculoskeletal disorders. Inhibition of miR-499 and/or miR-208b is proposed as a treatment for cardiac hypertrophy, myocardial infarction, and/or heart failure. Pharmaceutical compositions comprising antagonists and agonists of miR-499 and miR-208b function are also disclosed.

41 Claims, 39 Drawing Sheets

(56) References Cited

FOREIGN PATENT DOCUMENTS

| WO | WO 2008/043521 A2 | 4/2008 |
|---|---|---|
| WO | WO 2008/061537 A2 | 5/2008 |
| WO | WO 2008/074328 A2 | 6/2008 |
| WO | WO 2008/076324 A2 | 6/2008 |
| WO | WO 2008/147839 A1 | 12/2008 |
| WO | WO 2009/026576 A1 | 2/2009 |
| WO | WO 2009/043353 A2 | 4/2009 |
| WO | WO 2009/058818 A2 | 5/2009 |
| WO | WO 2009/062169 A2 | 5/2009 |
| WO | WO 2009/114681 A2 | 9/2009 |
| WO | WO 2009/149182 A1 | 12/2009 |
| WO | WO 2010/048585 A2 | 4/2010 |

OTHER PUBLICATIONS

Thum et al., "MicroRNAs in the human Heart. A Clue to Fetal Gene Reprogramming in Heart Failure," Circulation 116(3):258-267 (2007).

Lagos-Quintana et al., "New microRNAs from mouse and human," RNA, vol. 9:175-179, 2003.

Lagos-Quintana et al., "Identification of tissue-specific microRNAs from mouse," Current Biology, vol. 12:735-739, 2002.

Sempere et al., "Expression profiling of mammalian microRNAs uncovers a subset of brain-expressed microRNAs with possible roles in murine and human neuronal differentiation," Genome Biology, vol. 5:R13, 2004.

Van Rooij et al., "A signature pattern of stress-responsive microRNAs that can evoke cardiac hypertrophy and heart failure," Proc. Natl. Acad. Sci. USA, vol. 103: 18255-18260, 2006.

Landgraf et al., "A mammalian microRNA expression atlas based on small RNA library sequencing," Cell, vol. 129: 1401-1414, 2007.

Landgraf et al., "A mammalian microRNA expression atlas based on small RNA library sequencing," Cell, Supplementary Table S12, 2007.

Van Rooij et al., "Control of stress-dependent cardiac growth and gene expression by a microRNA," Science, vol. 316: 575-579, 2007.

Habedanck, Supplementary European Search Report for European Application No. 08797004.2, 13 pages, European Patent Office, Munich, mailed Sep. 16, 2011.

Lorell et al., "Left Ventricular Hypertrophy:Pathogenesis, Detection, and Prognosis," Circulation, vol. 102: 470-479, 2000.

Olson, "Transcriptional Control of Heart Development and Disease," Symposium Presentation at Duke University, Sep. 26, 2006.

Olson, Genetic Pathways in Cardiovascular Development and Disease, Symposium Presentation at University of Cincinnati, Sep. 2006.

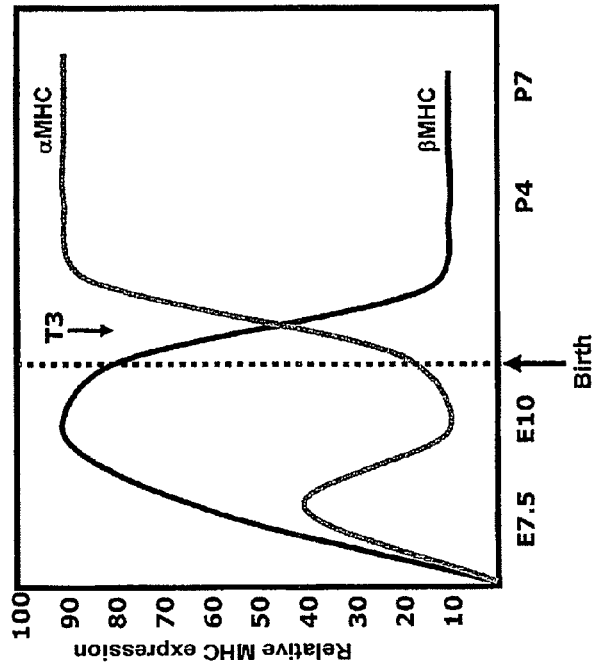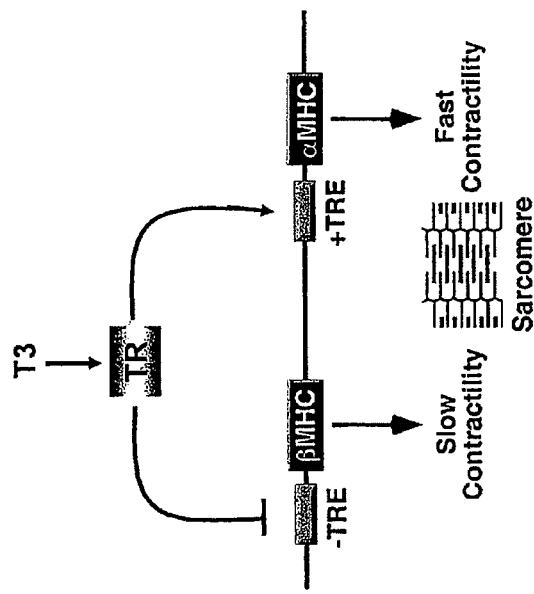
FIG. 2A

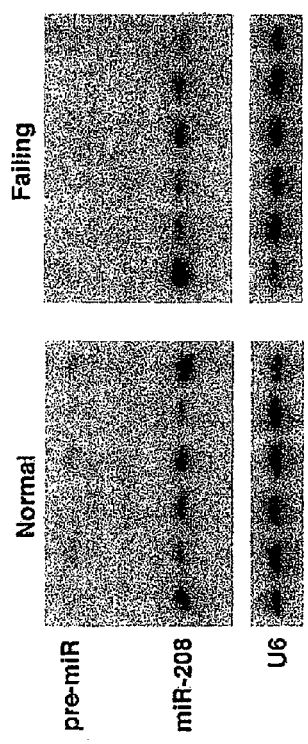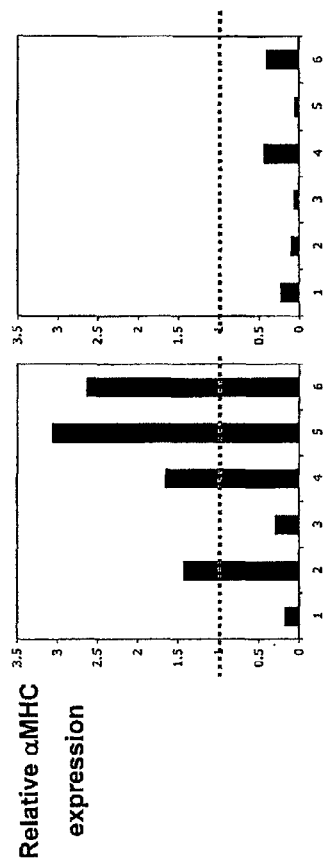
FIG. 3

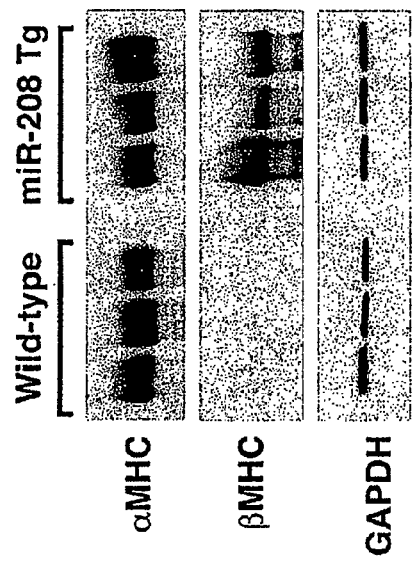
FIG. 9 miR-499 is located within Myosin Heavy Chain 7b

Myosin heavy chain 7b

| | |
|---|---|
| (SEQ ID NO: 18) Mouse | —TCCCTGTGTCTTGGGTGGGCAGCTGTTAAGACTTGCAGTGATGTTTAGCT--CCTCT-GCATGTGAACATCACAGCAAG |
| (SEQ ID NO: 19) Rat | —TCCCTGT--CTTGGGTGGGCAGCTGTTAAGACTTGCAGTGATGTTTAGCT--CCTCT-CCATGTGAACATCACAGCAAG |
| (SEQ ID NO: 20) Human | —CCCCTGTGCCTTGGGCGGGCGGCTGTTAAGACTTGCACTGATGTTTAACT--CCTCT-CCACGTGAACATCACAGCAAG |
| (SEQ ID NO: 21) Dog | —CCCTTGCACCCTGGGCGGGCGGCCGTTAAGACTTGCAGTGATGTTTAACT--CCTCT-CCACGTGAACATCACAGCAAG |
| (SEQ ID NO: 22) Opposum | —CCCTGCCTCCCCGGCGGGGCAGCTGTTAAGACTTGCAGTGATGTTTAATT--CTTCT-CTATGTGAACATGAACAACAAG |
| (SEQ ID NO: 23) Chicken | =======GGAGCGGCAGTTAAGACTTGTAGTGATGTTTAGAT--AATGTATTACATGAACATCACTTTAAG |
| (SEQ ID NO: 24) X tropicalis | —GTCTT-----AGCGAGGAGCAGTTAAGACTTGCCAGTGATGTTTAGTTAAAATCT-TTTCATGAACATCACTTTAAG |

(SEQ ID NO: 25) Pre-miR 499

(SEQ ID NO: 26) miR 499  UUAAGACUUGCAGUGAUGUUU

FIG. 15

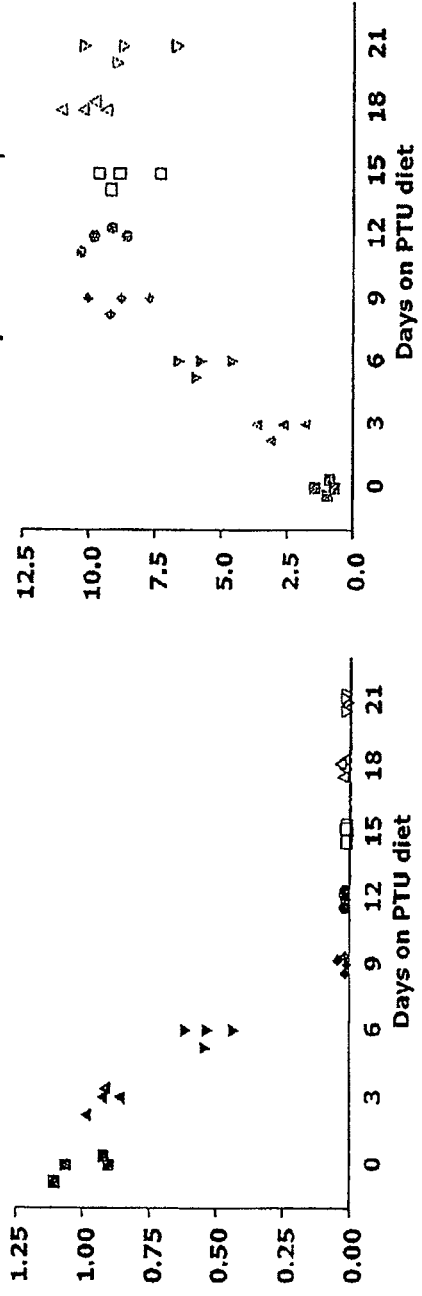
FIG. 21A
FIG. 21B
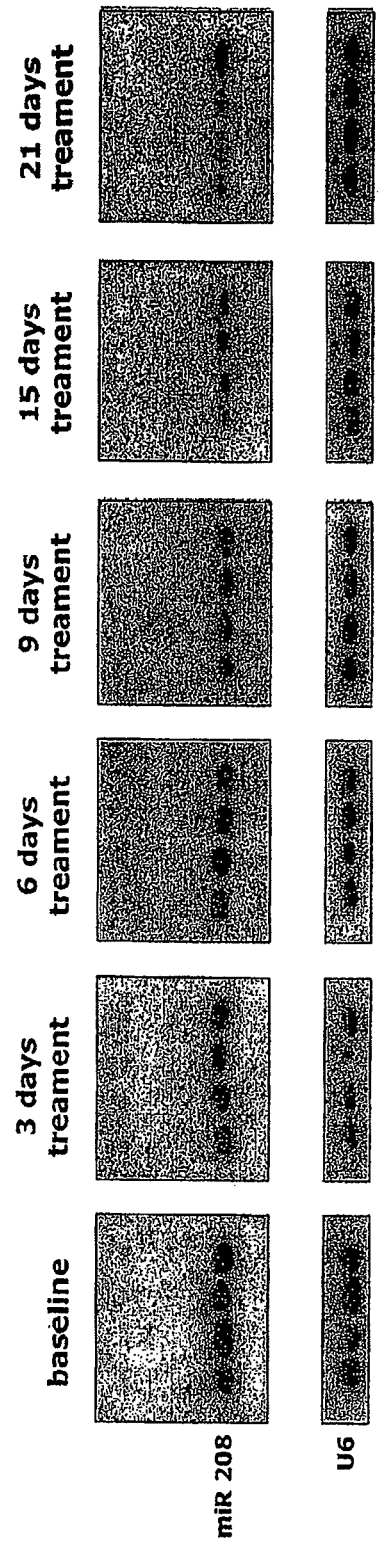
FIG. 21C

Microarray analysis

| | |
|---|---|
| Cardiac troponin I, fast skeletal | 73.5 fold |
| Troponin T3, fast skeletal | 36.8 fold |
| MLC, fast skeletal | 11.3 fold |
| Alpha skeletal actin | 1.3 fold |

FIG. 22

Target prediction:
MiRanda: 15 predicted possible target (THRAP number 8)
PicTar: 46 predicted possible target (THRAP number 1)

3'UTR THRAP1

```
                                3'  UGUUCGAAAAACG------AGCAGAAUA 5' miR 208 (SEQ ID NO:5)
                                    :||  |  |||  :      ||||||||
Human    (SEQ ID NO:6)  UUCUUGCUUUAAAGCAAUUGGUCUAAAAAUAUAUGUA------AUCGUCUUAAUUAAAAGUUGCAGUAGGUUGC
Chimp    (SEQ ID NO:7)  UUCUUGCUUUAAAGCAAUUGGUCUAAAAAUAUAUGUA------AUCGUCUUAAUUAAAACGUUGCAGUAGGUUGC
Murine   (SEQ ID NO:8)  UUCUUGCUUUAAAGCAAUUGGUCUAAAAAUAUAUGUA------AUCGUCUUAAUUAAAAACGUUGCAGUAGGUUGC
Rat      (SEQ ID NO:9)  UUCUUGCUUUAAAGCAAUUGGUCUAAAAAUAUAUGUA------AUCGUCUUAAUUAAAAACGUUGCAGUAGGUUGC
Dog      (SEQ ID NO:10) UUCUUGCUUUAAAGCAAUUGGUCUAAAAAUAUAUGUA------AUCGUCUUAAUUAAAACGUUGCAGUAGGUUGC
Chicken  (SEQ ID NO:11) UUCUUGCUUUAAAGCAAUUGGUCUAAAAAUAUAUAUGUA-----AUCGUCUUAAUUAAAAACGUUGCAGUAGGUUGC
Fugu     (SEQ ID NO:12) UUCCUGCUUUAA-GCAAUUGGUCUAAAAAUAUAUGUAAUGUAAUGUCCUUAAUUAAAAAAAAACAAACUAAGACAAA
Zebrafish(SEQ ID NO:13) UUCCUGCUUAAAGCAAUUGGUCUAAAAUAUAUGUA-----AUCGUCUCAUUACAAAACGAACCAUCAAACG
                        ***  *********  *************  ** ********         **  *********   **
```

FIG. 25

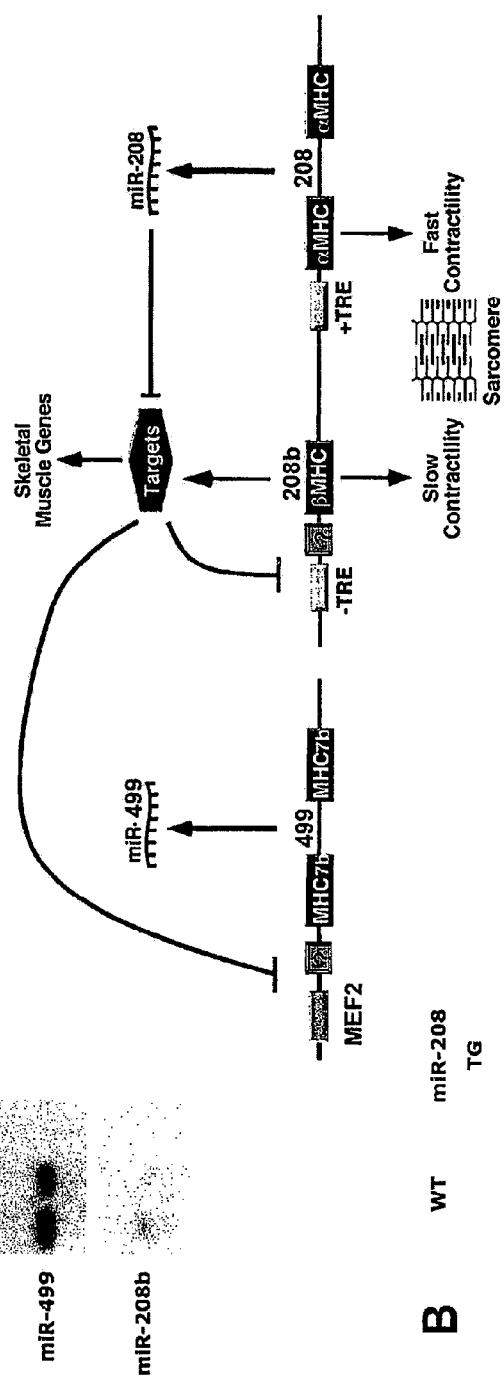
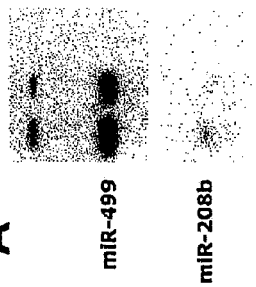
FIG. 33

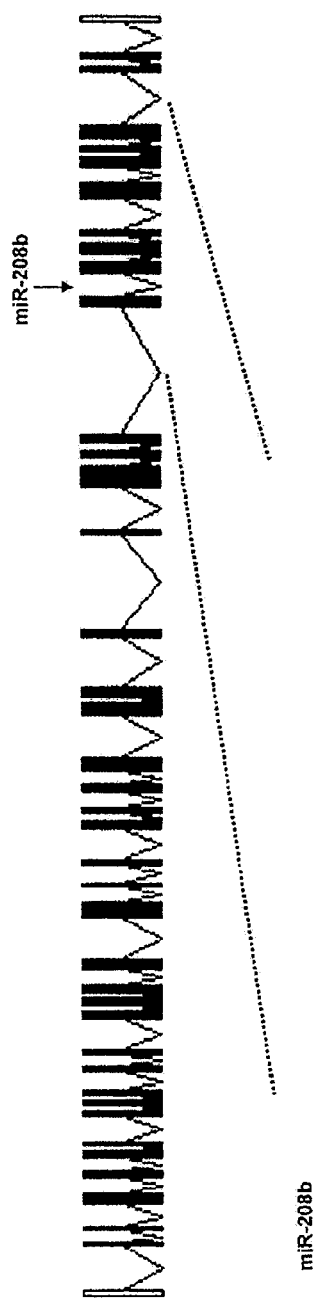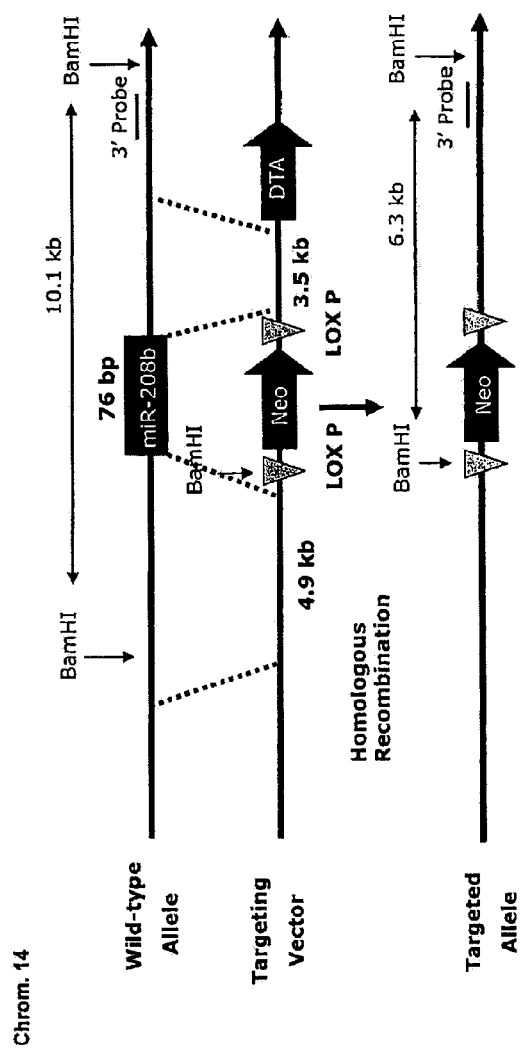
FIG. 35

In vivo approaches to manipulate the Myo-miRs miR-208:
AUAAGACGAGCAAAAAGCUUGU (SEQ ID NO: 5)

miR-208b: AUAAGACGAACAAAAGGUUUGU (SEQ ID NO: 27)

miR-499: UUAAGACUUGCAGUGAUGUUU (SEQ ID NO: 26)
Skeletal muscle 'sponge' approach

MICRO-RNAS THAT CONTROL MYOSIN EXPRESSION AND MYOFIBER IDENTITY

CROSS-REFERENCE TO RELATED APPLICATIONS

This application is a continuation of U.S. application Ser. No. 12/671,436, filed Jun. 25, 2010, which is a national stage application of International Application No. PCT/US2008/071837, filed Jul. 31, 2008, which claims the benefit of U.S. Provisional Application No. 60/952,911, filed Jul. 31, 2007; U.S. Provisional Application No. 60/980,113, filed Oct. 15, 2007, and U.S. Provisional Application No. 60/980,314, filed Oct. 16, 2007, all of which are herein incorporated by reference in their entireties.

STATEMENT OF GOVERNMENT SUPPORT

This invention was made with grant support under grant no. HL53351-06 from the National Institutes of Health. The government has certain rights in the invention.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: MIRG 004 03US SeqList ST25.txt, date recorded: Mar. 12, 2013 file size 9 kilobytes).

FIELD OF THE INVENTION

The present invention relates generally to the fields of developmental biology and molecular biology. More particularly, it concerns gene regulation and cellular physiology in cardiomyocytes and skeletal muscle cells. Specifically, the invention relates to the inhibition of a MEF2-dependent miRNA that results in reduced expression of β-myosin heavy chain β-MHC) as well as a second miRNA that is co-expressed with β-MHC Inhibiton of these miRNAs provides a treatment for cardiac hypertrophy and heart failure. Also contemplated is up-regulation of these two miRNAs to treat musculoskeletal diseases where fast-to-slow muscle fiber switch is desired.

BACKGROUND OF THE INVENTION

Heart disease and its manifestations, including coronary artery disease, myocardial infarction, congestive heart failure and cardiac hypertrophy, clearly presents a major health risk in the United States today. The cost to diagnose, treat and support patients suffering from these diseases is well into the billions of dollars. Two particularly severe manifestations of heart disease are myocardial infarction and cardiac hypertrophy. With respect to myocardial infarction, typically an acute thrombocytic coronary occlusion occurs in a coronary artery as a result of atherosclerosis and causes myocardial cell death. Because cardiomyocytes, the heart muscle cells, are terminally differentiated and generally incapable of cell division, they are generally replaced by scar tissue when they die during the course of an acute myocardial infarction. Scar tissue is not contractile, fails to contribute to cardiac function, and often plays a detrimental role in heart function by expanding during cardiac contraction, or by increasing the size and effective radius of the ventricle, for example, becoming hypertrophic.

With respect to cardiac hypertrophy, one theory regards this as a disease that resembles aberrant development and, as such, raises the question of whether developmental signals in the heart can contribute to hypertrophic disease. Cardiac hypertrophy is an adaptive response of the heart to virtually all forms of cardiac disease, including those arising from hypertension, mechanical load, myocardial infarction, cardiac arrhythmias, endocrine disorders, and genetic mutations in cardiac contractile protein genes. While the hypertrophic response is initially a compensatory mechanism that augments cardiac output, sustained hypertrophy can lead to dilated cardiomyopathy (DCM), heart failure, and sudden death. In the United States, approximately half a million individuals are diagnosed with heart failure each year, with a mortality rate approaching 50%. The causes and effects of cardiac hypertrophy have been extensively documented, but the underlying molecular mechanisms have not been elucidated. Understanding these mechanisms is a major concern in the prevention and treatment of cardiac disease and will be crucial as a therapeutic modality in designing new drugs that specifically target cardiac hypertrophy and cardiac heart failure.

Treatment with pharmacological agents represents the primary mechanism for reducing or eliminating the manifestations of heart failure. Diuretics constitute the first line of treatment for mild-to-moderate heart failure. If diuretics are ineffective, vasodilatory agents, such as angiotensin converting enzyme (ACE) inhibitors (e.g., enalopril and lisinopril) or inotropic agent therapy (i.e., a drug that improves cardiac output by increasing the force of myocardial muscle contraction) may be used. Unfortunately, many of these standard therapies have numerous adverse effects and are contraindicated in some patients. Thus, the currently used pharmacological agents have severe shortcomings in particular patient populations. The availability of new, safe and effective agents would undoubtedly benefit patients who either cannot use the pharmacological modalities presently available, or who do not receive adequate relief from those modalities.

The ratio of α- to β-MHC isoforms in the adult heart is a major determinant of cardiac contractility. β-MHC, the major myosin isoform in the adult heart, displays relatively low ATPase activity, whereas α-MHC has high ATPase activity. In response to a variety of pathological stimuli such as myocardial infarction, hypertension, and other disorders, β-MHC expression increases, while α-MHC expression decreases with a consequent reduction in myofibrillar ATPase activity and reduced shortening velocity of cardiac myofibers, leading to eventual contractile dysfunction. Remarkably, minor changes in α-MHC content of the heart can have a profound influence on cardiac performance.

Numerous signaling pathways, especially those involving aberrant calcium signaling, drive cardiac hypertrophy and pathological remodeling (Heineke & Molkentin, 2006). Hypertrophic growth in response to stress involves different signaling pathways and gene expression patterns than physiological hypertrophy as occurs in response to exercise. Stress-mediated myocardial hypertrophy is a complex phenomenon associated with numerous adverse consequences with distinct molecular and histological characteristics causing the heart to fibrose, dilate and decompensate which, through myocyte degeneration and death, often culminates in heart failure. As such, there has been intense interest in deciphering the underlying molecular mechanisms and in discovering novel therapeutic targets for suppressing adverse cardiac growth.

Adult skeletal muscle fibers can be categorized into fast and slow twitch subtypes based on specialized contractile and metabolic properties. These properties reflect the expression of specific sets of fast and slow contractile protein isoforms of myosin heavy and light chains, tropomyosin, and troponins, as well as myoglobin (Naya et al., 2000). Slow-twitch muscles are primarily used in chronic activities such as posture maintenance and sustained locomotor activity. Fast-twitch fibers are used primarily for high-force burst activities. The adult skeletal muscle phenotype is not static but instead retains the ability to adjust to variations in load bearing and contractile usage patterns, resulting in adaptations in morphology, phenotype, and contractile properties. For example, the removal of body loading in the microgravity environment of space flight results in a marked degree of muscle atrophy and an altered protein phenotype that correlates with a slow-to-fast change in contractile and metabolic properties for both rodents and humans (Tsika et al., 2002; Baldwin and Haddad, 2001; Edgerton and Roy, (2000); Fitts et al., 2000).

Disuse atrophy, which is a muscular atrophy that results from lack of muscle use, is typically seen in bedridden people, people with limbs in casts, or those who are inactive for other reasons. Disruptions in myofiber electrical activity, including denervation, also lead to muscle atrophy. After short periods of disuse, muscle atrophy is reversible. Extreme disuse of a muscle, however, may result in a permanent loss of skeletal muscle fibers and the replacement of those fibers by connective tissue. It is contemplated that by repressing fast fiber genes in skeletal muscle and thereby activating the reciprocal expression of slow fiber genes, the symptoms of muscle atrophy may be reduced or prevented. There is also a positive correlation of insulin resistance (a deficiency of insulin-stimulated glucose uptake seen in patients with type II diabetes mellitus) with the percentage of slow-versus fast-twitch muscle fibers.

MicroRNAs have recently been implicated in a number of biological processes including regulation of developmental timing, apoptosis, fat metabolism, and hematopoietic cell differentiation among others. MicroRNAs (miRs) are small, non-protein coding RNAs of about 18 to about 25 nucleotides in length that are derived from individual miRNA genes, from introns of protein coding genes, or from poly-cistronic transcripts that often encode multiple, closely related miRNAs. See review of Carrington et al. (2003). MiRs act as repressors of target mRNAs by promoting their degradation, when their sequences are perfectly complementary, or by inhibiting translation, when their sequences contain mismatches.

miRNAs are transcribed by RNA polymerase II (pol II) or RNA polymerase III (pol III; see Qi et al. (2006) Cellular & Molecular Immunology Vol. 3:411-419) and arise from initial transcripts, termed primary miRNA transcripts (pri-miRNAs), that are generally several thousand bases long. Pri-miRNAs are processed in the nucleus by the RNase Drosha into about 70- to about 100-nucleotide hairpin-shaped precursors (pre-miRNAs). Following transport to the cytoplasm, the hairpin pre-miRNA is further processed by Dicer to produce a double-stranded miRNA. The mature miRNA strand is then incorporated into the RNA-induced silencing complex (RISC), where it associates with its target mRNAs by base-pair complementarity. In the relatively rare cases in which a miRNA base pairs perfectly with an mRNA target, it promotes mRNA degradation. More commonly, miRNAs form imperfect heteroduplexes with target mRNAs, affecting either mRNA stability or inhibiting mRNA translation.

The 5' portion of a miRNA spanning bases 2-8, termed the 'seed' region, is especially important for target recognition (Krenz and Robbins, 2004; Kiriazis and Kranias, 2000). The sequence of the seed, together with phylogenetic conservation of the target sequence, forms the basis for many current target prediction models. Although increasingly sophisticated computational approaches to predict miRNAs and their targets are becoming available, target prediction remains a major challenge and requires experimental validation. Ascribing the functions of miRNAs to the regulation of specific mRNA targets is further complicated by the ability of individual miRNAs to base pair with hundreds of potential high and low affinity mRNA targets and by the targeting of multiple miRNAs to individual mRNAs. Enhanced understanding of the functions of miRNAs will undoubtedly reveal regulatory networks that contribute to normal development, differentiation, inter- and intra-cellular communication, cell cycle, angiogenesis, apoptosis, and many other cellular processes. Recently, the inventors reported a cardiac-specific microRNA, miR-208, which is encoded by an intron of the α-myosin heavy chain (MHC) gene, and is required for up-regulation of β-MHC expression in response to cardiac stress and for repression of fast skeletal muscle genes in the heart (see co-pending application WO2008/016924, which is herein incorporated by reference in its entirety). The present invention expands on the involvement of microRNAs in the heart and skeletal muscle.

SUMMARY OF THE INVENTION

The inventors have discovered key roles of microRNAs as regulators of the growth, function and stress responsiveness of the heart, revealing undiscovered regulatory mechanisms and potential therapeutic targets for heart disease. Accordingly, the present invention provides a method of treating pathologic cardiac hypertrophy, heart failure, or myocardial infarction in a subject in need thereof. In one embodiment, the method comprises identifying a subject having cardiac hypertrophy, heart failure, or myocardial infarction; and inhibiting expression or activity of miR-499 and/or miR-208b in heart cells of said subject. In another embodiment, the method further comprises administering to the subject a second therapy. The second therapy may be, for example, a beta blocker, an ionotrope, a diuretic, ACE inhibitor, AII antagonist, BNP, a $Ca^{++}$-blocker, and ERA, or an HDAC inhibitor.

In some embodiments of the invention, inhibiting the expression or activity of miR-499 and/or miR-208b comprises administering an antagomir of miR-499 and/or miR-208b. In one embodiment, the present invention provides a miR-499 or miR-208b antagomir. In another embodiment, miR-499 and/or miR-208b expression or activity is inhibited by administering an antisense oligonucleotide that targets the mature miR499 and/or miR-208b sequence. In yet another embodiment, miR-499 and/or miR-208b expression or activity is inhibited by administering an inhibitory RNA molecule, wherein the inhibitory RNA molecule comprises a sequence having identity to the mature miR-499 and/or miR-208b sequence. The inhibitory RNA molecule may be a ribozyme, siRNA or shRNA molecule.

The present invention also provides a method of preventing pathologic hypertrophy or heart failure in a subject in need thereof comprising identifying a subject at risk of developing pathologic cardiac hypertrophy or heart failure; and inhibiting expression or activity of miR-499 or miR-208b in heart cells of said subject. In one embodiment, inhibiting comprises delivering to the heart cells an inhibitor of miR-499 or miR-208b. In another embodiment, the subject at risk may exhibit one or more risk factors selected from the group consisting of long standing uncontrolled hypertension, uncorrected valvular disease, chronic angina, recent myocardial infarction, congenital predisposition to heart disease, and pathological hypertrophy.

Antagomirs, antisense oligonucleotides, inhibitory RNA molecules, or other modulators of miR-499 or miR-208b expression or activity may be administered by any method known to those in the art suitable for delivery to the targeted organ, tissue, or cell type. For example, in certain embodiments of the invention, the modulator of miR-499 or miR-208b may be administered by parenteral administration, such as intravenous injection, intraarterial injection, intrapericardial injection, or subcutaneous injection, or by direct injection into the tissue (e.g., cardiac tissue, skeletal muscle tissue). In some embodiments, the modulator of miR-499 or miR-208b may be administered by oral, transdermal, intraperitoneal, subcutaneous, sustained release, controlled release, delayed release, suppository, or sublingual routes of administration. In other embodiments, the modulator of miR-499 or miR-208b may be administered by a catheter system.

The present invention also contemplates a method of treating or preventing a musculoskeletal disorder in a subject in need thereof. In one embodiment, the method comprises identifying a subject having or at risk of a musculoskeletal disorder; and increasing the expression and/or activity of miR-499 and/or miR-208b in skeletal muscle cells of said subject. The musculoskeletal disorder may include, for example, disuse atrophy, muscle wasting in response to antigravity, and denervation. In some embodiments, increasing the expression and/or activity of miR-499 and/or miR-208b comprises administering to said subject a polynucleotide comprising a mature miR-499 and/or mature miR-208b sequence. In other embodiments, increasing the expression and/or activity of miR-499 and/or miR-208b comprises administering to said subject an expression vector that encodes miR-499 and/or miR-208b. In another embodiment, the method further comprises administering to the subject a non-miR-499 or miR-208b therapy.

In one embodiment, the present invention provides a method of regulating cardiac or skeletal muscle contractility comprising administering a modulator of miR-499 and/or miR-208b expression or activity to heart or skeletal muscle cells. In another embodiment, there is provided a method of regulating cardiac contractile protein gene expression comprising administering a modulator of miR-499 and/or miR-208b expression or activity to heart cells. In another embodiment, there is provided a method of regulating skeletal muscle contractile protein gene expression comprising administering a modulator of miR-499 and/or miR-208b expression or activity to skeletal muscle cells. In still another embodiment, the present invention provides a method of inducing a fiber type switch of a skeletal muscle cell comprising administering a modulator of miR-499 and/or miR-208b expression or activity to the skeletal muscle cell. The modulator may be an agonist or an antagonist of miR-499 and/or miR-208b expression or activity. In some embodiments, the expression of THRAP1, PURbeta, myostatin (a.k.a. GDF8), Sox 6 and fast contractile proteins are increased in a cell by contacting the cell with a miR-499 inhibitor. In other embodiments, expression of THRAP1, PURbeta, myostatin, Sox 6 and fast contractile proteins are decreased in a cell by contacting the cell with a miR-499 agonist. In another embodiment, the expression of Sp3, Myostatin, PURbeta, THRAP1, and fast contractile proteins are increased in a cell by contacting the cell with a miR-208b inhibitor. In still another embodiment, the expression of Sp3, Myostatin, PURbeta, THRAP1, and fast contractile proteins are decreased in a cell by contacting the cell with a miR-208b agonist. Examples of fast skeletal muscle contractile protein genes that may be increased or decreased according to the methods of the present invention include: troponin 12; troponin T3, myosin light chain, or alpha skeletal actin.

The present invention also encompasses a transgenic, non-human mammal, the cells of which fail to express a functional miR-499 and/or miR-208b. In another embodiment, the invention provides a transgenic, non-human mammal, the cells of which comprise a miR-499 and/or miR-208b coding region under the control of a heterologous promoter active in the cells of said non-human mammal. In some embodiments, the mammal is a mouse.

The present invention provides a method for identifying a modulator of miR-499 and/or miR-208b. In one embodiment, the method comprises contacting a cell with a candidate substance; assessing miR-499 and/or miR-208b activity or expression; and comparing the activity or expression in step (b) with the activity or expression in the absence of the candidate substance, wherein a difference between the measured activities or expression indicates that the candidate substance is a modulator of miR-499 and/or miR-208b. The cell may be contacted with the candidate substance in vitro or in vivo. The candidate substance may be a protein, a peptide, a polypeptide, a polynucleotide, an oligonucleotide, or small molecule. The modulator of miR-499 and/or miR-208b may be an agonist or antagonist of miR-499 and/or miR-208b. The modulator of miR-499 and/or miR-208b may be an agonist or antagonist of an upstream regulator of miR-499 and/or miR-208b, such as miR-208.

The present invention also provides a pharmaceutical composition comprising an inhibitor of miR-499 and/or miR-208b. The inhibitor may be an antagomir, an antisense oligonucleotide, or an inhibitory RNA molecule. In another embodiment, the present invention provides a pharmaceutical composition comprising a polynucleotide containing a mature sequence of miR-499 and/or miR-208b. The polynucleotide may be contained within an expression vector.

BRIEF DESCRIPTION OF THE DRAWINGS

The invention may be better understood by reference to one or more of these drawings in combination with the detailed description of specific embodiments presented herein.

(FIG. 1A) MiR-208 is encoded within an intron of the α-MHC gene. Asterisks indicate sequence conservation. (FIG. 1B) Detection of miR-208 transcripts by Northern analysis of adult mouse tissues. U6 mRNA serves as a loading control.

FIG. 2A-B. Regulation of α- and β-MHC. (FIG. 2A) Regulation of class switch by thyroid hormone and TRE. (FIG. 2B) Model for stress/hypothyroidism in fast-to-slow muscle fiber contractility switch.

FIG. 3. Detection of miR-208 in human heart. Transcripts for α-MHC and miR-208 were detected by Northern blot of cardiac tissue from six normal individuals and six individuals with idiopathic cardiomyopathy. A close correlation exists between the level of expression of α-MHC and pre-miR-208, whereas mature miR-208 expression is maintained after the latter has been down-regulated.

(FIG. 4A) Strategy to generate miR-208 mutant mice by homologous recombination. The pre-miRNA sequence was replaced with a neomycin resistance cassette flanked by loxP sites. The neomycin cassette was removed in the mouse germline by breeding heterozygous mice to transgenic mice harboring the CAG-Cre transgene. (FIG. 4B) Detection of miR-208 transcripts by Northern analysis of hearts from wild-type and miR-208 mutant mice.

FIG. 9. Western analysis of α and β-MHC protein levels in adult wild-type and miR-208 transgenic animals. GAPDH was detected as a loading control.

FIG. 15. Structure of the Myh7b locus and the position of the miR-499 coding region within it.

(FIG. 16A) Myh7b, like miR-499, is specifically expressed in the heart and slow skeletal muscle (soleus). (FIG. 16B) Real-time PCR analysis for miR-499 on heart and 4 skeletal muscle types (gastrocnemius/plantaris (GP), tibialis anterior (TA) extensor digitorum longus (EDL), or soleus) confirms that miR-499 is predominantly expressed in the heart and soleus. Only minor levels of miR-499 expression can be detected in TA and EDL. (FIG. 16C) In situ hybridization indicates that during embryogenesis, myh7b is specifically expressed in the heart and somites. (FIG. 16D) Northern blot analysis for both wild-type and miR-208 mutant animals shows that in the absence of miR-208, the expression of miR-499 is specifically absent in the heart, while it is still expressed in soleus (lower blot).

FIG. 21A-C Inhibition of α-MHC expression leads to decreased levels of miR-208. (FIG. 4A-B) Relative expression levels for α- and β-MHC transcripts at 0, 3, 6, 9, 12, 15, 18 and 21 days of PTU exposure.

FIG. 22. Upregulation of fast skeletal genes in miR-208 knock-out.

FIG. 25. THRAP1 as a predicted target of miR-208. Sequence alignment of putative miR-208 binding site in 3' UTR of THRAP1 shows a high level of complementarity and sequence conservation (SEQ ID NOS: 6-13).

(FIG. 30A) Northern analysis shows that mir-208b is expressed at very low levels in the heart at baseline conditions and is not expressed in fast skeletal muscle fibers, such as gastrocnemius/plantaris (GP), tibialis anterior (TA) or extensor digitorum longus (EDL). MiR-208b is highly expressed in the slow skeletal muscle soleus. (FIG. 30B) Realtime PCR analysis for the indicated myosin genes shows that blockade of thyroid receptor signaling by feeding animals PTU-containing chow represses α-MHC and induces β-MHC expression in cardiac tissue of rats. This effect can be reversed by subsequent supplementation of thyroid hormone (T3). The expression of myh7b mirrors the expression pattern of β-MHC to a lesser extent. (FIG. 30C) Shortly after birth there is a shift from β-MHC towards more α-MHC. While miR-208 is responsible for miR-499 activation in adult heart, Northern blot analysis on cardiac samples of p1, p6 and adult wild-type and miR-208 mutant animals indicate the presence of miR-208b, generated from the β-MHC gene, to be sufficient to drive miR-499 expression even in the absence of miR-208. (FIG. 30D) Northern blot analysis for the myomiRs indicates that miR-208b mirrors the reduced induction of β-MHC in response to stress signaling in the absence of miR-208. MiR-208 knockout animals exert a reduced increase in β-MHC in response to stress and hypothyroidism. While northern analysis shows a severe induction of miR-208b in wild-type (WT) animals in response to PTU, the induction of miR-208b in the absence of miR-208 (knockout, KO) is only minor. Note that the presence of either 208a or 208b is sufficient to activate myh7b/miR-499.

FIG. 33A-C. miR-208 regulates the expression of miR-208b and miR-499. (A) Northern blot showing that the expression of miR-499 and miR-208b are dose-dependently downregulated in miR-208 heterozygote (+/−) and homozygote (KO) mutant animals. (B) MiR-208b is upregulated in miR-208 trangenic animals which correlates with β-MHC expression. (C) Schematic diagram of the regulation of miR-499 by miR-208 in cardiac muscle.

FIG. 35. Schematic model of targeting strategy to design a miR-208b knockout mouse model.

(FIG. 37A) A gel mobility shift assay was performed using nuclear extracts from COS-1 cells transfected with either empty pcDNA-Flag or Flag-MEF2C and the radiolabeled MEF2 site as probe. While pcDNA-Flag is unable to bind the radiolabeled MEF2-site (lane 1), overexpression of MEF2C induces binding (lane 2) which can be supershifted with 1 μg of polyclonal Flag antibody (lane 3). Specific and nonspecific competitors were used at 50-fold molar excess (lane 4-6). (FIG. 37B) COS cells (24-well plates, $5 \times 10^4$ cells/well) were transfected with 100 ng of the myh7b-luciferase reporters (wild-type and Mef2 mutant), 50 ng expression vectors encoding Mef2c, a Mef2 co-activator, myocardin proteins and 30 ng of pCMV-lacZ. Activation of the myh7b reporter by Mef2c and myocardin required the Mef2-binding site. (FIG. 37C) MEF2 site is essential for cardiac expression of myh7b/miR-499. LacZ transgenic mouse embryos were generated, and stained for expression of β-galactosidase at E12.5 and p1. While a region 0.8 Kb upstream of the myh7b gene was sufficient to drive cardiac lacZ expression, mutation of the MEF2 site abolished expression in the heart. (FIG. 37D) Northern blot analysis indicates that miR-499 expression is increased in hearts of cardiac specific MEF2D transgenic animals, while the level of miR-499 is decreased in hearts where MEF2C and -D are deleted.

(FIG. 38A) Northern blot analysis for miR-499 indicates that transgenic overexpression of miR-499, using a muscle specific promoter, efficiently induces the level of miR-499 in all muscle types. (FIG. 38B) Real-time PCR analysis shows that transgenic overexpression results in effective overexpression of miR-499 compared to the baseline cardiac expression level, with the highest levels in the fast skeletal muscle types (GP, TA and EDL). (FIG. 38C) Real-time PCR analysis on muscle tissue of either wild-type or transgenic animals shows that overexpression of miR-499 is sufficient to drive β-MHC expression in soleus, TA and EDL, while it represses fast skeletal troponin 12 (TnnI2) and T3 (TnnT3) in heart, soleus and EDL. (FIG. 38D) Metachromatic ATPase staining of snap-frozen histological sections of myofibers of both wild-type and miR-499 transgenic animals show a dramatic increase in slow myofibers in fast fibers (EDL) of the transgenic mice. (FIG. 38E) The repressive effect of miR-208 ablation on β-MHC expression in response to PTU is absent when miR-499 is re-introduced. Transgenically reintroducing miR-499 in heart of miR-208 mutant animals results in a severe induction of β-MHC and its corresponding miRNA, miR-208b. (FIG. 38F) While miR-208 removal induces an inappropriate induction of fast skeletal genes, miR-499 very potently represses these genes when transgenically expressed in the miR-208 mutant animals.

DETAILED DESCRIPTION OF ILLUSTRATIVE EMBODIMENTS

Figure 1:
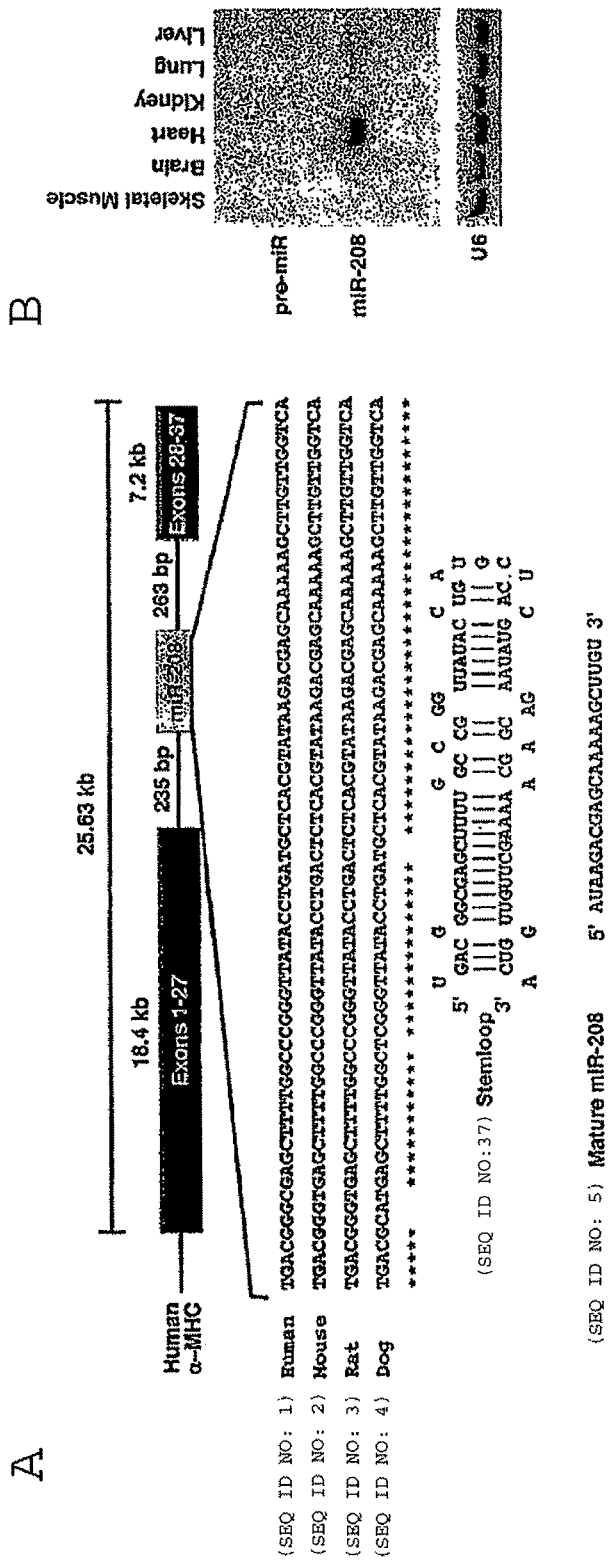
FIG. 1A-B. miR-208 is encoded by the α-MHC gene and is expressed specifically in the heart.
Figure 2B:
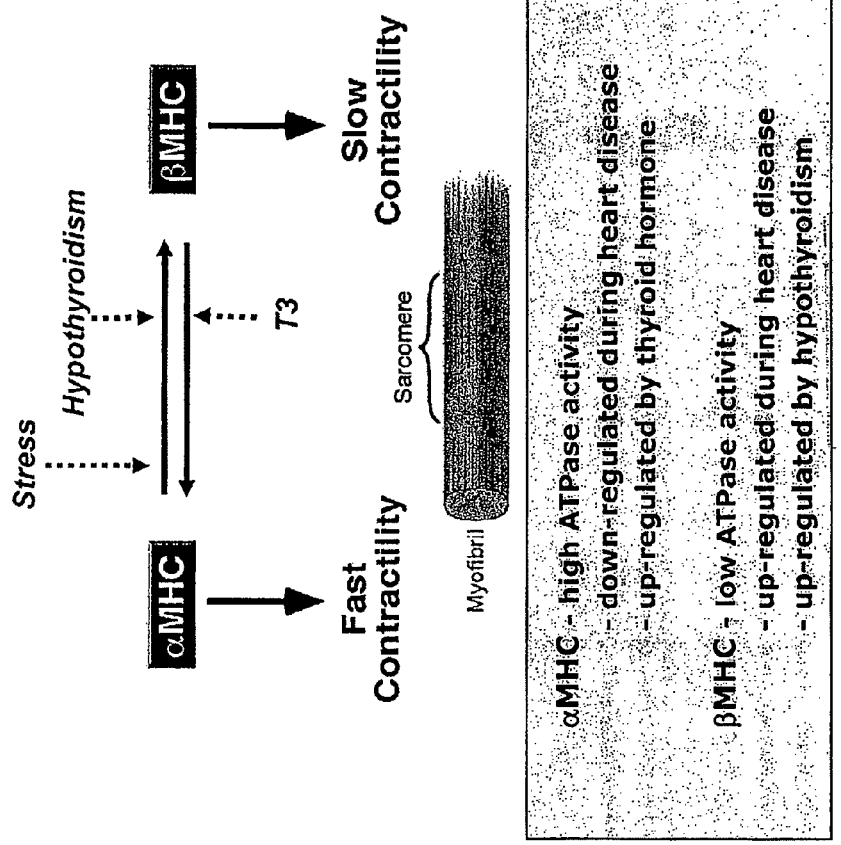
Figure 4:
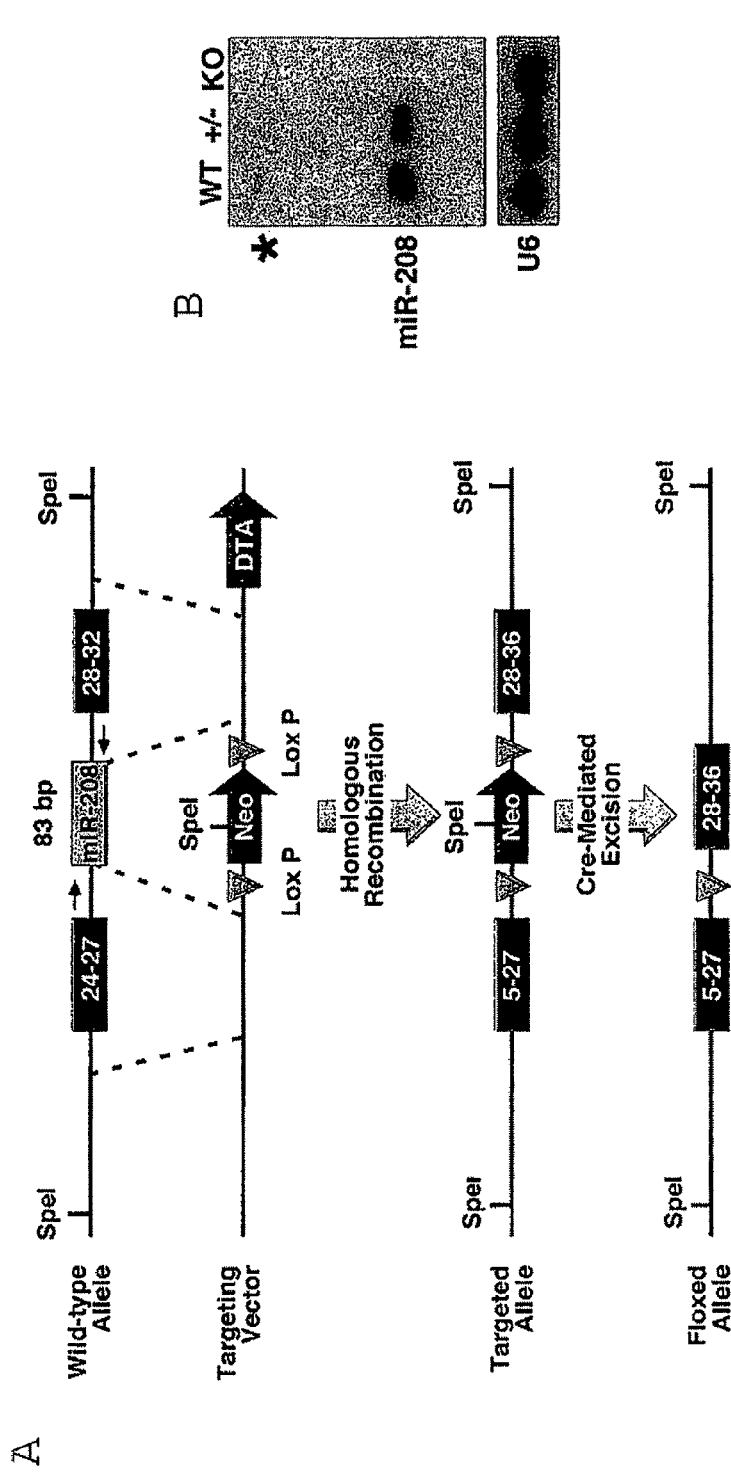
FIG. 4A-B. Generation of miR-208 mutant mice.
(FIG. 4C) Northern blot analysis of miR-208 in cardiac rat tissue at the indicated time points during PTU treatment.

Cardiac and skeletal muscles respond to a variety of pathophysiological stimuli such as workload, thyroid hormone signaling and injury by modulating the expression of myosin isoforms, which regulate the efficiency of contraction. Recently, the inventors reported a cardiac-specific microRNA, miR-208, which is encoded by an intron of the α-myosin heavy chain (MHC) gene, and is required for up-regulation of β-MHC expression in response to cardiac stress and for repression of fast skeletal muscle genes in the heart (see co-pending application WO2008/016924, which is herein incorporated by reference in its entirety).

Here, the inventors extend their earlier work and show that miR-208 is also required for cardiac expression of closely related microRNAs, miR-499 and miR-208b, which are encoded by an intron of the Myh7b gene and the βMHC gene, respectively. Expression of Myh7b and miR-499 in the heart, as well as in slow skeletal muscle, is controlled by the MEF2 transcription factor, a signal-dependent regulator of striated muscle gene expression. Forced expression of miR-499 or miR-208 is sufficient to mediate a fast to slow myofiber conversion in vivo. Mir-208 and miR-499 can negatively regulate the expression of Thrap1, a thyroid hormone receptor coregulator, and members of the PUR family of transcription factors, which in turn negatively regulate β-MHC expression in cardiac and skeletal muscle. Sox6 functions as a repressor of slow fiber type-specific genes. Knockdown of Sox6 expression in wild-type myotubes results in a significant increase in β-MHC expression. Analysis of the β-MHC promoter revealed a Sox consensus sequence which suggests that Sox6 plays a critical role in the fiber type differentiation of fetal skeletal muscle and β-MHC regulation in the heart. These findings unveil a common regulatory mechanism in which Myh genes regulate the gene expression patterns of striated muscles by encoding regulatory microRNAs that govern contractility and signal responsiveness. Strategies to manipulate skeletal and cardiac muscle gene expression by modulating miR-499 expression in the settings of striated muscle diseases are described in light of these discoveries.

The inventors have also discovered the genome to contain a second version of miR208, called miR-208b, which is located within the β-MHC gene at intron 31, and like β-MHC, miRNA 208b is expressed solely in the heart and slow skeletal muscle (soleus). The sequence of this microRNA is largely overlapping with miR-208 with a 100% homology in the so called seed region, the region of the microRNA that defines mRNA targets of a certain miRNA. Thus, miR-208b can have profound effects on cardiac contractility in humans, and modulation of miR-208b to regulate cardiac contractility is also contemplated by the invention.

Thus, the invention encompasses agonism of miR-499 and/or miR-208b expression or activity, either by therapeutically activating the endogenous miR-208b gene or miR-208 gene (to upregulate miR-499) or introducing exogenous miR-499

MiR-208, which has been shown to regulate miR-499 expression, is an intronic miRNA that is located within an intron of the α-MHC gene. The precise intron location is dependent on the particular species and specific transcript. For example, in humans, miR-208 is encoded within the 28$^{th}$ intron of the α-MHC gene, while in mice, it is encoded within the 29$^{th}$ intron. The pre-miRNA encoding sequences for miR-208 for human, mouse, rat, and canine are provided in SEQ ID NO:14, SEQ ID NO:15, SEQ ID NO:16, SEQ ID NO:17, respectively. The mature miR-208 sequence is provided in SEQ ID NO:5. Like α-MHC, miR-208 is expressed solely in the heart. (FIG. 1).

```
Human pre-miR-208
                                                                (SEQ ID NO: 14)
acgggcgagc ttttggcccg ggttatacct gatgctcacg tataagacga gcaaaaagct tgttggtcag a Mouse pre-miR-208
                                                                (SEQ ID NO: 15)
acgggtgagc ttttggcccg ggttatacct gactctcacg tataagacga gcaaaaagct tgttggtcag a Rat pre-miR-208
                                                                (SEQ ID NO: 16)
acgggtgagc ttttggcccg ggttatacct gactctcacg tataagacga gcaaaaagct tgttggtcag a Canine pre-miR-208
                                                                (SEQ ID NO: 17)
acgcatgagc ttttggctcg ggttatacct gatgctcacg tataagacga gcaaaaagct tgttggtcag a
``` or miR-208b into the heart, either using the miRNA itself or by the use of adenoviral vectors or other means of ectopic expression to elevate β-MHC expression. The up-regulation of several fast skeletal muscle contractile protein genes in the hearts of miR-208 mutant mice suggests that miR-208 and miR-208b typically repress the fast skeletal muscle gene program, which implicates a similar role for miR-499 in skeletal and cardiac muscle. Thus, activation of these genes in the heart represents a potential approach to regulate cardiac contractility.

In addition, the inventors present use of miR-499 and/or miR-208b to repress fast fiber genes in skeletal muscle thereby activating the reciprocal expression of slow fiber genes. Expression of slow fiber genes are coupled to enhanced insulin sensitivity and skeletal muscle endurance. Repression of slow fiber genes and activation of fast fiber genes in skeletal muscle is associated with numerous musculoskeletal disorders including disuse atrophy, muscle wasting in response to anti-gravity, and denervation.

Thus, the present inventors have discovered that, like miR-208, miR-499 is a muscle-specific and essential regulator of β-MHC gene expression in the heart. In addition, miR-208b was discovered to be a muscle-specific and essential regulator of myosin gene expression in the heart that in addition regulates cardiac fibrosis. Both of these discoveries are completely novel as is the use of these microRNAs to control cardiac contractility and skeletal muscle function.

Analysis of the genomic location of the miR-499 gene showed it to be contained within the 20$^{th}$ intron of the Myh7b gene, a homolog of the α-MHC gene (FIG. 15; SEQ ID NO:26 recites the mature miRNA sequence; SEQ ID NO:25 shows the stem-loop structure of the precursor sequence). The pre-miRNA encoding sequences for miR-499 for mouse, rat, human, canine, opposum, chicken and X. tropicalis are provided in SEQ ID NO:18, SEQ ID NO:19, SEQ ID NO:20, SEQ ID NO:21, SEQ ID NO:22, SEQ ID NO:23 and SEQ ID NO:24, respectively. (FIG. 15). The Myh7b gene is conserved in vertebrates and is expressed solely in the heart and slow skeletal muscle (e.g. soleus).

Using the PicTar algorithm for the identification of miRNA targets (Krek et al., 2005), the inventors identified thyroid hormone receptor associated protein 1 (THRAP1) as a predicted target for miR-208. THRAP1 3' UTR sequences from human, chimp, mouse, rat, canine, chicken, fugu, and zebrafish are provided in SEQ ID NO:6, SEQ ID NO:7, SEQ ID NO:8, SEQ ID NO:9, SEQ ID NO:10, SEQ ID NO:11, SEQ ID NO:12, and SEQ ID NO:13, respectively (FIG. 25).

In a further search for microRNAs that might be involved in the regulation of muscle contractility, the inventors found the βMHC gene to contain miR208b, which is closely related to miR-208, in intron 31. Expression of miR-208b follows that of βMHC, namely it is expressed solely in the heart and slow skeletal muscle (soleus). The sequence of this microRNA is largely overlapping with miR-208 with a 100% homology in the so called seed region (indicated by underlining), the part of the microRNA that helps to define mRNA targets of a certain miRNA:

```
                                                (SEQ ID NO: 5)
    miR-208   AUAAGACGAGCAAAAAGCUUGU (SEQ ID NO: 27)
    miR-208b  AUAAGACGAACAAAAGGUUUGU
```

Figure 28:
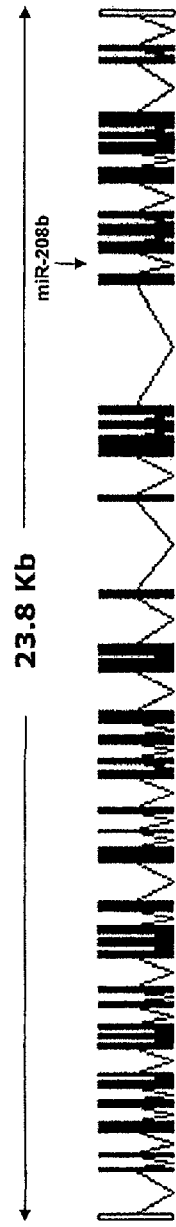
FIG. 28. Structure of the Myh7 locus β-MHC) and the position of the miR-208b coding region within it (SEQ ID NO: 27 and SEQ ID NOS: 30-36).

The pre-miRNA encoding sequences for miR-208b for human, mouse, rat, canine, opposum, and X. tropicalis are provided in SEQ ID NO:30, SEQ ID NO:31, SEQ ID NO:32, SEQ ID NO:33, SEQ ID NO:34, and SEQ ID NO:35, respectively. (FIG. 28). FIG. 28 also shows the stem-loop structure of the miR-208b precursor sequence (SEQ ID NO:36).

Methods of Treating Cardiac Hypertrophy, Heart Failure, and Myocardial Infarction The present invention provides a method for treating pathologic cardiac hypertrophy, heart failure, or myocardial infarction in a subject in need thereof. In one embodiment, the method comprises identifying a subject having cardiac hypertrophy, heart failure, or myocardial infarction and inhibiting expression or activity of miR-499 and/or miR-208b in heart cells of the subject. In another embodiment, the method comprises identifying a subject at risk of developing pathologic cardiac hypertrophy, heart failure, or myocardial infarction and inhibiting expression or activity of miR-499 and/or miR-208b in heart cells of the subject. The subject at risk of developing pathologic cardiac hypertrophy or heart failure may exhibit one or more risk factors including, for example, long standing uncontrolled hypertension, uncorrected valvular disease, chronic angina, recent myocardial infarction, congenital predisposition to heart disease or pathological hypertrophy. In certain embodiments, the subject at risk may be diagnosed as having a genetic predisposition to cardiac hypertrophy. In some embodiments of the invention, the subject at risk may have a familial history of cardiac hypertrophy.

In another embodiment, the present invention provides a method of preventing cardiac hypertrophy and dilated cardiomyopathy in a subject in need thereof comprising inhibiting expression or activity of miR-499 and/or miR-208b in heart cells of the subject. In yet a further embodiment, the present invention provides a method of inhibiting progression of cardiac hypertrophy in a subject in need thereof comprising inhibiting expression or activity of miR-499 and/or miR-208b in heart cells of the subject. In certain embodiments, the present invention provides a method of increasing exercise tolerance, reducing hospitalization, improving quality of life, decreasing morbidity, and/or decreasing mortality in a subject with heart failure or cardiac hypertrophy comprising inhibiting expression or activity of miR-499 and/or miR-208b in heart cells of the subject.

Thus, the present invention provides methods for the treatment of cardiac hypertrophy, heart failure, or myocardial infarction utilizing inhibitors of miR-499 or miR-208b. Preferably, administration of a miR-499 and/or miR-208b inhibitor results in the improvement of one or more symptoms of cardiac hypertrophy, heart failure, or myocardial infarction in the subject, or in the delay in the transition from cardiac hypertrophy to heart failure. The one or more improved symptoms may be, for example, increased exercise capacity, increased cardiac ejection volume, decreased left ventricular end diastolic pressure, decreased pulmonary capillary wedge pressure, increased cardiac output, increased cardiac index, lowered pulmonary artery pressures, decreased left ventricular end systolic and diastolic dimensions, decreased cardiac fibrosis, decreased collagen deposition in cardiac muscle, decreased left and right ventricular wall stress, decreased wall tension, increased quality of life, and decreased disease related morbidity or mortality. In addition, use of inhibitors of miR-499 and/or miR-208b may prevent cardiac hypertrophy and its associated symptoms from arising.

The function of miRNAs may be inhibited by the administration of antagomirs. Initially described by Krützfeldt and colleagues (Krützfeldt et al., 2005), "antagomirs" are single-stranded, chemically-modified ribonucleotides that are at least partially complementary to the miRNA sequence. Antagomirs may comprise one or more modified nucleotides, such as 2'-O-methyl-sugar modifications. In some embodiments, antagomirs comprise only modified nucleotides. Antagomirs may also comprise one or more phosphorothioate linkages resulting in a partial or full phosphorothioate backbone. To facilitate in vivo delivery and stability, the antagomir may be linked to a cholesterol moiety at its 3' end. Antagomirs suitable for inhibiting miRNAs may be about 15 to about 50 nucleotides in length, more preferably about 18 to about 30 nucleotides in length, and most preferably about 20 to about 25 nucleotides in length. "Partially complementary" refers to a sequence that is at least about 75%, 80%, 85%, 90%, 95%, 96%, 97%, 98%, or 99% complementary to a target polynucleotide sequence. The antagomirs may be at least about 75%, 80%, 85%, 90%, 95%, 96%, 97%, 98%, or 99% complementary to a mature miRNA sequence. In some embodiments, the antagomir may be substantially complementary to a mature miRNA sequence, that is at least about 95%, 96%, 97%, 98%, or 99% complementary to a target polynucleotide sequence. In other embodiments, the antagomirs are 100% complementary to the mature miRNA sequence.

Inhibition of microRNA function may also be achieved by administering antisense oligonucleotides targeting the mature miR-499, miR-208, or miR-208b sequences. The antisense oligonucleotides may be ribonucleotides or deoxyribonucleotides. Preferably, the antisense oligonucleotides have at least one chemical modification. Antisense oligonucleotides may be comprised of one or more "locked nucleic acids". "Locked nucleic acids" (LNAs) are modified ribonucleotides that contain an extra bridge between the 2' and 4' carbons of the ribose sugar moiety resulting in a "locked" conformation that confers enhanced thermal stability to oligonucleotides containing the LNAs. Alternatively, the antisense oligonucleotides may comprise peptide nucleic acids (PNAs), which contain a peptide-based backbone rather than a sugar-phosphate backbone. Other chemical modifications that the antisense oligonucleotides may contain include, but are not limited to, sugar modifications, such as 2'-O-alkyl (e.g. 2'-O-methyl, 2'-O-methoxyethyl), 2'-fluoro, and 4' thio modifications, and backbone modifications, such as one or more phosphorothioate, morpholino, or phosphonocarboxylate linkages (see, for example, U.S. Pat. Nos. 6,693,187 and 7,067,641, which are herein incorporated by reference in their entireties). In some embodiments, suitable antisense oligonucleotides are 2'-O-methoxyethyl "gapmers" which contain 2'-O-methoxyethyl-modified ribonucleotides on both 5' and 3' ends with at least ten deoxyribonucleotides in the center. These "gapmers" are capable of triggering RNase H-dependent degradation mechanisms of RNA targets. Other modifications of antisense oligonucleotides to enhance stability and improve efficacy, such as those described in U.S. Pat. No. 6,838,283, which is herein incorporated by reference in its entirety, are known in the art and are suitable for use in the methods of the invention. Preferable antisense oligonucleotides useful for inhibiting the activity of microRNAs are about 19 to about 25 nucleotides in length. Antisense oligonucleotides may comprise a sequence that is at least partially complementary to a mature miRNA sequence, e.g. at least about 75%, 80%, 85%, 90%, 95%, 96%, 97%, 98%, or 99% complementary to a mature miRNA sequence. In some embodiments, the antisense oligonucleotide may be substantially complementary to a mature miRNA sequence, that is at least about 95%, 96%, 97%, 98%, or 99% complementary to a target polynucleotide sequence. In one embodiment, the antisense oligonucleotide comprises a sequence that is 100% complementary to a mature miRNA sequence.

Another approach for inhibiting the function of miR-499, miR-208, and miR-208b is administering an inhibitory RNA molecule having at least partial sequence identity to the mature miR-499, miR-208, and miR-208b sequences. The inhibitory RNA molecule may be a double-stranded, small interfering RNA (siRNA) or a short hairpin RNA molecule (shRNA) comprising a stem-loop structure. The double-stranded regions of the inhibitory RNA molecule may comprise a sequence that is at least partially identical, e.g. about 75%, 80%, 85%, 90%, 95%, 96%, 97%, 98%, or 99% identical, to the mature miRNA sequence. In some embodiments, the double-stranded regions of the inhibitory RNA comprise a sequence that is at least substantially identical to the mature miRNA sequence. "Substantially identical" refers to a sequence that is at least about 95%, 96%, 97%, 98%, or 99% identical to a target polynucleotide sequence. In other embodiments, the double-stranded regions of the inhibitory RNA molecule may contain 100% identity to the target miRNA sequence.

The inhibitory nucleotide molecules described herein preferably target the mature sequence of miR-499 (SEQ ID NO: 26), miR-208 (SEQ ID NO:5), or miR-208b (SEQ ID NO: 27). In some embodiments, inhibitors of miR-499, miR-208, and miR-208b are antagomirs comprising a sequence that is perfectly complementary to the mature miR-499, mature miR-208, or mature miR-208b sequence. In one embodiment, an inhibitor of miR-499 is an antagomir having a sequence that is partially or perfectly complementary to 5'-UUAAGACUUGCAGUGAUGUUU-3' (SEQ ID NO: 26). In another embodiment, an inhibitor of miR-208 is an antagomir having a sequence that is partially or perfectly complementary to 5'-AUAAGACGAGCAAAAAGCUUGU-3' (SEQ ID NO: 5). In another embodiment, an inhibitor of miR-208b is an antagomir having a sequence that is partially or perfectly complementary to 5'-AUAAGACGAACAAAAGGUUUGU (SEQ ID NO:27).

In some embodiments, inhibitors of miR-499, miR-208, and miR-208b are chemically-modified antisense oligonucleotides. In one embodiment, an inhibitor of miR-499 is a chemically-modified antisense oligonucleotide comprising a sequence substantially complementary to 5'-UUAAGACUUGCAGUGAUGUUU-3' (SEQ ID NO: 26). In another embodiment, an inhibitor of miR-208 is a chemically-modified antisense oligonucleotide comprising a sequence substantially complementary to 5'-AUAAGACGAGCAAAAAGCUUGU-3' (SEQ ID NO: 5). In another embodiment, an inhibitor of miR-208b is a chemically-modified antisense oligonucleotide comprising a sequence substantially complementary to 5'-AUAAGACGAACAAAAGGUUUGU (SEQ ID NO:27). As used herein "substantially complementary" refers to a sequence that is at least about 95%, 96%, 97%, 98%, 99%, or 100% complementary to a target polynucleotide sequence (e.g. mature or precursor miRNA sequence).

Antisense oligonucleotides may comprise a sequence that is substantially complementary to a precursor miRNA sequence (pre-miRNA) for miR-499, miR-208, or miR-208b. In some embodiments, the antisense oligonucleotide comprises a sequence that is substantially complementary to a sequence located outside the stem-loop region of the pre-miR-499, pre-miR-208, or pre-miR-208b sequence. In one embodiment, an inhibitor of miR-499 function is an antisense oligonucleotide having a sequence that is substantially complementary to a pre-miR-499 sequence selected from the group consisting of SEQ ID NO:18, SEQ ID NO:19, SEQ ID NO:20, SEQ ID NO:21, SEQ ID NO:22, SEQ ID NO:23 and SEQ ID NO:24. In another embodiment, an inhibitor of miR-208 function is an antisense oligonucleotide having a sequence that is substantially complementary to a pre-miR-208 sequence selected from the group consisting of SEQ ID NO:14, SEQ ID NO:15, SEQ ID NO:16, and SEQ ID NO:17. In still another embodiment, an inhibitor of miR-208b function is an antisense oligonucleotide having a sequence that is substantially complementary to a pre-miR-208b sequence selected from the group consisting of SEQ ID NO: 30, SEQ ID NO:31, SEQ ID NO:32, SEQ ID NO:33, SEQ ID NO:34, and SEQ ID NO: 35.

In other embodiments of the invention, inhibitors of miR-499, miR-208, and miR-208b may be inhibitory RNA molecules, such as ribozymes, siRNAs, or shRNAs. In one embodiment, an inhibitor of miR-499 is an inhibitory RNA molecule comprising a double-stranded region, wherein the double-stranded region comprises a sequence having 100% identity to the mature miR-499 sequence (SEQ ID NO: 26). In another embodiment, an inhibitor of miR-208 is an inhibitory RNA molecule comprising a double-stranded region, wherein the double-stranded region comprises a sequence having 100% identity to the mature miR-208 sequence (SEQ ID NO: 5). In another embodiment, an inhibitor of miR-208b is an inhibitory RNA molecule comprising a double-stranded region, wherein the double-stranded region comprises a sequence having 100% identity to the mature miR-208b sequence (SEQ ID NO: 27). In some embodiments, inhibitors of miR-208, miR-208b, and miR-499 function are inhibitory RNA molecules which comprise a double-stranded region, wherein said double-stranded region comprises a sequence of at least about 75%, 80%, 85%, 90%, 95%, 96%, 97%, 98%, or 99% identity to the mature miR-208, miR-208b, or miR-499 sequence.

The present invention also contemplates methods for scavenging or clearing miR-499 and/or miR-208b antagonists following treatment. The method may comprise overexpressing binding sites for the miR-499 and/or miR-208b antagonists in cardiac tissue. In another embodiment, the present invention provides a method for scavenging or clearing miR-499 and/or miR-208b following treatment. In one embodiment, the method comprises overexpression of binding site regions for miR-499 and/or miR-208b in skeletal muscle using a skeletal and heart muscle specific promoter (muscle creatine kinase (MCK)). The binding site regions preferably contain a sequence of the seed region for miR-499 and/or miR-208b. In some embodiments, the binding site may contain a sequence from the 3'UTR of one or more targets of miR-499 or miR-208b, such as THRAP1 or PURbeta. In another embodiment, a miR-499 and/or miR-208b antagonist may be administered after miR-499 and/or miR-208b to attenuate or stop the function of the microRNA.

Combined Therapy

In another embodiment of the invention, it is envisioned to use an inhibitor of miR-499 or miR-208b in combination with other therapeutic modalities. Current medical management of cardiac hypertrophy in the setting of a cardiovascular disorder includes the use of at least two types of drugs inhibitors of the renin-angiotensin system, and β-adrenergic blocking agents (Bristow, 1999). Therapeutic agents to treat pathologic hypertrophy in the setting of heart failure include angiotensin II converting enzyme (ACE) inhibitors and β-adrenergic receptor blocking agents (Eichhorn and Bristow, 1996). Other pharmaceutical agents that have been disclosed for treatment of cardiac hypertrophy include angiotensin II receptor antagonists (U.S. Pat. No. 5,604,251) and neuropeptide Y antagonists (WO 98/33791).

Non-pharmacological treatment is primarily used as an adjunct to pharmacological treatment. One means of non-pharmacological treatment involves reducing the sodium in the diet. In addition, non-pharmacological treatment also entails the elimination of certain precipitating drugs, including negative inotropic agents (e.g., certain calcium channel blockers and antiarrhythmic drugs like disopyramide), cardiotoxins (e.g., amphetamines), and plasma volume expanders (e.g., nonsteroidal anti-inflammatory agents and glucocorticoids).

Thus, in addition to the therapies described above, one may also provide to the subject more "standard" pharmaceutical cardiac therapies with the inhibitor of miR-499 and/or miR-208b. Examples of other therapies include, without limitation, so-called "beta blockers," anti-hypertensives, cardiotonics, anti-thrombotics, vasodilators, hormone antagonists, iontropes, diuretics, endothelin receptor antagonists, calcium channel blockers, phosphodiesterase inhibitors, ACE inhibitors, angiotensin type 2 antagonists and cytokine blockers/inhibitors, and HDAC inhibitors. The combination therapy also may involve inhibiting the expression or activity of both miR-499 and miR-208b, or inhibiting the expression or activity of miR-208, and/or additional miRNAs involved in cardiac remodeling such as miR-21 and miR-195. Combination therapy may also include overexpression of particular microRNAs, such as miR-29.

Combinations may be achieved by contacting cardiac cells with a single composition or pharmacological formulation that includes an inhibitor of miR-499 or miR-208b and a standard pharmaceutical agent, or by contacting the cell with two distinct compositions or formulations, at the same time, wherein one composition includes an inhibitor of miR-499 or miR-208b and the other includes the standard pharmaceutical agent. Alternatively, the therapy using an inhibitor of miR-499 and/or miR-208b may precede or follow administration of the other agent(s) by intervals ranging from minutes to weeks. In embodiments where the standard pharmaceutical agent and miR-499 or miR-208b inhibitor are applied separately to the cell, one would generally ensure that a significant period of time did not expire between the time of each delivery, such that the pharmaceutical agent and miR-499 or miR-208b inhibitor would still be able to exert an advantageously combined effect on the cell. In such instances, it is contemplated that one would typically contact the cell with both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either an inhibitor of miR-499 and/or miR-208b, or the other pharmaceutical agent will be desired. In this regard, various combinations may be employed. By way of illustration, where the inhibitor of miR-499 or miR-208b is "A" and the other agent is "B", the following permutations based on 3 and 4 total administrations are exemplary:

A/B/A B/A/B B/B/A A/A/B B/A/A A/B/B B/B/B/A B/B/A/B
A/A/B/B A/B/A/B A/B/B/A B/B/A/A B/A/B/A B/A/A/B B/B/B/A
A/A/A/B B/A/A/A A/B/A/A A/A/B/A A/B/B/B B/A/B/B B/B/A/B

Other combinations are likewise contemplated.

Treatment regimens would vary depending on the clinical situation. However, long-term maintenance would appear to be appropriate in most circumstances. It also may be desirable to treat hypertrophy with inhibitors of miR-499 and/or miR-208b intermittently, such as within a brief window during disease progression.

Pharmacological therapeutic agents and methods of administration, dosages, etc., are well known to those of skill in the art (see for example, the "Physicians Desk Reference", Klaassen's "The Pharmacological Basis of Therapeutics", "Remington's Pharmaceutical Sciences", and "The Merck Index, Eleventh Edition", incorporated herein by reference in relevant parts), and may be combined with the invention in light of the disclosures herein. Some variation in dosage will necessarily occur depending on the condition of the subject being treated. The person responsible for administration will, in any event, determine the appropriate dose for the individual subject, and such individual determinations are within the skill of those of ordinary skill in the art.

Non-limiting examples of a pharmacological therapeutic agent that may be used in the present invention include an antihyperlipoproteinemic agent, an antiarteriosclerotic agent, an antithrombotic/fibrinolytic agent, a blood coagulant, an antiarrhythmic agent, an antihypertensive agent, a vasopressor, a treatment agent for congestive heart failure, an antianginal agent, an antibacterial agent or a combination thereof.

In addition, it should be noted that any of the following may be used to develop new sets of cardiac therapy target genes as β-blockers were used in the present examples (see below). While it is expected that many of these genes may overlap, new gene targets likely can be developed.

In certain embodiments, administration of an agent that lowers the concentration of one of more blood lipids and/or lipoproteins, known herein as an "antihyperlipoproteinemic," may be combined with a cardiovascular therapy according to the present invention, particularly in treatment of atherosclerosis and thickenings or blockages of vascular tissues. In certain embodiments, an antihyperlipoproteinemic agent may comprise an aryloxyalkanoic/fibric acid derivative, a resin/bile acid sequesterant, a HMG CoA reductase inhibitor, a nicotinic acid derivative, a thyroid hormone or thyroid hormone analog, a miscellaneous agent or a combination thereof.

Non-limiting examples of aryloxyalkanoic/fibric acid derivatives include beclobrate, enzafibrate, binifibrate, ciprofibrate, clinofibrate, clofibrate (atromide-S), clofibric acid, etofibrate, fenofibrate, gemfibrozil (lobid), nicofibrate, pirifibrate, ronifibrate, simfibrate and theofibrate.

Non-limiting examples of resins/bile acid sequesterants include cholestyramine (cholybar, questran), colestipol (colestid) and polidexide.

Non-limiting examples of HMG CoA reductase inhibitors include lovastatin (mevacor), pravastatin (pravochol) or simvastatin (zocor).

Non-limiting examples of nicotinic acid derivatives include nicotinate, acepimox, niceritrol, nicoclonate, nicomol and oxiniacic acid.

Non-limiting examples of thyroid hormones and analogs thereof include etoroxate, thyropropic acid and thyroxine.

Non-limiting examples of miscellaneous antihyperlipoproteinemics include acifran, azacosterol, benfluorex, β-benzalbutyramide, carnitine, chondroitin sulfate, clomestrone, detaxtran, dextran sulfate sodium, 5, 8, 11, 14, 17-eicosapentaenoic acid, eritadenine, furazabol, meglutol, melinamide, mytatrienediol, ornithine, γ-oryzanol, pantethine, pentaerythritol tetraacetate, α-phenylbutyramide, pirozadil, probucol (lorelco), β-sitosterol, sultosilic acid-piperazine salt, tiadenol, triparanol and xenbucin.

Non-limiting examples of an antiarteriosclerotic include pyridinol carbamate.

In certain embodiments, administration of an agent that aids in the removal or prevention of blood clots may be combined with administration of a modulator, particularly in treatment of atherosclerosis and vasculature (e.g., arterial) blockages. Non-limiting examples of antithrombotic and/or fibrinolytic agents include anticoagulants, anticoagulant antagonists, antiplatelet agents, thrombolytic agents, thrombolytic agent antagonists or combinations thereof.

In certain embodiments, antithrombotic agents that can be administered orally, such as, for example, aspirin and wafarin (coumadin), are preferred.

Non-limiting examples of anticoagulants include acenocoumarol, ancrod, anisindione, bromindione, clorindione, coumetarol, cyclocumarol, dextran sulfate sodium, dicumarol, diphenadione, ethyl biscoumacetate, ethylidene dicoumarol, fluindione, heparin, hirudin, lyapolate sodium, oxazidione, pentosan polysulfate, phenindione, phenprocoumon, phosvitin, picotamide, tioclomarol and warfarin.

Non-limiting examples of antiplatelet agents include aspirin, a dextran, dipyridamole (persantin), heparin, sulfinpyranone (anturane) and ticlopidine (ticlid).

Non-limiting examples of thrombolytic agents include tissue plaminogen activator (activase), plasmin, pro-urokinase, urokinase (abbokinase) streptokinase (streptase), anistreplase/APSAC (eminase).

In certain embodiments wherein a subject is suffering from a hemorrhage or an increased likelihood of hemorrhaging, an agent that may enhance blood coagulation may be used. Non-limiting examples of a blood coagulation promoting agents include thrombolytic agent antagonists and anticoagulant antagonists.

Non-limiting examples of anticoagulant antagonists include protamine and vitamine K1.

Non-limiting examples of thrombolytic agent antagonists include amiocaproic acid (amicar) and tranexamic acid (amstat). Non-limiting examples of antithrombotics include anagrelide, argatroban, cilstazol, daltroban, defibrotide, enoxaparin, fraxiparine, indobufen, lamoparan, ozagrel, picotamide, plafibride, tedelparin, ticlopidine and triflusal.

Non-limiting examples of antiarrhythmic agents include Class I antiarrhythmic agents (sodium channel blockers), Class II antiarrhythmic agents (beta-adrenergic blockers), Class III antiarrhythmic agents (repolarization prolonging drugs), Class IV antiarrhythmic agents (calcium channel blockers) and miscellaneous antiarrhythmic agents.

Non-limiting examples of sodium channel blockers include Class IA, Class IB and Class IC antiarrhythmic agents. Non-limiting examples of Class IA antiarrhythmic agents include disppyramide (norpace), procainamide (pronestyl) and quinidine (quinidex). Non-limiting examples of Class IB antiarrhythmic agents include lidocaine (xylocalne), tocamide (tonocard) and mexiletine (mexitil). Non-limiting examples of Class IC antiarrhythmic agents include encamide (enkaid) and flecamide (tambocor).

Non-limiting examples of a beta blocker, otherwise known as a β-adrenergic blocker, a β-adrenergic antagonist or a Class II antiarrhythmic agent, include acebutolol (sectral), alprenolol, amosulalol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol (brevibloc), indenolol, labetalol, levobunolol, mepindolol, metipranolol, metoprolol, moprolol, nadolol, nadoxolol, nifenalol, nipradilol, oxprenolol, penbutolol, pindolol, practolol, pronethalol, propanolol (inderal), sotalol (betapace), sulfinalol, talinolol, tertatolol, timolol, toliprolol and xibinolol. In certain embodiments, the beta blocker comprises an aryloxypropanolamine derivative. Non-limiting examples of aryloxypropanolamine derivatives include acebutolol, alprenolol, arotinolol, atenolol, betaxolol, bevantolol, bisoprolol, bopindolol, bunitrolol, butofilolol, carazolol, carteolol, carvedilol, celiprolol, cetamolol, epanolol, indenolol, mepindolol, metipranolol, metoprolol, moprolol, nadolol, nipradilol, oxprenolol, penbutolol, pindolol, propanolol, talinolol, tertatolol, timolol and toliprolol.

Non-limiting examples of an agent that prolong repolarization, also known as a Class III antiarrhythmic agent, include amiodarone (cordarone) and sotalol (betapace).

Non-limiting examples of a calcium channel blocker, otherwise known as a Class IV antiarrhythmic agent, include an arylalkylamine (e.g., bepridile, diltiazem, fendiline, gallopamil, prenylamine, terodiline, verapamil), a dihydropyridine derivative (felodipine, isradipine, nicardipine, nifedipine, nimodipine, nisoldipine, nitrendipine) a piperazinde derivative (e.g., cinnarizine, flunarizine, lidoflazine) or a micellaneous calcium channel blocker such as bencyclane, etafenone, magnesium, mibefradil or perhexyline. In certain embodiments a calcium channel blocker comprises a long-acting dihydropyridine (nifedipine-type) calcium antagonist.

Non-limiting examples of miscellaneous antiarrhythmic agents include adenosine (adenocard), digoxin (lanoxin), acecamide, ajmaline, amoproxan, aprindine, bretylium tosylate, bunaftine, butobendine, capobenic acid, cifenline, disopyranide, hydroquinidine, indecamide, ipatropium bromide, lidocaine, lorajmine, lorcamide, meobentine, moricizine, pirmenol, prajmaline, propafenone, pyrinoline, quinidine polygalacturonate, quinidine sulfate and viquidil.

Non-limiting examples of antihypertensive agents include sympatholytic, alpha/beta blockers, alpha blockers, anti-angiotensin II agents, beta blockers, calcium channel blockers, vasodilators and miscellaneous antihypertensives.

Non-limiting examples of an alpha blocker, also known as an α-adrenergic blocker or an α-adrenergic antagonist, include amosulalol, arotinolol, dapriprazole, doxazosin, ergoloid mesylates, fenspiride, indoramin, labetalol, nicergoline, prazosin, terazosin, tolazoline, trimazosin and yohimbine. In certain embodiments, an alpha blocker may comprise a quinazoline derivative. Non-limiting examples of quinazoline derivatives include alfuzosin, bunazosin, doxazosin, prazosin, terazosin and trimazosin.

In certain embodiments, an antihypertensive agent is both an alpha and beta adrenergic antagonist. Non-limiting examples of an alpha/beta blocker comprise labetalol (normodyne, trandate).

Non-limiting examples of anti-angiotensin II agents include angiotensin converting enzyme inhibitors and angiotensin II receptor antagonists. Non-limiting examples of angiotensin converting enzyme inhibitors (ACE inhibitors) include alacepril, enalapril (vasotec), captopril, cilazapril, delapril, enalaprilat, fosinopril, lisinopril, moveltopril, perindopril, quinapril and ramipril. Non-limiting examples of an angiotensin II receptor blocker, also known as an angiotensin II receptor antagonist, an ANG receptor blocker or an ANG-II type-1 receptor blocker (ARBS), include angiocandesartan, eprosartan, irbesartan, losartan and valsartan.

Non-limiting examples of a sympatholytic include a centrally acting sympatholytic or a peripherially acting sympatholytic. Non-limiting examples of a centrally acting sympatholytic, also known as an central nervous system (CNS) sympatholytic, include clonidine (catapres), guanabenz (wytensin) guanfacine (tenex) and methyldopa (aldomet). Non-limiting examples of a peripherally acting sympatholytic include a ganglion blocking agent, an adrenergic neuron blocking agent, a β-adrenergic blocking agent or a alpha1-adrenergic blocking agent. Non-limiting examples of a ganglion blocking agent include mecamylamine (inversine) and trimethaphan (arfonad). Non-limiting examples of an adrenergic neuron blocking agent include guanethidine (ismelin) and reserpine (serpasil). Non-limiting examples of a β-adrenergic blocker include acenitolol (sectral), atenolol (tenormin), betaxolol (kerlone), carteolol (cartrol), labetalol (normodyne, trandate), metoprolol (lopressor), nadanol (corgard), penbutolol (levatol), pindolol (visken), propranolol (inderal) and timolol (blocadren). Non-limiting examples of alpha1-adrenergic blocker include prazosin (minipress), doxazocin (cardura) and terazosin (hytrin).

In certain embodiments a cardiovasculator therapeutic agent may comprise a vasodilator (e.g., a cerebral vasodilator, a coronary vasodilator or a peripheral vasodilator). In certain preferred embodiments, a vasodilator comprises a coronary vasodilator. Non-limiting examples of a coronary vasodilator include amotriphene, bendazol, benfurodil hemisuccinate, benziodarone, chloracizine, chromonar, clobenfurol, clonitrate, dilazep, dipyridamole, droprenilamine, efloxate, erythrityl tetranitrane, etafenone, fendiline, floredil, ganglefene, herestrol bis(β-diethylaminoethyl ether), hexobendine, itramin tosylate, khellin, lidoflanine, mannitol hexanitrane, medibazine, nicorglycerin, pentaerythritol tetranitrate, pentrinitrol, perhexyline, pimethylline, trapidil, tricromyl, trimetazidine, trolnitrate phosphate and visnadine.

In certain embodiments, a vasodilator may comprise a chronic therapy vasodilator or a hypertensive emergency vasodilator. Non-limiting examples of a chronic therapy vasodilator include hydralazine (apresoline) and minoxidil (loniten). Non-limiting examples of a hypertensive emergency vasodilator include nitroprusside (nipride), diazoxide (hyperstat IV), hydralazine (apresoline), minoxidil (loniten) and verapamil.

Non-limiting examples of miscellaneous antihypertensives include ajmaline, γ-aminobutyric acid, bufeniode, cicletainine, ciclosidomine, a cryptenamine tannate, fenoldopam, flosequinan, ketanserin, mebutamate, mecamylamine, methyldopa, methyl 4-pyridyl ketone thiosemicarbazone, muzolimine, pargyline, pempidine, pinacidil, piperoxan, primaperone, a protoveratrine, raubasine, rescimetol, rilmenidene, saralasin, sodium nitrorusside, ticrynafen, trimethaphan camsylate, tyrosinase and urapidil.

In certain embodiments, an antihypertensive may comprise an arylethanolamine derivative, a benzothiadiazine derivative, a N-carboxyalkyl(peptide/lactam) derivative, a dihydropyridine derivative, a guanidine derivative, a hydrazines/phthalazine, an imidazole derivative, a quanternary ammonium compound, a reserpine derivative or a suflonamide derivative.

Non-limiting examples of arylethanolamine derivatives include amosulalol, bufuralol, dilevalol, labetalol, pronethalol, sotalol and sulfinalol.

Non-limiting examples of benzothiadiazine derivatives include althizide, bendroflumethazide, benzthiazide, benzylhydrochlorothiazide, buthiazide, chlorothiazide, chlorthalidone, cyclopenthiazide, cyclothiazide, diazoxide, epithiazide, ethiazide, fenquizone, hydrochlorothizide, hydroflumethizide, methyclothiazide, meticrane, metolazone, paraflutizide, polythizide, tetrachlormethiazide and trichlormethiazide.

Non-limiting examples of N-carboxyalkyl(peptide/lactam) derivatives include alacepril, captopril, cilazapril, delapril, enalapril, enalaprilat, fosinopril, lisinopril, moveltipril, perindopril, quinapril and ramipril.

Non-limiting examples of dihydropyridine derivatives include amlodipine, felodipine, isradipine, nicardipine, nifedipine, nilvadipine, nisoldipine and nitrendipine.

Non-limiting examples of guanidine derivatives include bethanidine, debrisoquin, guanabenz, guanacline, guanadrel, guanazodine, guanethidine, guanfacine, guanochlor, guanoxabenz and guanoxan.

Non-limiting examples of hydrazines/phthalazines include budralazine, cadralazine, dihydralazine, endralazine, hydracarbazine, hydralazine, pheniprazine, pildralazine and todralazine.

Non-limiting examples of imidazole derivatives include clonidine, lofexidine, phentolamine, tiamenidine and tolonidine.

Non-limiting examples of quanternary ammonium compounds include azamethonium bromide, chlorisondamine chloride, hexamethonium, pentacynium bis(methylsulfate), pentamethonium bromide, pentolinium tartrate, phenactropinium chloride and trimethidinium methosulfate.

Non-limiting examples of reserpine derivatives include bietaserpine, deserpidine, rescinnamine, reserpine and syrosingopine.

Non-limiting examples of sulfonamide derivatives include ambuside, clopamide, furosemide, indapamide, quinethazone, tripamide and xipamide.

Vasopressors generally are used to increase blood pressure during shock, which may occur during a surgical procedure. Non-limiting examples of a vasopressor, also known as an antihypotensive, include amezinium methyl sulfate, angiotensin amide, dimetofrine, dopamine, etifelmin, etilefrin, gepefrine, metaraminol, midodrine, norepinephrine, pholedrine and synephrine.

Non-limiting examples of agents for the treatment of congestive heart failure include anti-angiotensin II agents, afterload-preload reduction treatment, diuretics and inotropic agents.

In certain embodiments, an animal subject that can not tolerate an angiotensin antagonist may be treated with a combination therapy. Such therapy may combine administration of hydralazine (apresoline) and isosorbide dinitrate (isordil, sorbitrate).

Non-limiting examples of a diuretic include a thiazide or benzothiadiazine derivative (e.g., althiazide, bendroflumethazide, benzthiazide, benzylhydrochlorothiazide, buthiazide, chlorothiazide, chlorothiazide, chlorthalidone, cyclopenthiazide, epithiazide, ethiazide, ethiazide, fenquizone, hydrochlorothiazide, hydroflumethiazide, methyclothiazide, meticrane, metolazone, paraflutizide, polythizide, tetrachloromethiazide, trichlormethiazide), an organomercurial (e.g., chlormerodrin, meralluride, mercamphamide, mercaptomerin sodium, mercumallylic acid, mercumatilin dodium, mercurous chloride, mersalyl), a pteridine (e.g., furtherene, triamterene), purines (e.g., acefylline, 7-morpholinomethyltheophylline, pamobrom, protheobromine, theobromine), steroids including aldosterone antagonists (e.g., canrenone, oleandrin, spironolactone), a sulfonamide derivative (e.g., acetazolamide, ambuside, azosemide, bumetanide, butazolamide, chloraminophenamide, clofenamide, clopamide, clorexolone, diphenylmethane-4,4'-disulfonamide, disulfamide, ethoxzolamide, furosemide, indapamide, mefruside, methazolamide, piretanide, quinethazone, torasemide, tripamide, xipamide), a uracil (e.g., aminometradine, amisometradine), a potassium sparing antagonist (e.g., amiloride, triamterene) or a miscellaneous diuretic such as aminozine, arbutin, chlorazanil, ethacrynic acid, etozolin, hydracarbazine, isosorbide, mannitol, metochalcone, muzolimine, perhexyline, ticrnafen and urea.

Non-limiting examples of a positive inotropic agent, also known as a cardiotonic, include acefylline, an acetyldigitoxin, 2-amino-4-picoline, aminone, benfurodil hemisuccinate, bucladesine, cerberosine, camphotamide, convallatoxin, cymarin, denopamine, deslanoside, digitalin, digitalis, digitoxin, digoxin, dobutamine, dopamine, dopexamine, enoximone, erythrophleine, fenalcomine, gitalin, gitoxin, glycocyamine, heptaminol, hydrastinine, ibopamine, a lanatoside, metamivam, milrinone, nerifolin, oleandrin, ouabain, oxyfedrine, prenalterol, proscillaridine, resibufogenin, scillaren, scillarenin, strphanthin, sulmazole, theobromine and xamoterol.

In particular embodiments, an intropic agent is a cardiac glycoside, a beta-adrenergic agonist or a phosphodiesterase inhibitor. Non-limiting examples of a cardiac glycoside includes digoxin (lanoxin) and digitoxin (crystodigin). Non-limiting examples of a β-adrenergic agonist include albuterol, bambuterol, bitolterol, carbuterol, clenbuterol, clorprenaline, denopamine, dioxethedrine, dobutamine (dobutrex), dopamine (intropin), dopexamine, ephedrine, etafedrine, ethylnorepinephrine, fenoterol, formoterol, hexoprenaline, ibopamine, isoetharine, isoproterenol, mabuterol, metaproterenol, methoxyphenamine, oxyfedrine, pirbuterol, procaterol, protokylol, reproterol, rimiterol, ritodrine, soterenol, terbutaline, tretoquinol, tulobuterol and xamoterol. Non-limiting examples of a phosphodiesterase inhibitor include aminone (inocor).

Antianginal agents may comprise organonitrates, calcium channel blockers, beta blockers and combinations thereof.

Non-limiting examples of organonitrates, also known as nitrovasodilators, include nitroglycerin (nitro-bid, nitrostat), isosorbide dinitrate (isordil, sorbitrate) and amyl nitrate (aspirol, vaporole).

Endothelin (ET) is a 21-amino acid peptide that has potent physiologic and pathophysiologic effects that appear to be involved in the development of heart failure. The effects of ET are mediated through interaction with two classes of cell surface receptors. The type A receptor (ET-A) is associated with vasoconstriction and cell growth while the type B receptor (ET-B) is associated with endothelial-cell mediated vasodilation and with the release of other neurohormones, such as aldosterone. Pharmacologic agents that can inhibit either the production of ET or its ability to stimulate relevant cells are known in the art. Inhibiting the production of ET involves the use of agents that block an enzyme termed endothelin-converting enzyme that is involved in the processing of the active peptide from its precursor. Inhibiting the ability of ET to stimulate cells involves the use of agents that block the interaction of ET with its receptors. Non-limiting examples of endothelin receptor antagonists (ERA) include Bosentan, Enrasentan, Ambrisentan, Darusentan, Tezosentan, Atrasentan, Avosentan, Clazosentan, Edonentan, sitaxsentan, TBC 3711, BQ 123, and BQ 788.

In certain embodiments, the secondary therapeutic agent may comprise a surgery of some type, which includes, for example, preventative, diagnostic or staging, curative and palliative surgery. Surgery, and in particular a curative surgery, may be used in conjunction with other therapies, such as the present invention and one or more other agents.

Such surgical therapeutic agents for vascular and cardiovascular diseases and disorders are well known to those of skill in the art, and may comprise, but are not limited to, performing cardiovascular surgery on an organism, providing a cardiovascular mechanical prostheses, angioplasty, coronary artery reperfusion, catheter ablation, providing an implantable cardioverter defibrillator to the subject, mechanical circulatory support or a combination thereof. Non-limiting examples of a mechanical circulatory support that may be used in the present invention comprise an intra-aortic balloon counterpulsation, left ventricular assist device or combination thereof.

Methods of Treating Musculoskeletal Diseases

The present invention also provides a method of decreasing the expression or activity of a fast skeletal muscle contractile protein gene in skeletal muscle cells. In one embodiment, the method comprises administering miR-499 and/or miR-208b to the skeletal muscle cells.

The up-regulation of several fast skeletal muscle contractile protein genes was observed in the hearts of mice lacking both miR-208 alleles. This up-regulation of fast skeletal muscle contractile protein genes in the hearts of miR-208 knockout mice indicates that miR-208 normally functions to repress the fast skeletal muscle gene program. A concomitant reduction of miR-499 expression was observed in miR-208 mutant mice, suggesting that miR-499 may also negatively regulate the expression of fast skeletal muscle contractile protein genes. MiR-208b, which is encoded by an intron of the β-MHC gene, differs from miR-208 by only three bases and is expressed solely in heart and slow skeletal muscle. Thus, miR-208b may also regulate the fast skeletal muscle gene program and determine fiber identity.

In skeletal muscle, the repression of slow fiber genes and activation of fast fiber genes is associated with numerous musculoskeletal disorders, including, but not limited to, disuse atrophy, muscle wasting in response to anti-gravity, and denervation. Thus, expression of miR-208, miR-208b, or miR-499 in skeletal muscle cells may be useful in repressing fast fiber genes and thereby activating the reciprocal expression of slow fiber genes. Accordingly, the present invention also encompasses a method for treating or preventing a musculoskeletal disorder in a subject in need thereof. In one embodiment, the method comprises identifying a subject having or at risk of a musculoskeletal disorder and increasing the expression and/or activity of miR-499 and/or miR-208b in skeletal muscle cells of said subject. In some embodiments, increasing the expression and/or activity of miR-499 and/or miR-208b may comprise administering an agonist of miR-499 and/or miR-208b to the skeletal muscle of a subject who has, or is at risk for developing, a musculoskeletal disorder. In another embodiment, the present invention provides methods of treating or preventing muscle wasting in response to a reduced gravity environment by administering an agonist of miR-499 and/or miR-208b to the skeletal muscle. In another embodiment, the present invention provides methods of treating or preventing muscle atrophy by administering miR-499 or miR-208b to the skeletal muscle.

In addition, the results shown herein suggest that strategies to enhance slow fiber gene expression by elevating miR-499 or miR-208b expression can be used to augment insulin sensitivity. Skeletal muscle accounts for the majority of insulin-stimulated glucose uptake in humans. Insulin resistance is a deficiency of insulin-stimulated glucose uptake seen in patients with type II diabetes mellitus. There is a positive correlation of insulin resistance and the percentage of slow- versus fast-twitch muscle fibers. Thus, in another embodiment, the present invention contemplates a method of augmenting insulin sensitivity in skeletal muscle comprising increasing the expression and/or activity of miR-499 and/or miR-208b in skeletal muscle cells.

In some embodiments of the invention, increasing the expression or activity of miR-499 or miR-208b in a cell may comprise administering an agonist of miR-499 or miR-208b. In one embodiment, an agonist of miR-499 or miR-208b may be a polynucleotide comprising the mature miR-499 or miR-208b sequence. In another embodiment, the polynucleotide comprises the sequence of SEQ ID NO: 26 or SEQ ID NO: 27. In another embodiment, the agonist of miR-499 or miR-208b may be a polynucleotide comprising the pri-miRNA or pre-miRNA sequence for miR-499 or miR-208b. The polynucleotide comprising the mature miR-499 or miR-208b sequence may be single stranded or double stranded. The polynucleotides may contain one or more chemical modifications, such as locked nucleic acids, peptide nucleic acids, sugar modifications, such as 2'-O-alkyl (e.g. 2'-O-methyl, 2'-O-methoxyethyl), 2'-fluoro, and 4' thio modifications, and backbone modifications, such as one or more phosphorothioate, morpholino, or phosphonocarboxylate linkages. In one embodiment, the polynucleotide comprising a miR-499 or miR-208b sequence is conjugated to cholesterol. In another embodiment, the agonist of miR-499 or miR-208b may be an agent distinct from miR-499 or miR-208b that acts to increase, supplement, or replace the function of miR-499 and/or miR-208b.

In another embodiment, the agonist of miR-499 or miR-208b may be expressed in vivo from a vector. A "vector" is a composition of matter which can be used to deliver a nucleic acid of interest to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. Examples of viral vectors include, but are not limited to, adenoviral vectors, adeno-associated virus vectors, retroviral vectors, and the like. An expression construct can be replicated in a living cell, or it can be made synthetically. For purposes of this application, the terms "expression construct," "expression vector," and "vector," are used interchangeably to demonstrate the application of the invention in a general, illustrative sense, and are not intended to limit the invention.

In one embodiment, an expression vector for expressing miR-499 or miR-208b comprises a promoter "operably linked" to a polynucleotide encoding miR-499 or miR-208b. The phrase "operably linked" or "under transcriptional control" as used herein means that the promoter is in the correct location and orientation in relation to a polynucleotide to control the initiation of transcription by RNA polymerase and expression of the polynucleotide. The polynucleotide encoding miR-499 may encode the primary-microRNA-499 sequence (pri-miR-499), the precursor-microRNA-499 sequence (pre-miR-499) or the mature miR-499 sequence. The polynucleotide encoding miR-208b may encode the primary-microRNA-208b sequence (pri-miR-208b), the precursor-microRNA-208b sequence (pre-miR-208b) or the mature miR-208b sequence. In some embodiments, the expression vector comprises a polynucleotide operably linked to a promoter, wherein said polynucleotide comprises the sequence of SEQ ID NO: 26 or SEQ ID NO: 27. The polynucleotide comprising the sequence of SEQ ID NO: 26 or SEQ ID NO: 27 may be about 18 to about 2000 nucleotides in length, about 70 to about 200 nucleotides in length, about 20 to about 50 nucleotides in length, or about 18 to about 25 nucleotides in length. In other embodiments, the polynucleotide encoding miR-499 or miR-208b is located in a nucleic acid encoding an intron or in a nucleic acid encoding an untranslated region of an mRNA or in a non-coding RNA. In one embodiment, the expression construct may contain sequences from the $20^{th}$ intron from the Myh7b gene. In another embodiment, the expression construct may contain sequences from the $31^{st}$ intron from the Myh7 (β-MHC) gene.

In another embodiment, an expression vector may be used to deliver an inhibitor of miR-499 and/or miR-208b to a cell or subject. An expression vector for expressing an inhibitor of miR-499 or miR-208b comprises a promoter operably linked to a polynucleotide encoding an antisense oligonucleotide, wherein the sequence of the expressed antisense oligonucleotide is partially or perfectly complementary to the mature miR-499 or miR-208b sequence. In yet another embodiment, an expression vector for expressing an inhibitor of miR-499 or miR-208b comprises one or more promoters operably linked to a polynucleotide encoding a shRNA or siRNA, wherein the expressed shRNA or siRNA comprises a sequence that is identical or partially identical to the mature miR-499 or miR-208b sequence. "Partially identical" refers to a sequence that is at least about 75%, 80%, 85%, 90%, 95%, 96%, 97%, 98%, or 99% identical to a target polynucleotide sequence.

Throughout this application, the term "expression construct" is meant to include any type of genetic construct containing a nucleic acid coding for a gene product in which part or all of the nucleic acid encoding sequence is capable of being transcribed. The transcript may be translated into a protein, but it need not be. In some embodiments, expression only includes transcription of the nucleic acid encoding a gene of interest.

In certain embodiments, the nucleic acid encoding a the polynucleotide of interest is under transcriptional control of a promoter. A "promoter" refers to a DNA sequence recognized by the synthetic machinery of the cell, or introduced synthetic machinery, required to initiate the specific transcription of a gene. The term promoter will be used here to refer to a group of transcriptional control modules that are clustered around the initiation site for a RNA polymerase. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7-20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

In other embodiments, the human cytomegalovirus (CMV) immediate early gene promoter, the SV40 early promoter, the Rous sarcoma virus long terminal repeat, rat insulin promoter, RNA pol III promoter, and glyceraldehyde-3-phosphate dehydrogenase promoter can be used to obtain high-level expression of the polynucleotide of interest. The use of other viral or mammalian cellular or bacterial phage promoters which are well-known in the art to achieve expression of a polynucleotide of interest is contemplated as well, provided that the levels of expression are sufficient for a given purpose.

By employing a promoter with well-known properties, the level and pattern of expression of the polynucleotide of interest following transfection or transformation can be optimized. Further, selection of a promoter that is regulated in response to specific physiologic signals can permit inducible expression of the gene product. Tables 1 and 2 list several regulatory elements that may be employed, in the context of the present invention, to regulate the expression of the gene of interest. This list is not intended to be exhaustive of all the possible elements involved in the promotion of gene expression but, merely, to be exemplary thereof.

Enhancers are genetic elements that increase transcription from a promoter located at a distant position on the same molecule of DNA. Enhancers are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of viral promoters, cellular promoters/enhancers and inducible promoters/enhancers that could be used in combination with the nucleic acid encoding a gene of interest in an expression construct (Table 1 and Table 2). Additionally, any promoter/enhancer combination (as per the Eukaryotic Promoter Data Base EPDB) could also be used to drive expression of the gene. Eukaryotic cells can support cytoplasmic transcription from certain bacterial promoters if the appropriate bacterial polymerase is provided, either as part of the delivery complex or as an additional genetic expression construct.

TABLE 1

Promoter and/or Enhancer

| Promoter/Enhancer | References |
| --- | --- |
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al; 1990 |
| Immunoglobulin Light Chain | Queen et al., 1983; Picard et al., 1984 |
| T-Cell Receptor | Luria et al., 1987; Winoto et al., 1989; Redondo et al; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Ornitz et al., 1987 |
| Metallothionein (MTII) | Karin et al., 1987; Culotta et al., 1989 |
| Collagenase | Pinkert et al., 1987; Angel et al., 1987 |
| Albumin | Pinkert et al., 1987; Tronche et al., 1989, 1990 |
| α-Fetoprotein | Godbout et al., 1988; Campere et al., 1989 |
| t-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsh et al., 1990 |
| α$_1$-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrook et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villareal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Choi et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987. |
| Hepatitis B Virus | Bulla et al., 1986; Jameel et al., 1986; Shaul et al., 1987; Spandau et al., 1988; Vannice et al., 1988 |

TABLE 1-continued

Promoter and/or Enhancer

| Promoter/Enhancer | References |
|---|---|
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 2

Inducible Elements

| Element | Inducer | References |
|---|---|---|
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Ponta et al., 1985; Sakai et al.,1988 |
| β-Interferon | poly(rI)x poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor | PMA | Hensel et al., 1989 |
| Thyroid Stimulating Hormone α Gene | Thyroid Hormone | Chatterjee et al., 1989 |

Of particular interest are muscle specific promoters (e.g. muscle creatine kinase), and more particularly, cardiac specific promoters. These include the myosin light chain-2 promoter (Franz et al., 1994; Kelly et al., 1995), the alpha actin promoter (Moss et al., 1996), the troponin 1 promoter (Bhavsar et al., 1996); the $Na^+/Ca^{2+}$ exchanger promoter (Barnes et al., 1997), the dystrophin promoter (Kimura et al., 1997), the alpha7 integrin promoter (Ziober and Kramer, 1996), the brain natriuretic peptide promoter (LaPointe et al., 1996) and the alpha B-crystallin/small heat shock protein promoter (Gopal-Srivastava, 1995), alpha myosin heavy chain promoter (Yamauchi-Takihara et al., 1989) and the ANF promoter (LaPointe et al., 1988).

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human growth hormone and SV40 polyadenylation signals. Also contemplated as an element of the expression cassette is a terminator. These elements can serve to enhance message levels and to minimize read through from the cassette into other sequences.

In certain embodiments of the invention, the cells containing nucleic acid constructs of the present invention may be identified in vitro or in vivo by including a marker in the expression construct. Such markers would confer an identifiable change to the cell permitting easy identification of cells containing the expression construct. Usually the inclusion of a drug selection marker aids in cloning and in the selection of transformants, for example, genes that confer resistance to neomycin, puromycin, hygromycin, DHFR, GPT, zeocin and histidinol are useful selectable markers. Alternatively, enzymes such as herpes simplex virus thymidine kinase (tk) or chloramphenicol acetyltransferase (CAT) may be employed. Immunologic markers also can be employed. The selectable marker employed is not believed to be important, so long as it is capable of being expressed simultaneously with the nucleic acid encoding a gene product. Further examples of selectable markers are well known to one of skill in the art.

There are a number of ways in which expression vectors may introduced into cells. In certain embodiments of the invention, the expression construct comprises a virus or engineered construct derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986).

One of the preferred methods for in vivo delivery involves the use of an adenovirus expression vector. "Adenovirus expression vector" is meant to include those constructs containing adenovirus sequences sufficient to (a) support packaging of the construct and (b) to express a polynucleotide that has been cloned therein. The expression vector comprises a genetically engineered form of adenovirus. Knowledge of the genetic organization of adenovirus, a 36 kB, linear, double-stranded DNA virus, allows substitution of large pieces of adenoviral DNA with foreign sequences up to 7 kB (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage.

Adenovirus is particularly suitable for use as a gene transfer vector because of its mid-sized genome, ease of manipulation, high titer, wide target cell range and high infectivity. Both ends of the viral genome contain 100-200 base pair inverted repeats (ITRs), which are cis elements necessary for viral DNA replication and packaging.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A-F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors, as described by Karlsson et al. (1986), or in the E4 region where a helper cell line or helper virus complements the E4 defect.

Adenovirus vectors have been used in eukaryotic gene expression (Levrero et al., 1991; Gomez-Foix et al., 1992) and vaccine development (Grunhaus and Horwitz, 1992; Graham and Prevec, 1991). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

Retroviral vectors are also suitable for expressing the polynucleotides of the invention in cells. The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al., 1988; Horwich et al., 1990).

In order to effect expression of sense or antisense gene constructs, the expression construct must be delivered into a cell. This delivery may be accomplished in vitro, as in laboratory procedures for transforming cells lines, or in vivo or ex vivo, as in the treatment of certain disease states. One mechanism for delivery is via viral infection where the expression construct is encapsidated in an infectious viral particle.

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

Once the expression construct has been delivered into the cell the nucleic acid encoding the gene of interest may be positioned and expressed at different sites. In certain embodiments, the nucleic acid encoding the gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In yet another embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Neshif (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

In still another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e., ex vivo treatment. Again, DNA encoding a particular gene may be delivered via this method and still be incorporated by the present invention.

In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Liposome-mediated nucleic acid delivery and expression of foreign DNA in vitro has been very successful. Wong et al., (1980) demonstrated the feasibility of liposome-mediated delivery and expression of foreign DNA in cultured chick embryo, HeLa and hepatoma cells. Nicolau et al., (1987) accomplished successful liposome-mediated gene transfer in rats after intravenous injection.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Other expression constructs which can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al. (1987) employed lactosyl-ceramide, a galactose-terminal asialganglioside, incorporated into liposomes and observed an increase in the uptake of the insulin gene by hepatocytes. Thus, it is feasible that a nucleic acid encoding a particular gene also may be specifically delivered into a cell type by any number of receptor-ligand systems with or without liposomes. For example, epidermal growth factor (EGF) may be used as the receptor for mediated delivery of a nucleic acid into cells that exhibit upregulation of EGF receptor. Mannose can be used to target the mannose receptor on liver cells. Also, antibodies to CD5 (CLL), CD22 (lymphoma), CD25 (T-cell leukemia) and MAA (melanoma) can similarly be used as targeting moieties.

In a particular example, the polynucleotide may be administered in combination with a cationic lipid. Examples of cationic lipids include, but are not limited to, lipofectin, DOTMA, DOPE, and DOTAP. The publication of WO/0071096, which is specifically incorporated by reference, describes different formulations, such as a DOTAP: cholesterol or cholesterol derivative formulation that can effectively be used for gene therapy. Other disclosures also discuss different lipid or liposomal formulations including nanoparticles and methods of administration; these include, but are not limited to, U.S. Patent Publication 20030203865, 20020150626, 20030032615, and 20040048787, which are specifically incorporated by reference to the extent they disclose formulations and other related aspects of administration and delivery of nucleic acids. Methods used for forming particles are also disclosed in U.S. Pat. Nos. 5,844,107, 5,877, 302, 6,008,336, 6,077,835, 5,972,901, 6,200,801, and 5,972, 900, which are incorporated by reference for those aspects.

In certain embodiments, gene transfer may more easily be performed under ex vivo conditions. Ex vivo gene therapy refers to the isolation of cells from an animal, the delivery of a nucleic acid into the cells in vitro, and then the return of the modified cells back into an animal. This may involve the surgical removal of tissue/organs from an animal or the primary culture of cells and tissues.

Drug Formulations and Routes for Administration to Subjects

The present invention also encompasses a pharmaceutical composition comprising an inhibitor or agonist of miR-499 and/or miR-208b. Where clinical applications are contemplated, pharmaceutical compositions will be prepared in a form appropriate for the intended application. Generally, this will entail preparing compositions that are essentially free of pyrogens, as well as other impurities that could be harmful to humans or animals.

Colloidal dispersion systems, such as macromolecule complexes, nanocapsules, microspheres, beads, and lipid-based systems including oil-in-water emulsions, micelles, mixed micelles, and liposomes, may be used as delivery vehicles for the oligonucleotide inhibitors of microRNA function or constructs expressing particular microRNAs. Commercially available fat emulsions that are suitable for delivering the nucleic acids of the invention to cardiac and skeletal muscle tissues include Intralipid®, Liposyn®, Liposyn® II, Liposyn® III, Nutrilipid, and other similar lipid emulsions. A preferred colloidal system for use as a delivery vehicle in vivo is a liposome (i.e., an artificial membrane vesicle). The preparation and use of such systems is well known in the art. Exemplary formulations are also disclosed in U.S. Pat. Nos. 5,981,505; 6,217,900; 6,383,512; 5,783, 565; 7,202,227; 6,379,965; 6,127,170; 5,837,533; 6,747,014; and WO03/093449, which are herein incorporated by reference in their entireties.

One will generally desire to employ appropriate salts and buffers to render delivery vehicles stable and allow for uptake by target cells. Buffers also will be employed when recombinant cells are introduced into a subject. Aqueous compositions of the present invention comprise an effective amount of the delivery vehicle comprising the inhibitor polynucleotides or miRNA polynucleotide sequences (e.g. liposomes or other complexes or expression vectors) or cells, dissolved or dispersed in a pharmaceutically acceptable carrier or aqueous medium. The phrases "pharmaceutically acceptable" or "pharmacologically acceptable" refers to molecular entities and compositions that do not produce adverse, allergic, or other untoward reactions when administered to an animal or a human. As used herein, "pharmaceutically acceptable carrier" includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the active ingredients of the present invention, its use in therapeutic compositions is contemplated. Supplementary active ingredients also can be incorporated into the compositions, provided they do not inactivate the vectors or cells of the compositions.

The active compositions of the present invention may include classic pharmaceutical preparations. Administration of these compositions according to the present invention may be via any common route so long as the target tissue is available via that route. This includes oral, nasal, or buccal. Alternatively, administration may be by intradermal, subcutaneous, intramuscular, intraperitoneal or intravenous injection, or by direct injection into cardiac tissue. Pharmaceutical compositions comprising miRNA inhibitors or expression constructs comprising miRNA sequences may also be administered by catheter systems or systems that isolate coronary circulation for delivering therapeutic agents to the heart. Various catheter systems for delivering therapeutic agents to the heart and coronary vasculature are known in the art. Some non-limiting examples of catheter-based delivery methods or coronary isolation methods suitable for use in the present invention are disclosed in U.S. Pat. Nos. 6,416,510; 6,716,196; 6,953,466, WO 2005/082440, WO 2006/089340, U.S. Patent Publication No. 2007/0203445, U.S. Patent Publication No. 2006/0148742, and U.S. Patent Publication No. 2007/0060907, which are all herein incorporated by reference in their entireties. Such compositions would normally be administered as pharmaceutically acceptable compositions, as described supra.

The active compounds may also be administered parenterally or intraperitoneally. By way of illustration, solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations generally contain a preservative to prevent the growth of microorganisms.

The pharmaceutical forms suitable for injectable use or catheter delivery include, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions may be prepared by incorporating the active compounds in an appropriate amount into a solvent along with any other ingredients (for example as enumerated above) as desired, followed by filtered sterilization. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredient(s) plus any additional desired ingredient from a previously sterile-filtered solution thereof.

The compositions of the present invention generally may be formulated in a neutral or salt form. Pharmaceutically-acceptable salts include, for example, acid addition salts (formed with the free amino groups of the protein) derived from inorganic acids (e.g., hydrochloric or phosphoric acids, or from organic acids (e.g., acetic, oxalic, tartaric, mandelic, and the like. Salts formed with the free carboxyl groups of the protein can also be derived from inorganic bases (e.g., sodium, potassium, ammonium, calcium, or ferric hydroxides) or from organic bases (e.g., isopropylamine, trimethylamine, histidine, procaine and the like.

Upon formulation, solutions are preferably administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic for example with sufficient saline or glucose. Such aqueous solutions may be used, for example, for intravenous, intramuscular, subcutaneous and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Any of the compositions described herein may be comprised in a kit. In a non-limiting example, an individual miRNA is included in a kit. The kit may further include water and hybridization buffer to facilitate hybridization of the two strands of the miRNAs. In some embodiments, the kit may include one or more oligonucleotides for inhibiting the function of a target miRNA. The kit may also include one or more transfection reagent(s) to facilitate delivery of the miRNA or miRNA inhibitors to cells.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit (labeling reagent and label may be packaged together), the kit also will generally contain a second, third or other additional container into which the additional components may be separately placed. However, various combinations of components may be comprised in a vial. The kits of the present invention also will typically include a means for containing the nucleic acids, and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred.

However, the components of the kit may be provided as dried powder(s). When reagents and/or components are provided as a dry powder, the powder can be reconstituted by the addition of a suitable solvent. It is envisioned that the solvent may also be provided in another container means.

The container means will generally include at least one vial, test tube, flask, bottle, syringe and/or other container means, into which the nucleic acid formulations are placed, preferably, suitably allocated. The kits may also comprise a second container means for containing a sterile, pharmaceutically acceptable buffer and/or other diluent.

The kits of the present invention will also typically include a means for containing the vials in close confinement for commercial sale, such as, e.g., injection and/or blow-molded plastic containers into which the desired vials are retained.

Such kits may also include components that preserve or maintain the miRNA or miRNA inhibitory oligonucleotides or that protect against their degradation. Such components may be RNAse-free or protect against RNAses. Such kits generally will comprise, in suitable means, distinct containers for each individual reagent or solution.

A kit will also include instructions for employing the kit components as well the use of any other reagent not included in the kit. Instructions may include variations that can be implemented. A kit may also include utensils or devices for administering the miRNA agonist or antagonist by various administration routes, such as parenteral or catheter administration.

It is contemplated that such reagents are embodiments of kits of the invention. Such kits, however, are not limited to the particular items identified above and may include any reagent used for the manipulation or characterization of miRNA.

Methods for Identifying Modulators

The present invention further comprises methods for identifying a modulator of miR-499 and/or miR-208b. Identified inhibitors of miR-499 and/or miR-208b are useful in the prevention or treatment or reversal of cardiac hypertrophy, heart failure, or myocardial infarction. Identified agonists of miR-499 and/or miR-208b are useful in the treatment or prevention of musculoskeletal disorders. Modulators of miR-499 and/or miR-208b may be included in pharmaceutical compositions for the treatment of cardiac disorders and/or musculoskeletal disorders according to the methods of the present invention.

These assays may comprise random screening of large libraries of candidate substances; alternatively, the assays may be used to focus on particular classes of compounds selected with an eye towards structural attributes that are believed to make them more likely to inhibit or enhance the expression and/or function of miR-499 and/or miR-208b. To identify a modulator of miR-499 or miR-208b, one generally will determine the function of a miR-499 and/or miR-208b in the presence and absence of the candidate substance. For example, a method generally comprises:

(a) providing a candidate substance;
(b) admixing the candidate substance with a miR-499 and/or miR-208b;
(c) measuring miR-499 and/or miR-208b activity; and
(d) comparing the activity in step (c) with the activity in the absence of the candidate substance,
wherein a difference between the measured activities indicates that the candidate substance is, indeed, a modulator of miR-499 and/or miR-208b.

Assays also may be conducted in isolated cells, organs, or in living organisms.

Assessing the miR-499 or miR-208b activity or expression may comprise assessing the expression level of miR-499 or miR-208b. Those in the art will be familiar with a variety of methods for assessing RNA expression levels including, for example, northern blotting or RT-PCR. Assessing the miR-499 or miR-208b activity or expression may comprise assessing the activity of miR-499 or miR-208b. In some embodiments, assessing the activity of miR-499 or miR-208b comprises assessing expression or activity of a gene regulated by miR-499 or miR-208b. Genes regulated by miR-499 include, for example, β-myosin heavy chain and fast skeletal muscle protein genes, such as troponin 12, troponin T3, myosin light chain, and α skeletal actin. Genes regulated by miR-208b include, for example, Sp3, Myostatin, PURbeta, THRAP1, and fast skeletal muscle protein genes. In certain embodiments of the invention, assessing the activity of miR-499 or miR-208b comprises assessing the ratio of α-myosin heavy chain expression level to β-myosin heavy chain expression level in the heart. In other embodiments, assessing the activity of miR-499 or miR-208b comprises assessing the expression level of the different β-myosin heavy chain isoforms in skeletal muscles. Those in the art will be familiar with a variety of methods for assessing the activity or expression of genes regulated by miR-499 or miR-208b. Such methods include, for example, northern blotting, RT-PCR, ELISA, or western blotting.

It will, of course, be understood that all the screening methods of the present invention are useful in themselves notwithstanding the fact that effective candidates may not be found. The invention provides methods for screening for such candidates, not solely methods of finding them.

As used herein the term "candidate substance" refers to any molecule that may potentially modulate the β-MHC-regulating aspects of miR-499 and/or miR-208b. One will typically acquire, from various commercial sources, molecular libraries that are believed to meet the basic criteria for useful drugs in an effort to "brute force" the identification of useful compounds. Screening of such libraries, including combinatorially-generated libraries (e.g., antagomir libraries), is a rapid and efficient way to screen a large number of related (and unrelated) compounds for activity. Combinatorial approaches also lend themselves to rapid evolution of potential drugs by the creation of second, third, and fourth generation compounds modeled on active, but otherwise undesirable compounds. Non-limiting examples of candidate substances that may be screened according to the methods of the present invention are proteins, peptides, polypeptides, polynucleotides, oligonucleotides or small molecules. Modulators of miR-499 and/or miR-208b may also be agonists or antagonists of an upstream regulators of miR-499 and/or miR-208b, such as miR-208.

A quick, inexpensive and easy assay to run is an in vitro assay. Such assays generally use isolated molecules, can be run quickly and in large numbers, thereby increasing the amount of information obtainable in a short period of time. A variety of vessels may be used to run the assays, including test tubes, plates, dishes and other surfaces such as dipsticks or beads.

A technique for high throughput screening of compounds is described in WO 84/03564, which is herein incorporated by reference in its entirety. Large numbers of small antogomir compounds may be synthesized on a solid substrate, such as plastic pins or some other surface. Such molecules can be rapidly screening for their ability to hybridize to miR-499 or miR-208b.

The present invention also contemplates the screening of compounds for their ability to modulate miR-499 or miR-208b activity and expression in cells. Various cell lines, including those derived from skeletal muscle cells, can be utilized for such screening assays, including cells specifically engineered for this purpose. Primary cardiac cells also may be used, as can the H9C2 cell line.

In vivo assays involve the use of various animal models of heart disease or musculoskeletal disease, including transgenic animals, that have been engineered to have specific defects, or carry markers that can be used to measure the ability of a candidate substance to reach and effect different cells within the organism. Due to their size, ease of handling, and information on their physiology and genetic make-up, mice are a preferred embodiment, especially for transgenics. However, other animals are suitable as well, including rats, rabbits, hamsters, guinea pigs, gerbils, woodchucks, cats, dogs, sheep, goats, pigs, cows, horses and monkeys (including chimps, gibbons and baboons). Assays for inhibitors may be conducted using an animal model derived from any of these species.

Treatment of animals with test compounds will involve the administration of the compound, in an appropriate form, to the animal. Administration will be by any route that could be utilized for clinical purposes. Determining the effectiveness of a compound in vivo may involve a variety of different criteria, including but not limited to alteration of hypertrophic signaling pathways and physical symptoms of hypertrophy. Also, measuring toxicity and dose responses can be performed in animals in a more meaningful fashion than in in vitro or in cyto assays.

In one embodiment, the present invention provides a method of regulating cardiac and/or skeletal muscle contractility comprising administering a modulator of miR 499 and/or miR-208b expression or activity to heart and/or skeletal muscle cells. In another embodiment, there is provided a method of regulating cardiac contractile protein gene expression comprising administering a modulator of miR 499 and/or miR-208b expression or activity to heart cells. In another embodiment, there is provided a method of regulating skeletal muscle contractile protein gene expression comprising administering a modulator of miR 499 and/or miR-208b expression or activity to skeletal muscle cells. In still another embodiment, the present invention provides a method of inducing a fiber type switch of a skeletal muscle cell comprising administering a modulator of miR 499 and/or miR-208b expression or activity to the skeletal muscle cell. The modulator may be an agonist or an antagonist of miR 499 and/or miR-208b expression or activity. In some embodiments, the expression of THRAP1, PURbeta, myostatin, and Sox 6 are increased in a cell by contacting the cell with a miR-499 inhibitor. In other embodiments, expression of THRAP1, PURbeta, myostatin, and Sox 6 are decreased in a cell by contacting the cell with a miR-499 agonist. In another embodiment, the expression of Sp3, Myostatin, PURbeta, and THRAP1 are increased in a cell by contacting the cell with a miR-208b inhibitor. In still another embodiment, the expression of Sp3, Myostatin, PURbeta, and THRAP1 are decreased in a cell by contacting the cell with a miR-208b agonist.

In certain embodiments of the invention, there is provided a method of reducing β-MHC expression in heart cells comprising administering an inhibitor of miR 499 and/or miR-208b expression or activity to the heart cells. In other embodiments of the invention, there is provided a method of elevating β-MHC expression in heart cells comprising increasing endogenous miR 499 and/or miR-208b expression or activity or administering exogenous miR-499 and/or miR-208b to heart cells. In one embodiment of the invention, there is provided a method of increasing the expression of a fast skeletal muscle contractile protein gene in heart cells comprising administering to the heart cells an inhibitor of miR-499 and/or miR-208b expression or activity. In another embodiment of the invention, there is provided a method of decreasing the expression of a fast skeletal muscle contractile protein gene in heart cells comprising increasing endogenous miR 499 and/or miR-208b expression or activity or administering exogenous miR-499 and/or miR-208b to the heart cells. Examples of fast skeletal muscle contractile protein genes that may be increased or decreased according to the methods of the present invention include, but are not limited to, troponin I2; troponin T3, myosin light chain, or alpha skeletal actin.

In one embodiment, the present invention provides a method for treating pathologic cardiac hypertrophy, heart failure, or myocardial infarction in a subject in need thereof comprising: identifying a subject having cardiac hypertrophy, heart failure, or myocardial infarction; and administering an miR-499 and/or miR-208b inhibitor to the subject. In certain embodiments of the invention the miR-499 and/or miR-208b inhibitor may be identified by a method comprising: (a) contacting a cell with a candidate substance; (b) assessing miR-499 and/or miR-208b activity or expression; and (c) comparing the activity or expression in step (b) with the activity or expression in the absence of the candidate substance, wherein a reduction in the activity or expression of miR-499 and/or miR-208b in the cell contacted with the candidate substance compared to the activity or expression in the cell in the absence of the candidate substance indicates that the candidate substance is an inhibitor of miR-499 and/or miR-208b.

In another embodiment, the present invention provides a method for treating a musculoskeletal disorder in a subject in need thereof comprising: identifying a subject having a musculoskeletal disorder or at risk for developing a musculoskeletal disorder; and administering an miR 499 and/or miR-208b agonist to the subject. In certain embodiments of the invention, the miR 499 and/or miR-208b agonist may be identified by a method comprising: (a) contacting a cell with a candidate substance; (b) assessing miR 499 and/or miR-208b activity or expression; and (c) comparing the activity or expression in step (b) with the activity or expression in the absence of the candidate substance, wherein an increase in the activity or expression of miR 499 and/or miR-208b in the cell contacted with the candidate substance compared to the activity or expression in the cell in the absence of the candidate substance indicates that the candidate substance is an agonist of miR-499 and/or miR-208b.

Transgenic Animals

A particular embodiment of the present invention provides transgenic animals that lack one or both functional miR-499 and/or miR-208b alleles. Also, transgenic animals that express miR-499 and/or miR-208b under the control of an inducible, tissue selective or a constitutive promoter, recombinant cell lines derived from such animals, and transgenic embryos may be useful in determining the exact role that miR-499 or miR-208b plays in the development and differentiation of cardiomyocytes and in the development of pathologic cardiac hypertrophy and heart failure. Furthermore, these transgenic animals may provide an insight into heart development. The use of an inducible or repressable miR-499 and/or miR-208b encoding nucleic acid provides a model for over- or unregulated expression. Also, transgenic animals that are "knocked out" for miR-499 and/or miR-208b, in one or both alleles, are contemplated.

In a general embodiment, a transgenic animal is produced by the integration of a given transgene into the genome in a manner that permits the expression of the transgene. Methods for producing transgenic animals are generally described by Wagner and Hoppe (U.S. Pat. No. 4,873,191; incorporated herein by reference), and Brinster et al. (1985; incorporated herein by reference).

Typically, a gene flanked by genomic sequences is transferred by microinjection into a fertilized egg. The microinjected eggs are implanted into a host female, and the progeny are screened for the expression of the transgene. Transgenic animals may be produced from the fertilized eggs from a number of animals including, but not limited to reptiles, amphibians, birds, mammals, and fish.

DNA clones for microinjection can be prepared by any means known in the art. For example, DNA clones for microinjection can be cleaved with enzymes appropriate for removing the bacterial plasmid sequences, and the DNA fragments electrophoresed on 1% agarose gels in TBE buffer, using standard techniques. The DNA bands are visualized by staining with ethidium bromide, and the band containing the expression sequences is excised. The excised band is then placed in dialysis bags containing 0.3 M sodium acetate, pH 7.0. DNA is electroeluted into the dialysis bags, extracted with a 1:1 phenol:chloroform solution and precipitated by two volumes of ethanol. The DNA is redissolved in 1 ml of low salt buffer (0.2 M NaCl, 20 mM Tris, pH 7.4, and 1 mM EDTA) and purified on an Elutip-D™ column. The column is first primed with 3 ml of high salt buffer (1 M NaCl, 20 mM Tris, pH 7.4, and 1 mM EDTA) followed by washing with 5 ml of low salt buffer. The DNA solutions are passed through the column three times to bind DNA to the column matrix. After one wash with 3 ml of low salt buffer, the DNA is eluted with 0.4 ml high salt buffer and precipitated by two volumes of ethanol. DNA concentrations are measured by absorption at 260 nm in a UV spectrophotometer. For microinjection, DNA concentrations are adjusted to 3 µg/ml in 5 mM Tris, pH 7.4 and 0.1 mM EDTA. Other methods for purification of DNA for microinjection are described in Palmiter et al. (1982); and in Sambrook et al. (2001).

In an exemplary microinjection procedure, female mice six weeks of age are induced to superovulate with a 5 IU injection (0.1 cc, ip) of pregnant mare serum gonadotropin (PMSG; Sigma) followed 48 hours later by a 5 IU injection (0.1 cc, ip) of human chorionic gonadotropin (hCG; Sigma). Females are placed with males immediately after hCG injection. Twenty-one hours after hCG injection, the mated females are sacrificed by C02 asphyxiation or cervical dislocation and embryos are recovered from excised oviducts and placed in Dulbecco's phosphate buffered saline with 0.5% bovine serum albumin (BSA; Sigma). Surrounding cumulus cells are removed with hyaluronidase (1 mg/ml). Pronuclear embryos are then washed and placed in Earle's balanced salt solution containing 0.5% BSA (EBSS) in a 37.5° C. incubator with a humidified atmosphere at 5% $CO_2$, 95% air until the time of injection. Embryos can be implanted at the two-cell stage.

Randomly cycling adult female mice are paired with vasectomized males. C57BL/6 or Swiss mice or other comparable strains can be used for this purpose. Recipient females are mated at the same time as donor females. At the time of embryo transfer, the recipient females are anesthetized with an intraperitoneal injection of 0.015 ml of 2.5% avertin per gram of body weight. The oviducts are exposed by a single midline dorsal incision. An incision is then made through the body wall directly over the oviduct. The ovarian bursa is then torn with watchmakers forceps. Embryos to be transferred are placed in DPBS (Dulbecco's phosphate buffered saline) and in the tip of a transfer pipet (about 10 to 12 embryos). The pipet tip is inserted into the infundibulum and the embryos transferred. After the transfer, the incision is closed by two sutures.

Definitions

As used herein, the term "heart failure" is broadly used to mean any condition that reduces the ability of the heart to pump blood. As a result, congestion and edema develop in the tissues. Most frequently, heart failure is caused by decreased contractility of the myocardium, resulting from reduced coronary blood flow; however, many other factors may result in heart failure, including damage to the heart valves, vitamin deficiency, and primary cardiac muscle disease. Though the precise physiological mechanisms of heart failure are not entirely understood, heart failure is generally believed to involve disorders in several cardiac autonomic properties, including sympathetic, parasympathetic, and baroreceptor responses. The phrase "manifestations of heart failure" is used broadly to encompass all of the sequelae associated with heart failure, such as shortness of breath, pitting edema, an enlarged tender liver, engorged neck veins, pulmonary rales and the like including laboratory findings associated with heart failure.

The term "treatment" or grammatical equivalents encompasses the improvement and/or reversal of the symptoms of heart failure (i.e., the ability of the heart to pump blood). "Improvement in the physiologic function" of the heart may be assessed using any of the measurements described herein (e.g., measurement of ejection fraction, fractional shortening, left ventricular internal dimension, heart rate, etc.), as well as any effect upon the animal's survival. In use of animal models, the response of treated transgenic animals and untreated transgenic animals is compared using any of the assays described herein (in addition, treated and untreated non-transgenic animals may be included as controls). A compound which causes an improvement in any parameter associated with heart failure used in the screening methods of the instant invention may thereby be identified as a therapeutic compound.

The term "dilated cardiomyopathy" refers to a type of heart failure characterized by the presence of a symmetrically dilated left ventricle with poor systolic contractile function and, in addition, frequently involves the right ventricle.

The term "compound" refers to any chemical entity, pharmaceutical, drug, and the like that can be used to treat or prevent a disease, illness, sickness, or disorder of bodily function. Compounds comprise both known and potential therapeutic compounds. A compound can be determined to be therapeutic by screening using the screening methods of the present invention. A "known therapeutic compound" refers to a therapeutic compound that has been shown (e.g., through animal trials or prior experience with administration to humans) to be effective in such treatment. In other words, a known therapeutic compound is not limited to a compound efficacious in the treatment of heart failure.

As used herein, the term "cardiac hypertrophy" refers to the process in which adult cardiac myocytes respond to stress through hypertrophic growth. Such growth is characterized by cell size increases without cell division, assembling of additional sarcomeres within the cell to maximize force generation, and an activation of a fetal cardiac gene program. Cardiac hypertrophy is often associated with increased risk of morbidity and mortality, and thus studies aimed at understanding the molecular mechanisms of cardiac hypertrophy could have a significant impact on human health.

As used herein, the term "modulate" refers to a change or an alteration in a biological activity. Modulation may be an increase or a decrease in protein activity, a change in kinase activity, a change in binding characteristics, or any other change in the biological, functional, or immunological properties associated with the activity of a protein or other structure of interest. The term "modulator" refers to any molecule or compound which is capable of changing or altering biological activity as described above.

The term "β-adrenergic receptor antagonist" refers to a chemical compound or entity that is capable of blocking, either partially or completely, the beta (β) type of adrenoreceptors (i.e., receptors of the adrenergic system that respond to catecholamines, especially norepinephrine). Some β-adrenergic receptor antagonists exhibit a degree of specificity for one receptor subtype (generally $\beta_1$); such antagonists are termed "$\beta_1$-specific adrenergic receptor antagonists" and "$\beta_2$-specific adrenergic receptor antagonists." The term β-adrenergic receptor antagonist" refers to chemical compounds that are selective and non-selective antagonists. Examples of β-adrenergic receptor antagonists include, but are not limited to, acebutolol, atenolol, butoxamine, carteolol, esmolol, labetolol, metoprolol, nadolol, penbutolol, propanolol, and timolol. The use of derivatives of known β-adrenergic receptor antagonists is encompassed by the methods of the present invention. Indeed any compound, which functionally behaves as a β-adrenergic receptor antagonist is encompassed by the methods of the present invention.

The terms "angiotensin-converting enzyme inhibitor" or "ACE inhibitor" refer to a chemical compound or entity that is capable of inhibiting, either partially or completely, the enzyme involved in the conversion of the relatively inactive angiotensin I to the active angiotensin II in the renin-angiotensin system. In addition, the ACE inhibitors concomitantly inhibit the degradation of bradykinin, which likely significantly enhances the antihypertensive effect of the ACE inhibitors. Examples of ACE inhibitors include, but are not limited to, benazepril, captopril, enalapril, fosinopril, lisinopril, quinapril and ramipril. The use of derivatives of known ACE inhibitors is encompassed by the methods of the present invention. Indeed any compound, which functionally behaves as an ACE inhibitor, is encompassed by the methods of the present invention.

As used herein, the term "genotypes" refers to the actual genetic make-up of an organism, while "phenotype" refers to physical traits displayed by an individual. In addition, the "phenotype" is the result of selective expression of the genome (i.e., it is an expression of the cell history and its response to the extracellular environment). Indeed, the human genome contains an estimated 30,000-35,000 genes. In each cell type, only a small (i.e., 10-15%) fraction of these genes are expressed.

The use of the word "a" or "an" when used in conjunction with the term "comprising" in the claims and/or the specification may mean "one," but it is also consistent with the meaning of "one or more," "at least one," and "one or more than one." It is contemplated that any embodiment discussed herein can be implemented with respect to any method or composition of the invention, and vice versa. Furthermore, compositions and kits of the invention can be used to achieve methods of the invention. Throughout this application, the term "about" is used to indicate that a value includes the standard deviation of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Although section headers have been inserted into this application to facilitate review, such headers should not be construed as a division of embodiments.

The following examples are included to further illustrate various aspects of the invention. It should be appreciated by those of skill in the art that the techniques disclosed in the examples which follow represent techniques and/or compositions discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Encoded within an intron of the α-MHC gene is miR-208 (FIG. 1A). Like α-MHC, miR-208 is expressed specifically in the heart with trace expression in the lung (FIG. 1B). miR-208 is processed out of the α-MHC pre-mRNA rather than being transcribed as a separate transcript. Intriguingly, however, miR-208 displays a remarkably long half-life of at least 14 days, and can thereby exert functions even when α-MHC mRNA expression has been down-regulated. Although genetic deletion of miR-208 in mice failed to induce an overt phenotype, microarray analysis on hearts from wild-type and miR-208$^{-/-}$ animals at 2 months of age revealed removal of miR-208 to result in pronounced expression of numerous fast skeletal muscle contractile protein genes, which are normally not expressed in the heart. Thus, these results suggest that under normal conditions miR-208 is co-expressed with the sole cardiac-specific MHC gene to maintain cardiomyocyte identity by repressing the expression of skeletal muscle genes in the heart.

Figure 5:
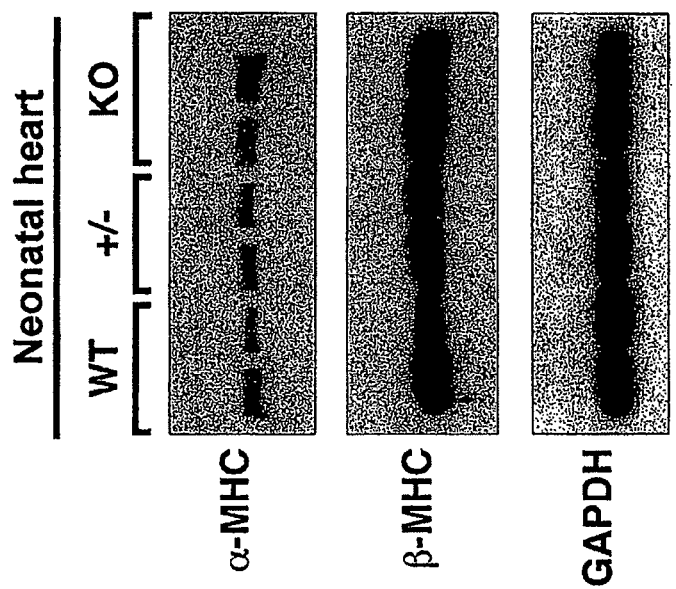
FIG. 5. Western analysis of α-MHC and β-MHC protein levels in hearts of neonatal mice of the indicated genotypes. Two mice of each genotype were analyzed. GAPDH was detected as a loading control.
Figure 6:
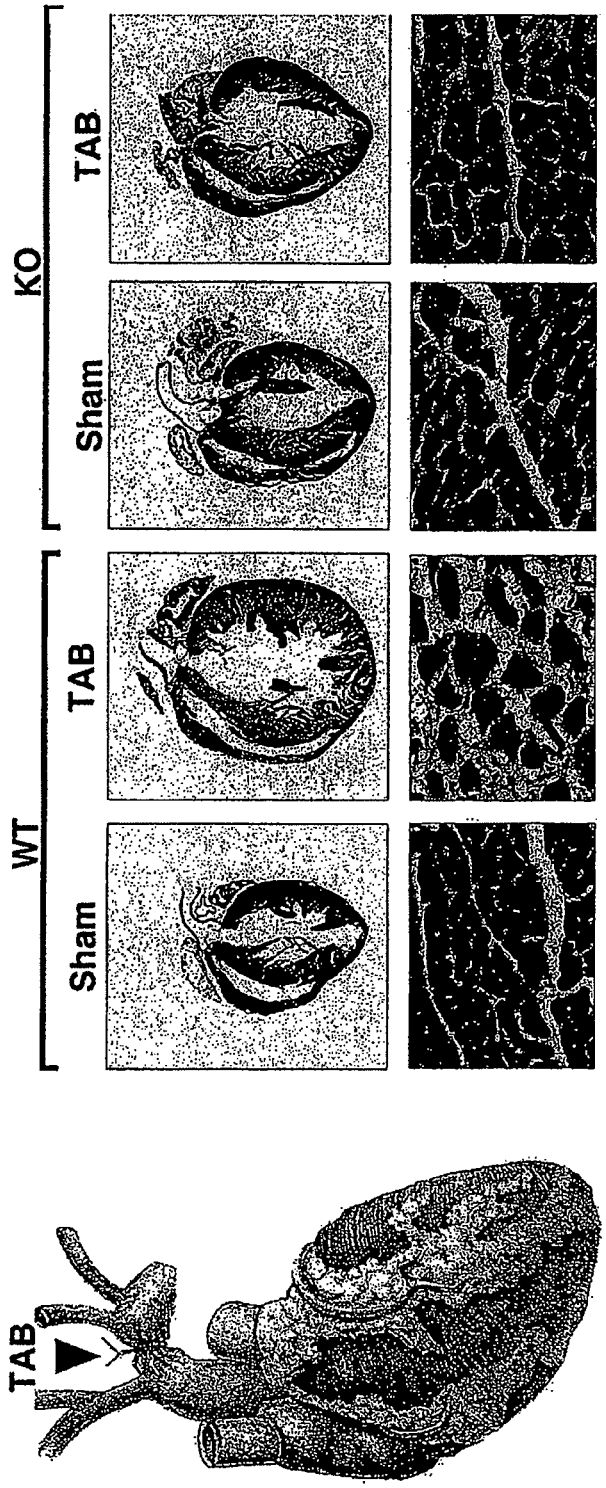
FIG. 6. MiR-208$^{-/-}$ mice show reduced cardiac hypertrophy in response to pressure overload. Histological sections of hearts of wild-type and miR-208$^{-/-}$ mice stained for Masson trichrome. The absence of miR-208 diminishes hypertrophy and fibrosis seen in wild-type mice subjected to TAB for 21 days. Scale bar equals 2 mm in top panel and 20 μm for bottom panel.
Figure 7:
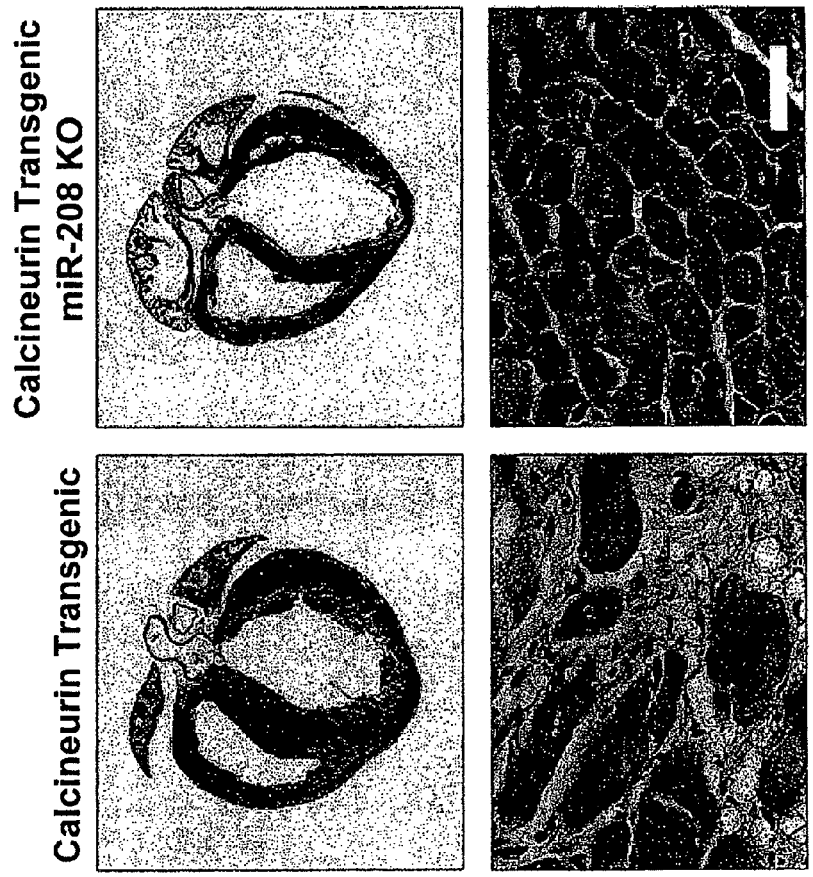
FIG. 7. MiR-208$^{-/-}$ mice show reduced cardiac hypertrophy in response to calcineurin activation. Histological sections of hearts of 6 week-old mice expressing a calcineurin transgene (CnA-Tg) and hearts of miR-208$^{-/-}$; CnA-Tg stained for Masson trichrome. Absence of miR-208 diminishes hypertrophy and fibrosis seen in CnA-Tg mice. Scale bar=2 mm for top panel, 20 μm for bottom panel.
Figure 8:
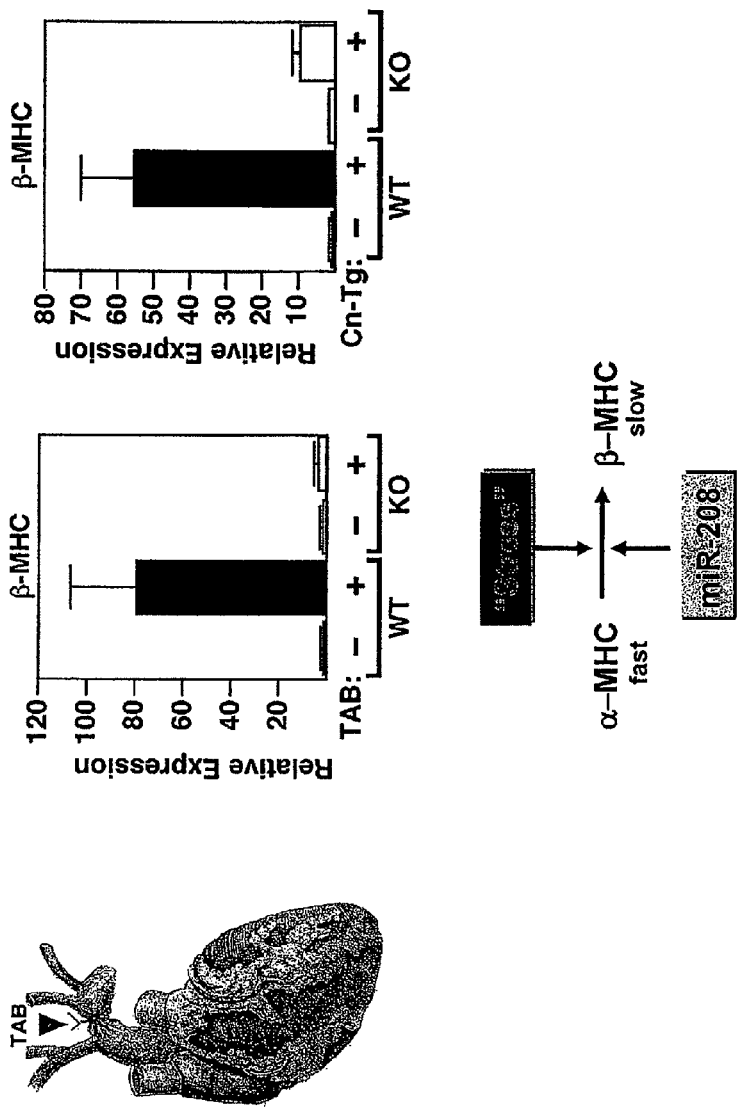
FIG. 8. Mir-208$^{-/-}$ mice fail to up-regulate β-MHC in response to Thoracic Aortic Banding (TAB) and calcineurin activation.
Figure 10:
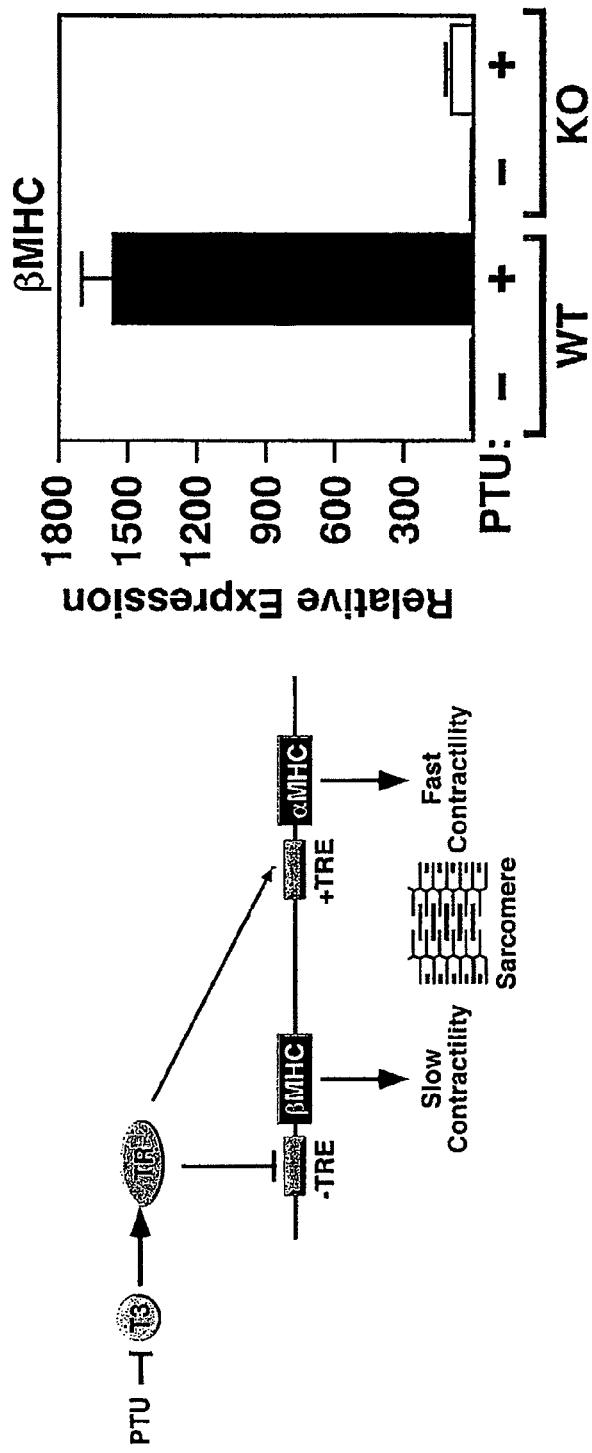
FIG. 10. MiR-208$^{-/-}$ mice fail to up-regulate β-MHC in response to hypothyroidism with propylthiouracil (PTU) treatment.
Figure 11:
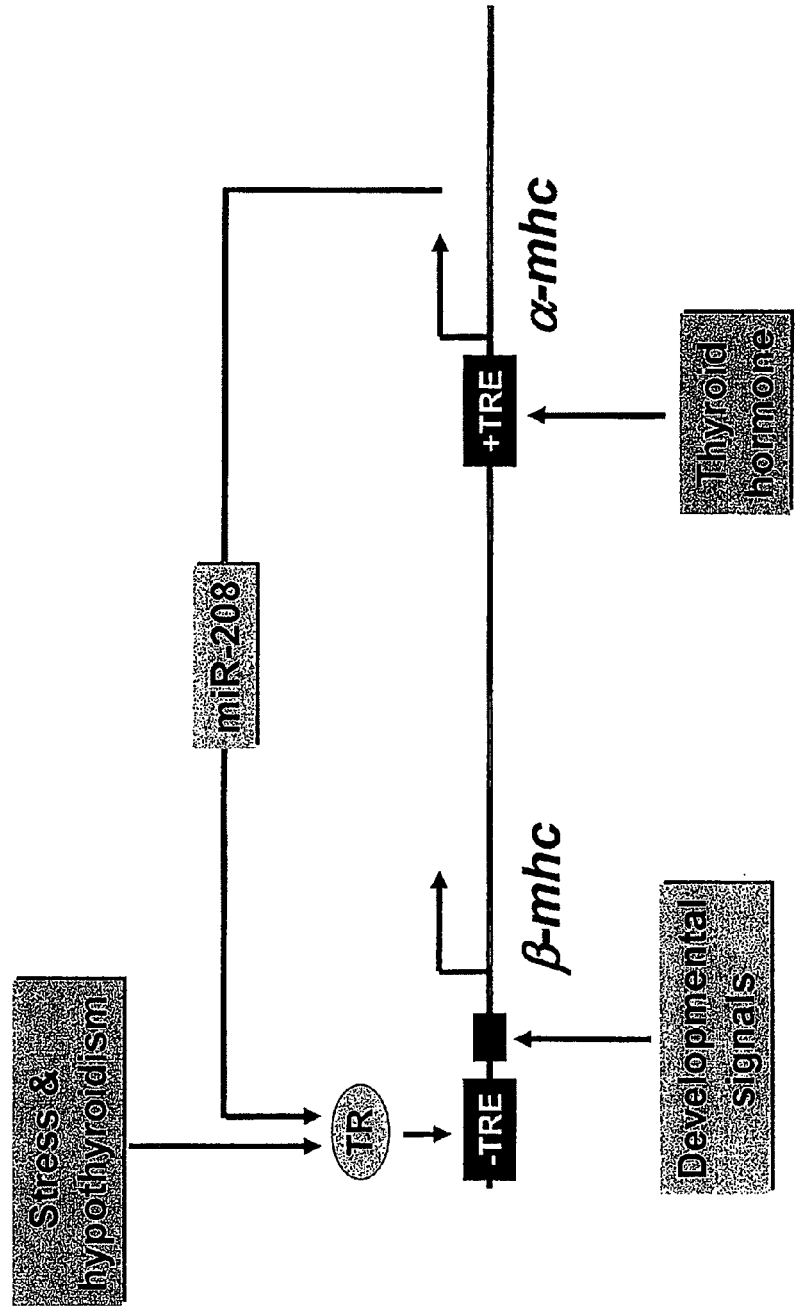
FIG. 11. Schematic diagram of the role of miR-208 in the control of β-MHC expression.

The most remarkable function of miR-208 was revealed by the aberrant response of miR-208 null mice to cardiac stress (van Rooij, Science 2007). In response to pressure overload by thoracic aortic constriction or signaling by calcineurin, a calcium/calmodulin-dependent phosphatase that drives pathological remodeling of the heart, miR-208 null mice showed virtually no hypertrophy of cardiomyocytes or fibrosis and were unable to up-regulate β-MHC expression (FIGS. 6-8). In contrast, other stress responsive genes, such as those encoding ANF and BNP, were strongly induced in miR-208 mutant animals, demonstrating that miR-208 is dedicated specifically to the control of β-MHC expression, which can be uncoupled from other facets of the cardiac stress response.

β-MHC expression is repressed by thyroid hormone signaling and is up-regulated in the hypothyroid state (Leung et al., 2006). miR-208$^{-/-}$ animals were also resistant to up-regulation of β-MHC expression following treatment with the T3 inhibitor propylthiouracil (PTU), which induces hypothyroidism. Intriguingly, however, expression of β-MHC before birth was normal in miR-208 mutant mice, indicating that miR-208 is dedicated specifically to the post-natal regulation of β-MHC expression, which coincides with the acquisition of thyroid hormone responsiveness of the β-MHC gene (FIG. 5).

A clue to the mechanism of action of miR-208 comes from the resemblance of miR-208$^{-/-}$ hearts to hyperthyroid hearts, both of which display a block to β-MHC expression, up-regulation of stress-response genes and protection against pathological hypertrophy and fibrosis (FIGS. 6-10). The up-regulation of fast skeletal muscle genes in miR-208$^{-/-}$ hearts (FIGS. 22 and 27) also mimics the induction of fast skeletal muscle fibers in the hyperthyroid state (Wei et al., 2005).

Figure 12:
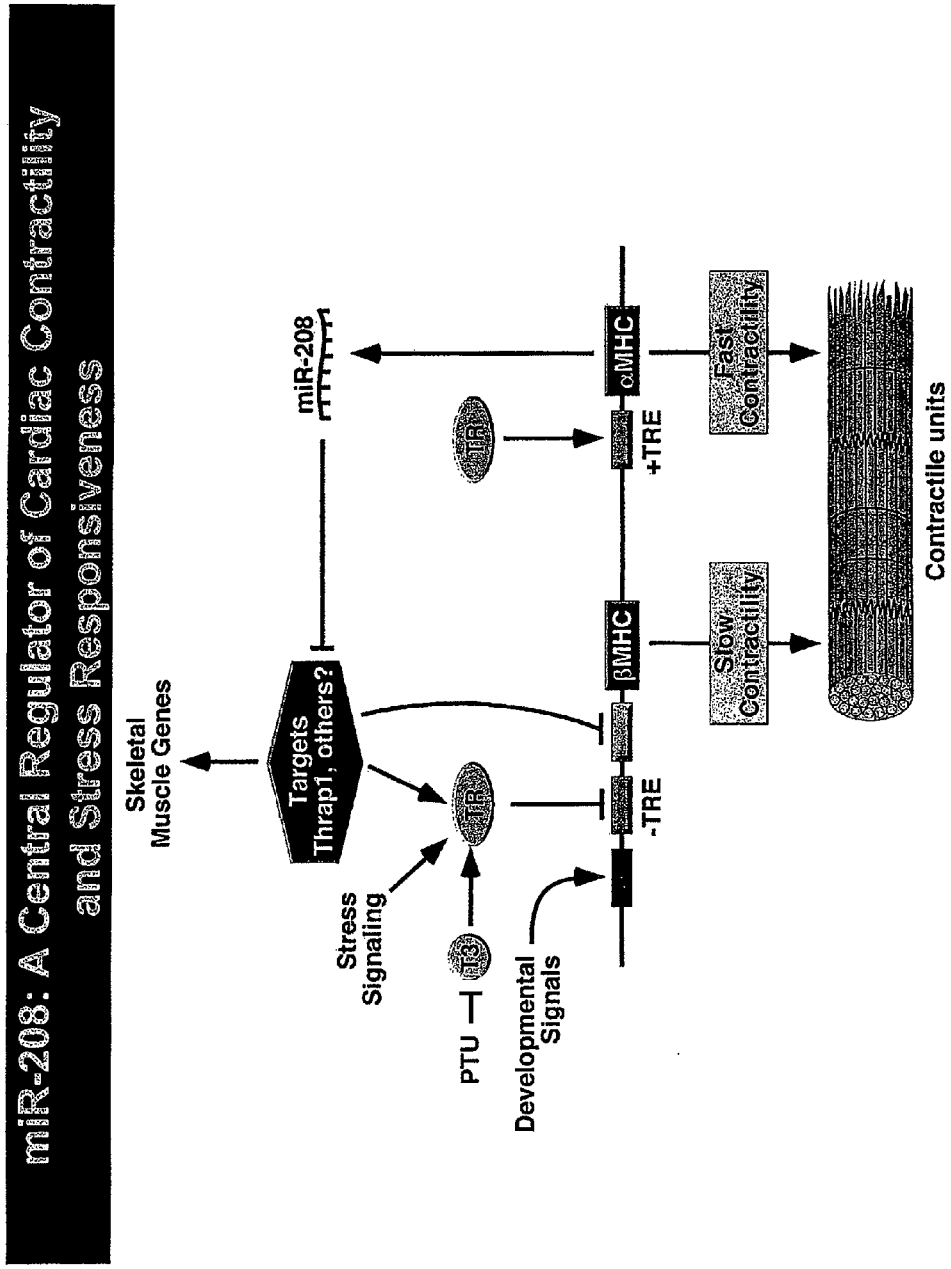
FIG. 12. Schematic diagram of the role of miR-208 in the regulation of β-MHC and fast skeletal muscle gene expression via Thrap1.
Figure 26:
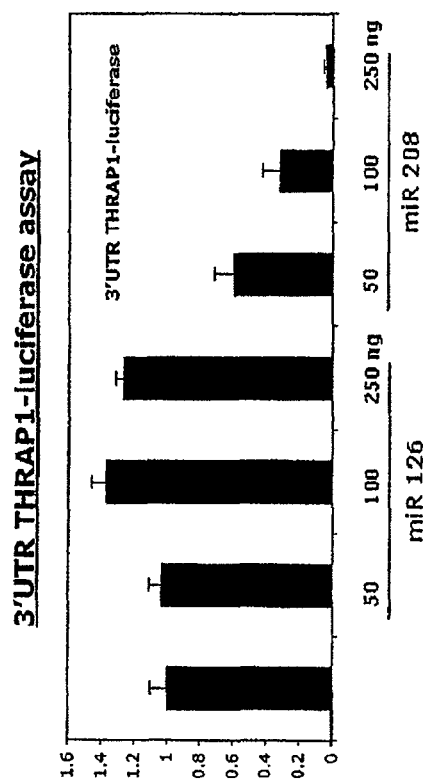
FIG. 26. 3' UTR THRAP1 luciferase assay. Expression of a luciferase gene containing the 3' UTR of THRAP1 is decreased in cells co-transfected with miR-208, but not miR-126 (control).

These findings suggest that miR-208 acts, at least in part, by repressing expression of a common component of stress-response and thyroid hormone signaling pathways in the heart. Among the strongest predicted targets of miR-208 is the thyroid hormone receptor (TR) co-regulator THRAP1, which can exert positive and negative effects on transcription (Pantos et al., 2006; Yao and Eghbali, 1992; FIG. 12). The TR acts through a negative thyroid hormone response element (TRE) to repress β-MHC expression in the adult heart (Zhao et al., 2005). Thus, the increase in THRAP1 expression in the absence of miR-208 would be predicted to enhance the repressive activity of the TR toward β-MHC expression, consistent with the blockade to β-MHC expression in miR-208$^{-/-}$ hearts. However, although THRAP1 appears to be a bone fide target for miR-208 (FIGS. 25 and 26), these data do not exclude the potential involvement of additional targets in the regulation of β-MHC expression.

Figure 13:
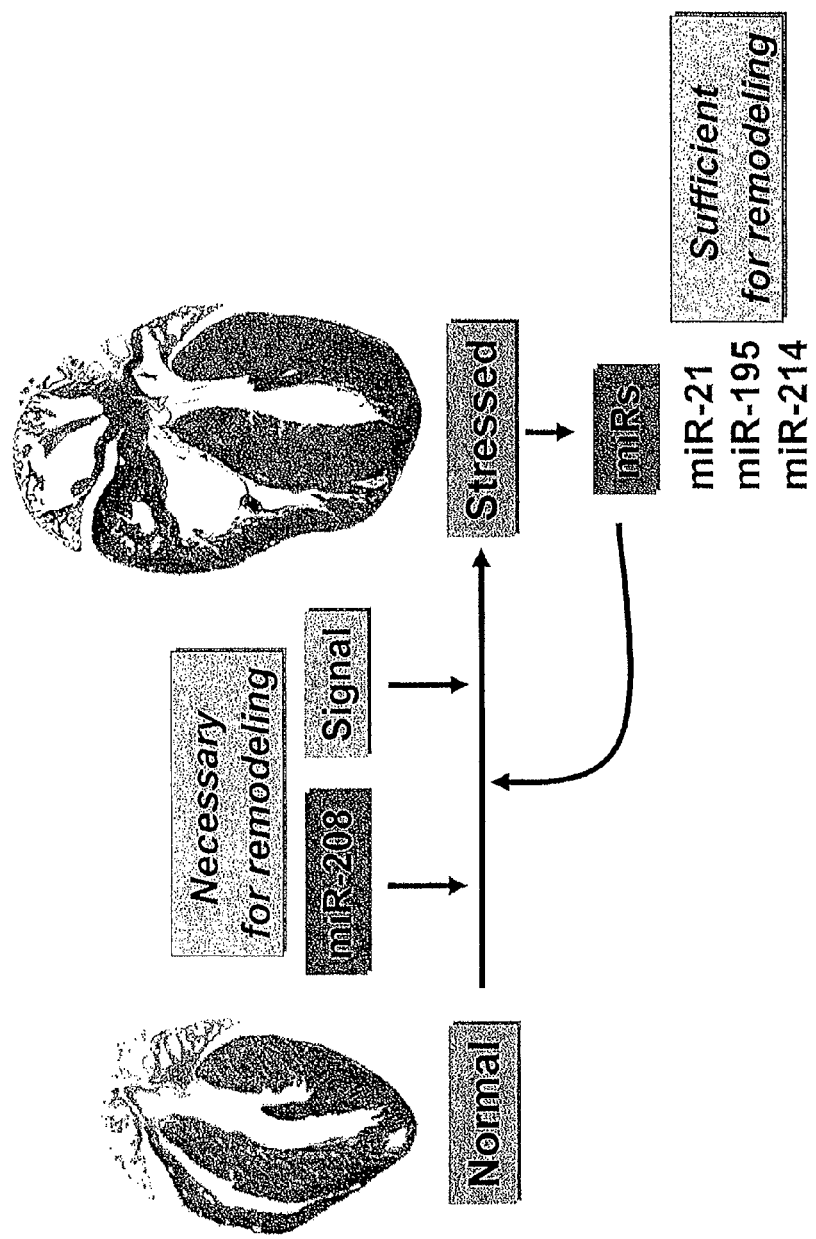
FIG. 13. Mechanisms of action of microRNAs during cardiac hypertrophy.

Since even a subtle shift towards β-MHC reduces mechanical performance and efficiency of the adult heart, it would be of therapeutic value to exploit miR-208 regulation to prevent an increase in β-MHC expression during cardiac disease. The cardiac specificity and dedication of miR-208 to the cardiac stress response, but not to normal cardiac development, make miR-208 (and its down-stream effectors) an attractive therapeutic target for manipulating β-MHC levels (FIG. 13).

Materials & Methods

Northern blot analysis. Cardiac tissue samples of left ventricles of anonymous humans diagnosed as having non-failing or failing hearts were obtained from Gilead Colorado (Westminster, Colo.). Total RNA was isolated from mouse, rat and human cardiac tissue samples using Trizol reagent (Gibco/BRL). Northern blots to detect microRNAs were performed as described previously (1). A U6 probe served as a loading control (U6 forward: 5-GTGCTCGCTTCG-GCAGC-3, (SEQ ID NO: 28); U6 reverse: 5-AAAATATG-GAACGCTTCACGAATTTGCG-3 (SEQ ID NO: 29)). To detect α-MHC expression, a Northern blot containing 10 μg of RNA from cardiac tissue of both adult wild-type and miR-208 mutant animals was probed with a cDNA fragment of α-MHC covering a part of the 5'UTR region and first exon.

PTU treatment. Thyroid hormone deficiency was induced by feeding animals for the indicated durations with iodine-free chow supplemented with 0.15% PTU purchased from Harlan Teklad Co. (TD 97061) (Madison, Wis.).

Microarray and realtime PCR analysis. Total RNA from cardiac tissue was isolated using Trizol (Invitrogen). Microarray analysis was performed using Mouse Genome 430 2.0 array (Affymetrix). RT-PCR with random hexamer primers (Invitrogen) was performed on RNA samples, after which the expression of a subset of genes was analyzed by quantitative real time PCR using Taqman probes purchased from ABI.

Generation of miR-208 mutant mice. To generate the miR-208 targeting vector, a 0.4 kb fragment (5' arm) extending upstream of the miR-208 coding region was digested with SacII and NotI and ligated into the pGKneoF2L2dta targeting plasmid upstream of the loxP sites and the Frt-flanked neomycin cassette. A 3.3 kb fragment (3' arm) was digested with SalI and HindIII and ligated into the vector between the neomycin resistance and Dta negative selection cassettes. Targeted ES-cells carrying the disrupted allele were identified by Southern blot analysis with 5' and 3' probes. Three miR-208 targeted ES clones were identified and used for blastocyst injection. The resulting chimeric mice were bred to C57BL/6 to obtain germline transmission of the mutant allele.

Western blotting. Myosin was extracted from cardiac tissue as described (Morkin, 2000). MHC isoforms were separated by SDS PAGE and Western blotting was performed with mouse monoclonal α-MHC (BA-G5) (ATCC, Rockville, Md.) and mouse monoclonal antimyosin (slow, skeletal M8421) (Sigma, Mo.), which is highly specific for β-MHC. To detect all striated myosin a pan specific antibody (mouse monoclonal 3-48; Accurate Chemical & Scientific Corporation, NY) was used. THRAP1 was detected by immunoprecipitation from 400 μg of cardiac protein lysate. After pre-clearing the samples for 1 hour at 4° C., the supernatant was incubated overnight at 4° C. with 1 μl rabbit polyclonal anti-THRAP1 (a kind gift of R. Roeder, Rockefeller University) and 15 μl of protein A beads. The beads were washed three times with lysis buffer and boiled in SDS sample buffer. Immunoprecipitated THRAP1 protein was resolved by SDS-PAGE and analyzed using rabbit polyclonal anti-THRAP1 at a dilution of 1:3000 and anti-rabbit IgG conjugated to horseradish peroxidase at a dilution of 1:5000 with detection by Luminol Reagent (Santa Cruz).

Histological analysis and RNA In situ hybridization. Tissues used for histology were incubated in Krebs-Henselheit solution, fixed in 4% paraformaldehyde, sectioned, and processed for hematoxylin and eosin (H&E) and Masson's Trichrome staining or in situ hybridization by standard techniques (Krenz and Robbins, 2004). $^{35}$S-labeled RNA probes were generated using Maxiscript kit (Amersham). Signals were pseudocolored in red using Adobe Photoshop.

Transthoracic echocardiography. Cardiac function and heart dimensions were evaluated by two-dimensional echocardiography in conscious mice using a Vingmed System (GE Vingmed Ultrasound, Horten, Norway) and a 11.5-MHz linear array transducer. M-mode tracings were used to measure anterior and posterior wall thicknesses at end diastole and end systole. Left ventricular (LV) internal diameter (LVID) was measured as the largest anteroposterior diameter in either diastole (LVIDd) or systole (LVIDs). The data were analyzed by a single observer blinded to mouse genotype. LV fractional shortening (FS) was calculated according to the following formula: FS (%)=[(LVIDd−LVIDs)/LVIDd]×100.

Generation of transgenic mice. A mouse genomic fragment flanking the miRNA of interest was subcloned into a cardiac-specific expression plasmid containing the α-MHC and human GH poly(A)+ signal (Kiriazis and Kranias, 2000). Genomic DNA was isolated from mouse tail biopsies and analyzed by PCR using primers specific for the human GH poly(A)+ signal.

Generation of LacZ and MCK transgenic mice. To search for cis-regulatory elements responsible for cardiac and skeletal muscle expression of myh7b/miR-499, 0.8 Kb genomic fragments of the mouse myh7b gene were fused to the hsp68 basal promoter upstream of a lacZ reporter gene and tested for expression in F0 transgenic mouse embryos. For the generation of transgenic mice, constructs were digested with SalI to remove vector sequences. DNA fragments were purified using a QiaQuick spin column (Qiagen, MD), injected into fertilized eggs from B6C3F1 female mice, and implanted into pseudopregnant ICR mice as previously described (Lien et al., 1999). Embryos were collected and stained for β-galactosidase activity. Transgenic mice that express constitutively active forms of miR-499 under the control of a muscle-specific enhancer from the muscle creatine kinase (MCK) gene are described elsewhere (Naga et al. (2000) J. Biol. Chem., Vol. 275: 4545-4548). Genomic DNA was isolated from mouse tail biopsies and analyzed by PCR using primers specific for the human GH poly(A)+ signal.

Plasmids and transfection assays. A 305 bp genomic fragment encompassing the miR-208 coding region was amplified by PCR and ligated into pCMV6. A 1 kb fragment encompassing the entire murine THRAP1-UTR was PCR-amplified and ligated into an HA-tagged pCMV6 expression construct and the firefly luciferase (flue) reporter construct (pMIR-REPORT™, Ambion). A mutation of the UCGUCUUA miR-208 seed binding sequence was constructed through PCR-based mutagenesis.

Example 1 miR-208 is Required for Expression of miR-499

Figure 14:
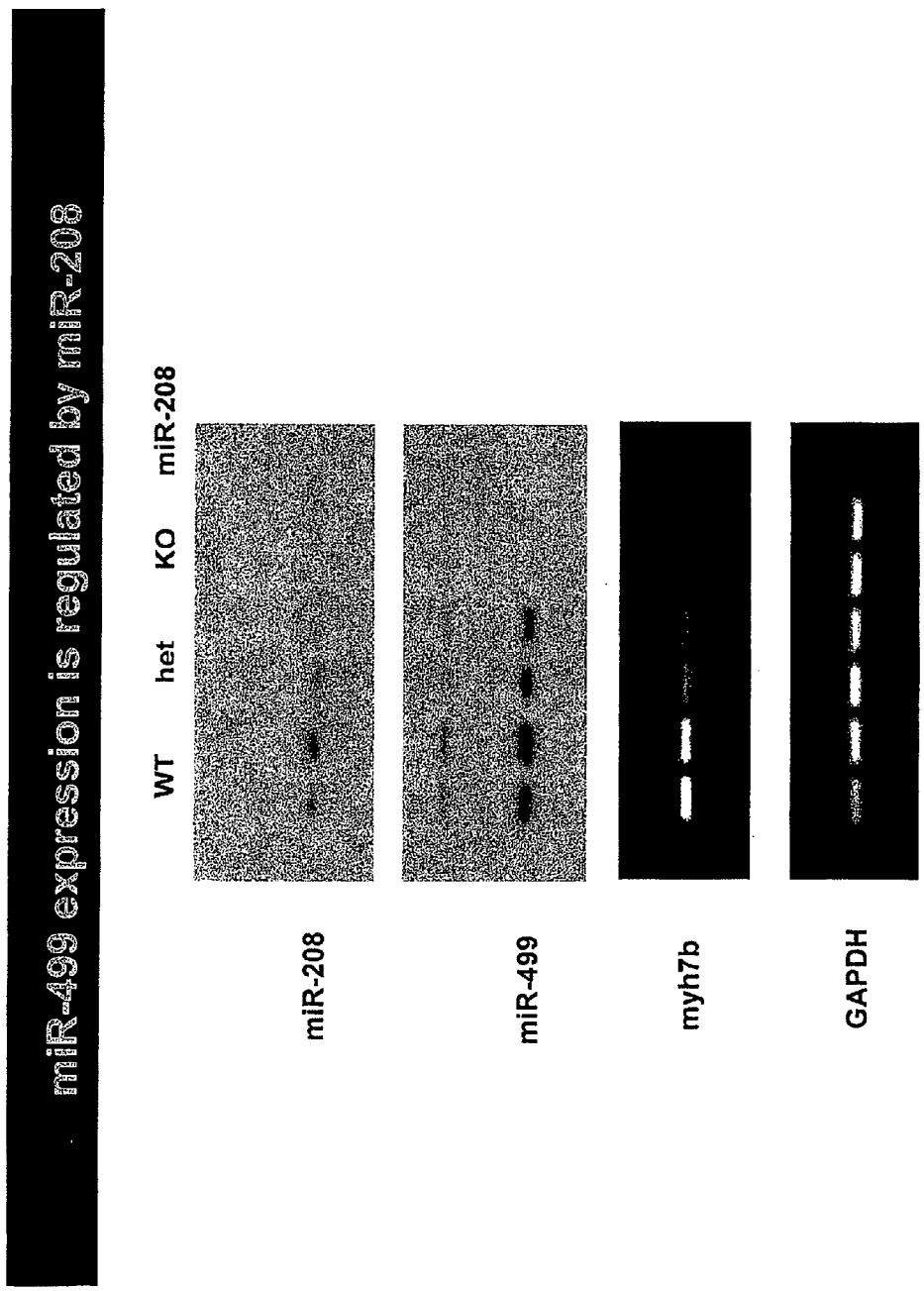
FIG. 14. Northern blot showing expression of miR-499 in hearts of wild-type, miR-208$^{-/-}$ and miR-208$^{-/-}$ mice. There is a direct correlation between the expression of miR-208 and miR-499, as well as Myh7b in wild-type and mutant mice.
Figure 16:
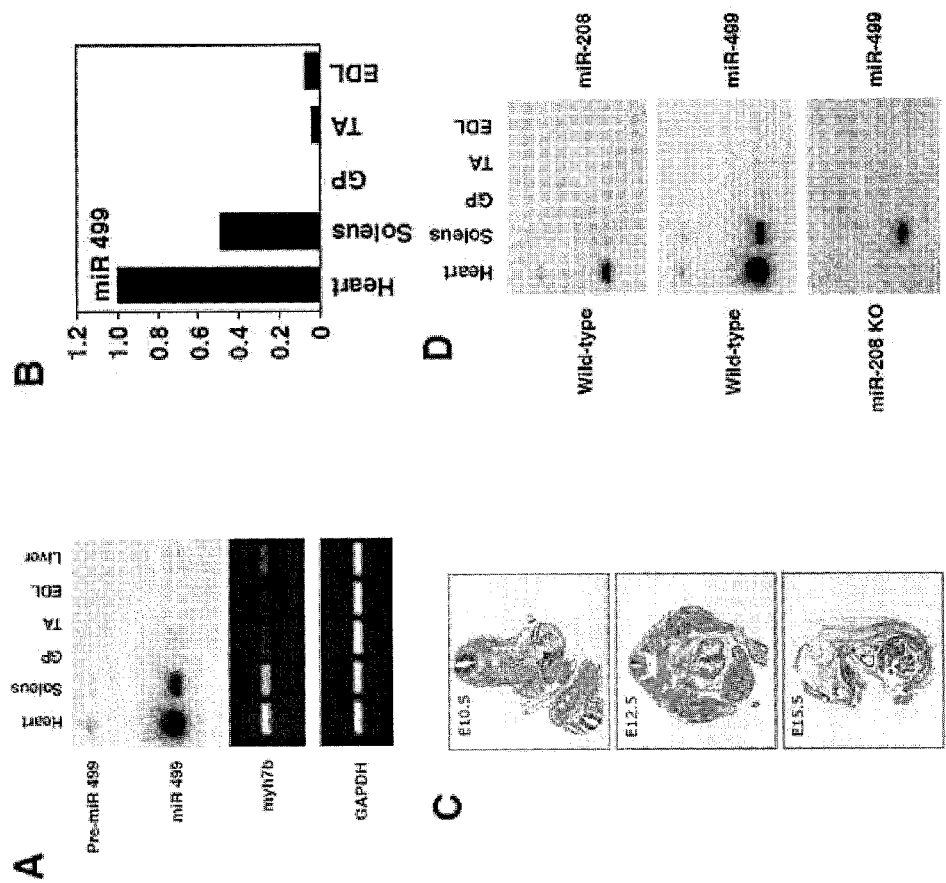
FIG. 16A-D. miR-208 regulates cardiac myh7b expression.
Figure 17:
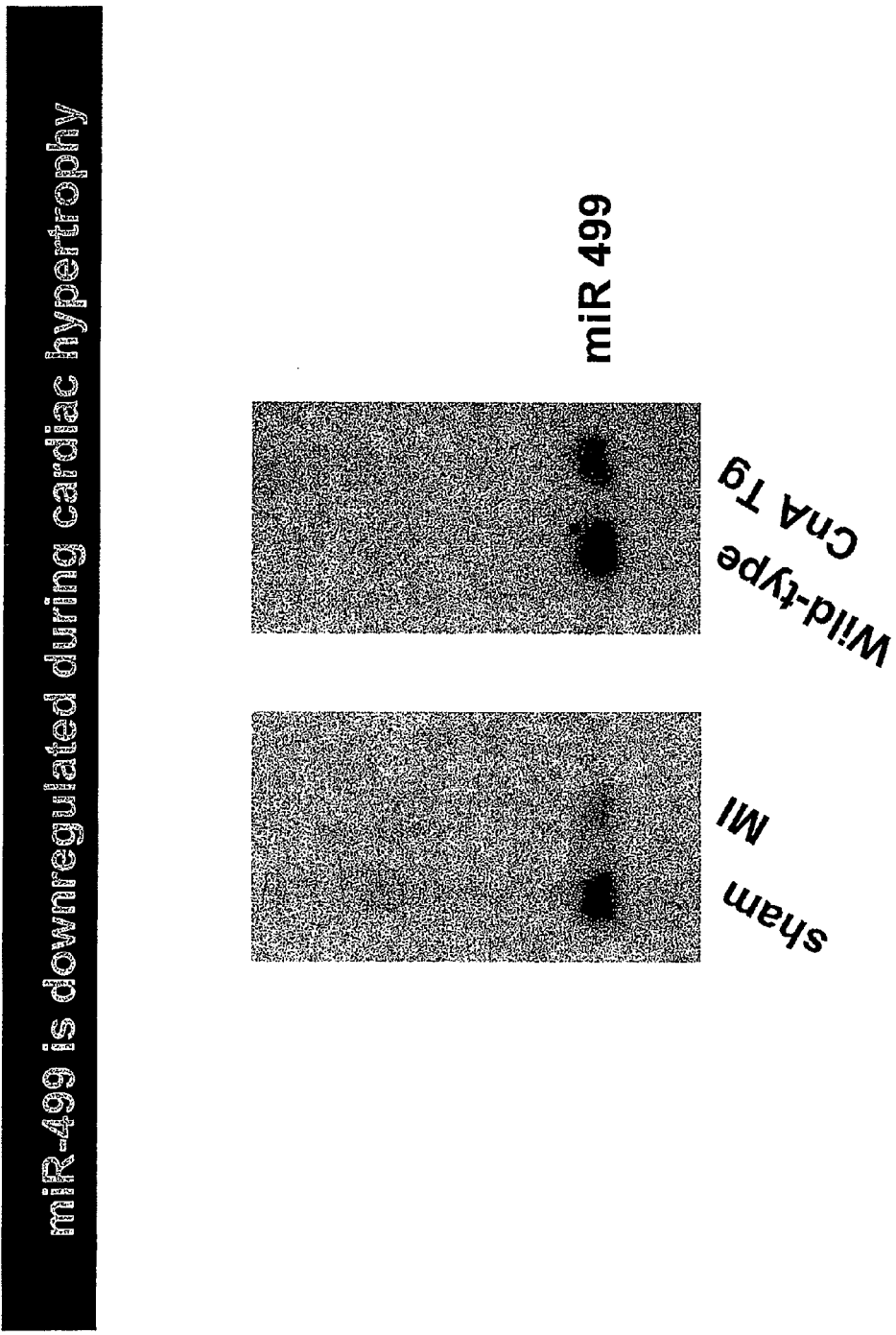
FIG. 17. Northern blot showing expression of miR-499 in wild-type mice with heart disease. MI, myocardial infarction. CnA Tg, calcineurin transgenic mice.

To further explore the mechanism of action of miR-208 in the heart, the inventors defined the microRNA expression patterns in hearts from wild type and miR-208 null mice by microarray analysis. Among several microRNAs that were up- and down-regulated in mutant hearts, the inventors discovered that miR-499 was highly abundant in normal hearts, but was not expressed above background levels in miR-208 mutants. These findings were confirmed by Northern blot (FIG. 14). Analysis of the genomic location of the miR-499 gene showed it to be contained within the $20^{th}$ intron of the Myh7b gene, a homolog of the α-MHC gene (FIG. 15). miR-208 appears to regulate Myh7b and thereby miR-499 expression at the level of transcription since RT-PCR for myh7b indicates that the mRNA of the host gene is dose-dependently abrogated in the absence of miR-208 (FIG. 14). The Myh7b gene is conserved in vertebrates and is expressed solely in the heart and slow skeletal muscle (e.g. soleus) (FIG. 16A). This expression pattern for miR-499 was confirmed by real-time PCR analysis for miR-499 (FIG. 16B). In situ hybridization using a probe directed against the 3' end of the Myh7b gene, indicated that this myosin was expressed in heart and somites as early as E10.5 (FIG. 16C). Genetic deletion of miR-208 specifically inhibits cardiac expression of miR-499 while leaving skeletal muscle expression intact (FIG. 16D). These data indicate that miR-208 is required to drive an additional myosin, Myh7b, which gives rise to related miR-499. In addition, miR-499 is down-regulated during cardiac hypertrophy (FIG. 17).

Example 2

MEF2 Regulates miR-499 Expression in Cardiac and Skeletal Muscle

Figure 37:
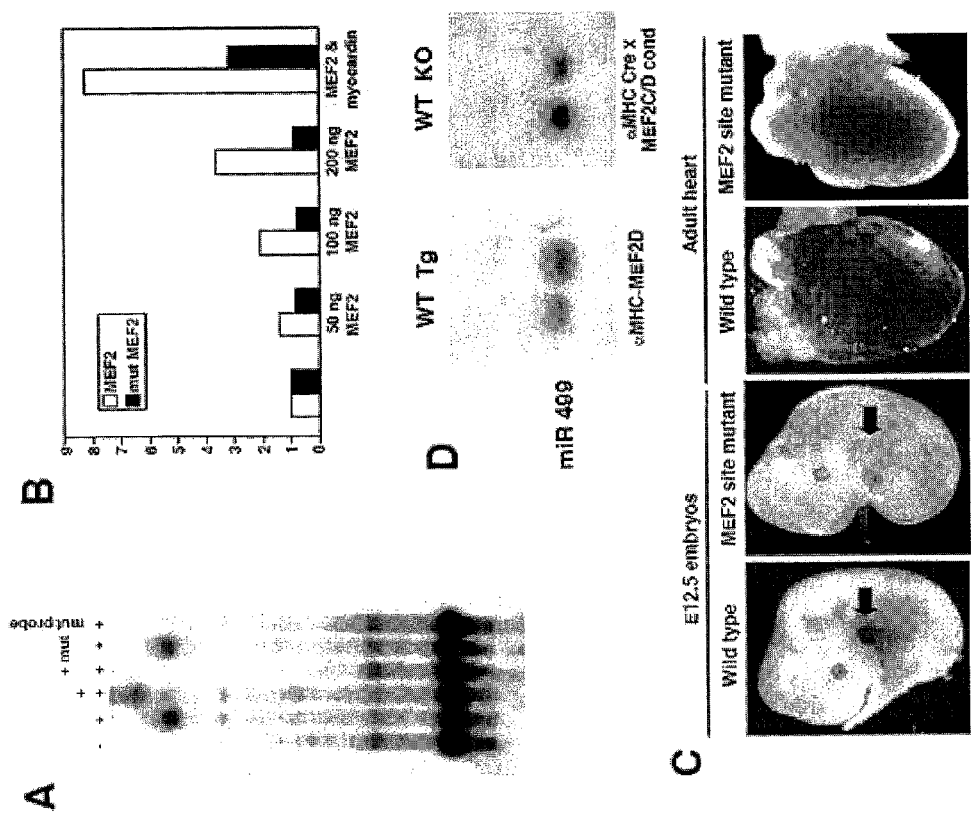
FIG. 37A-D. Myh7b/miR-499 expression is dependent on MEF2.

Within the 5' flanking region of the Myh7 gene, the inventors identified a potential MEF2 consensus sequence that was conserved across species. This sequence bound MEF2 avidly in gel mobility shift assays (FIG. 37A), and mutation of this sequence abolished both binding (FIG. 37A) and transcriptional activation of a luciferase reporter by MEF2 (FIG. 37B). The promoter region of the Myh7 gene was fused to a lacZ reporter and transgenic mice were generated. As shown in FIG. 37C, this genomic region was sufficient to direct lacZ expression specifically in the heart at E12.5. In the postnatal heart, lacZ staining was observed only in the ventricles, consistent with in situ hybridization (data not shown). Mutation of the MEF2 site completely eliminated expression of the lacZ transgene (FIG. 37C). Northern blot analysis on in vivo mouse models also showed the expression of miR-499 to be sensitive to MEF2. Cardiac-specific over-expression of MEF2D resulted in an increase in miR-499 expression, whereas cardiac deletion of both MEF2C and D caused a decrease in miR-499 expression (FIG. 37D). Direct binding of MEF2 to the promoter of Myh7b is required for the expression of Myh7b and miR-499 in vivo.

The MEF2 site is juxtaposed to a conserved E-box sequence (CANNTG), which serves as a binding site for members of the MyoD family of bHLH proteins that drive skeletal muscle gene expression with MEF2. Indeed, MyoD together with the ubiquitous bHLH protein E12 bound the E-box from the promoter. Mutation of this sequence prevented expression of the lacZ transgene in skeletal muscle, but did not affect expression in the heart.

Example 3

Identification of Targets for miR-499

Given the sequence homology between miR-208 and miR-499 and the inventors' previous data demonstrating that genetic disruption of miR-208 lead to a strong induction of specifically fast skeletal muscle genes and repression of β-MHC in the heart, it is likely that miR-499 has a comparable function in skeletal muscle and could act as a dominant regulator of fiber type. Expression of miR-499 and its host transcript are regulated by the myogenic transcription factor MEF2, a positive regulator of slow fiber gene expression and muscle endurance. The inventors suggest that the fiber type regulation of miR-499 is likely to be dependent on target genes of miR-499 involved in fiber type regulation.

MiR-208 is highly homologous to miR-499 and, the remarkable fact that both microRNAs are encoded by introns of Mhc genes, suggests that they share common regulatory mechanisms. Since miRNAs negatively influence gene expression in a sequence specific manner, the high degree of homology predisposes miR-208 and miR-499 to exert comparable functions due to overlap in target genes. The inventors have identified transcriptional regulators of MHC expression that appear to serve as targets of miR-499. They have also shown that miR-499 expression is controlled by miR-208 in the heart, such that knockdown of miR-208 eliminates miR-499 expression.

Figure 18:
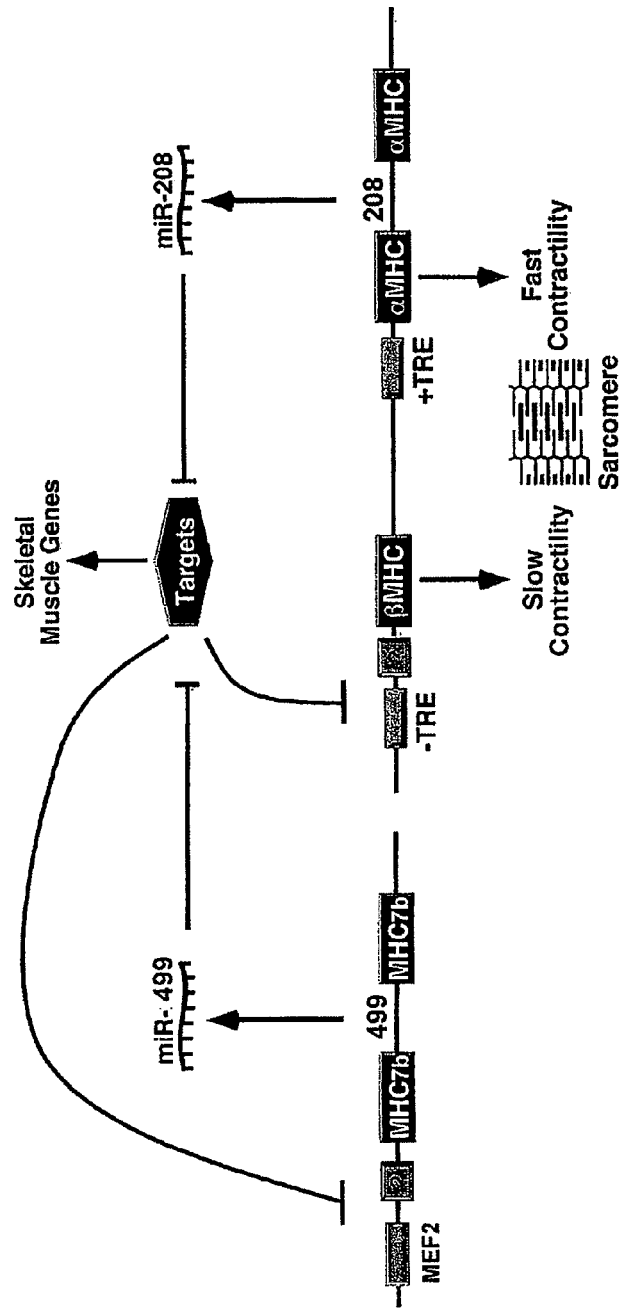
FIG. 18. Schematic diagram of the regulation of miR-499 by miR-208 in cardiac muscle.

Since the inventors' previous data demonstrated that genetic disruption of miR-208 leads to strong induction of specifically fast skeletal muscle genes in the heart, it is likely that miR-499 has a comparable function in skeletal muscle and could act as a dominant regulator of fiber type. In line with this hypothesis, promoter analysis of this transcript indicates that the expression of miR-499 and its host transcript are regulated by the myogenic transcription factor MEF2, a central regulator of skeletal muscle fiber type and slow fiber gene expression. The inventors have shown that MEF2 activity promotes muscle endurance and prevents muscle fatigue following prolonged exercise, and suggest that these actions of MEF2 are dependent, at least in part, on the direct activation of miR-499 expression (FIG. 18)

Figure 19:
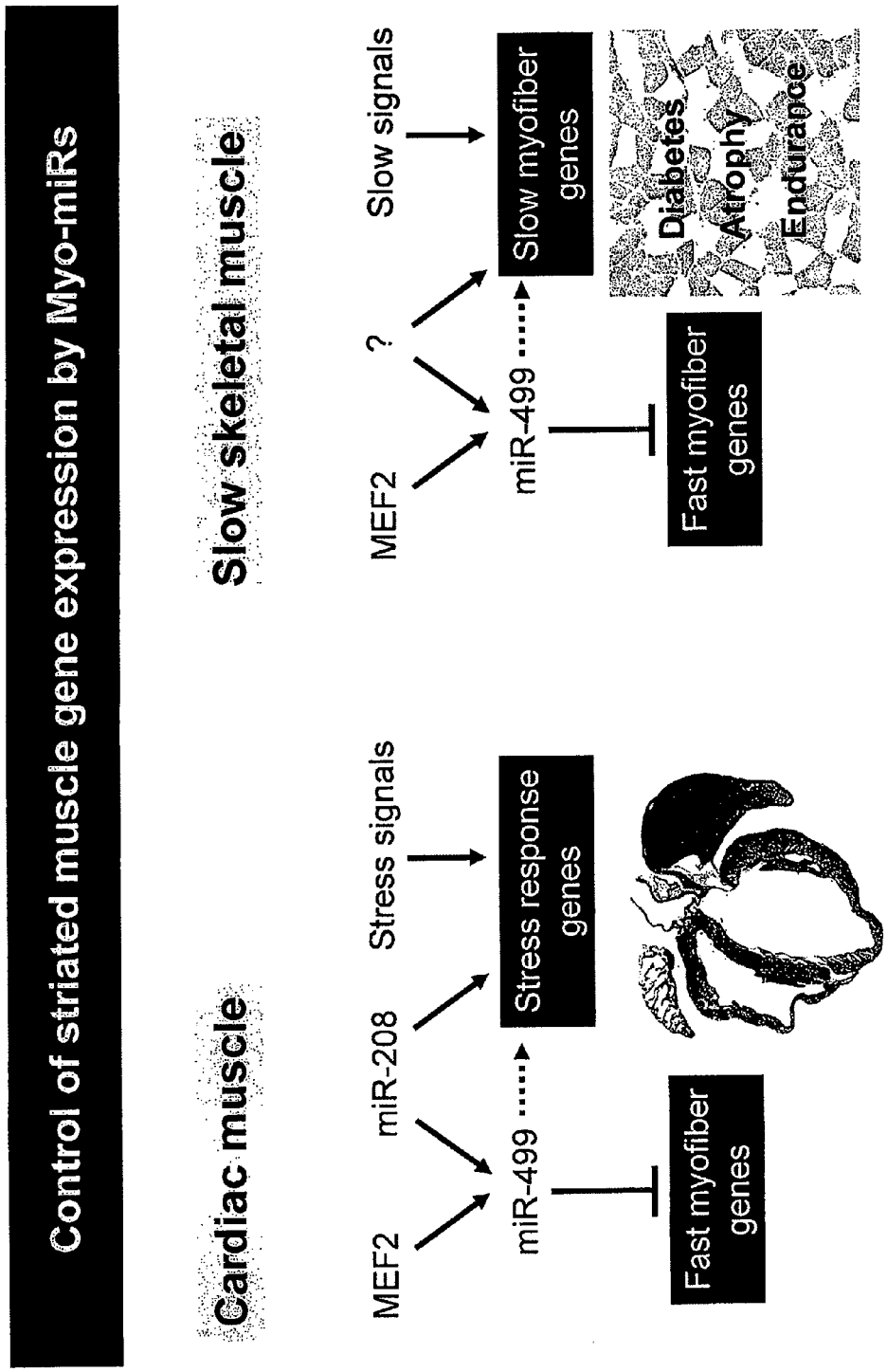
FIG. 19. Schematic diagram of the regulation of miR-499 by miR-208 in both cardiac and skeletal muscle.
Figure 20:
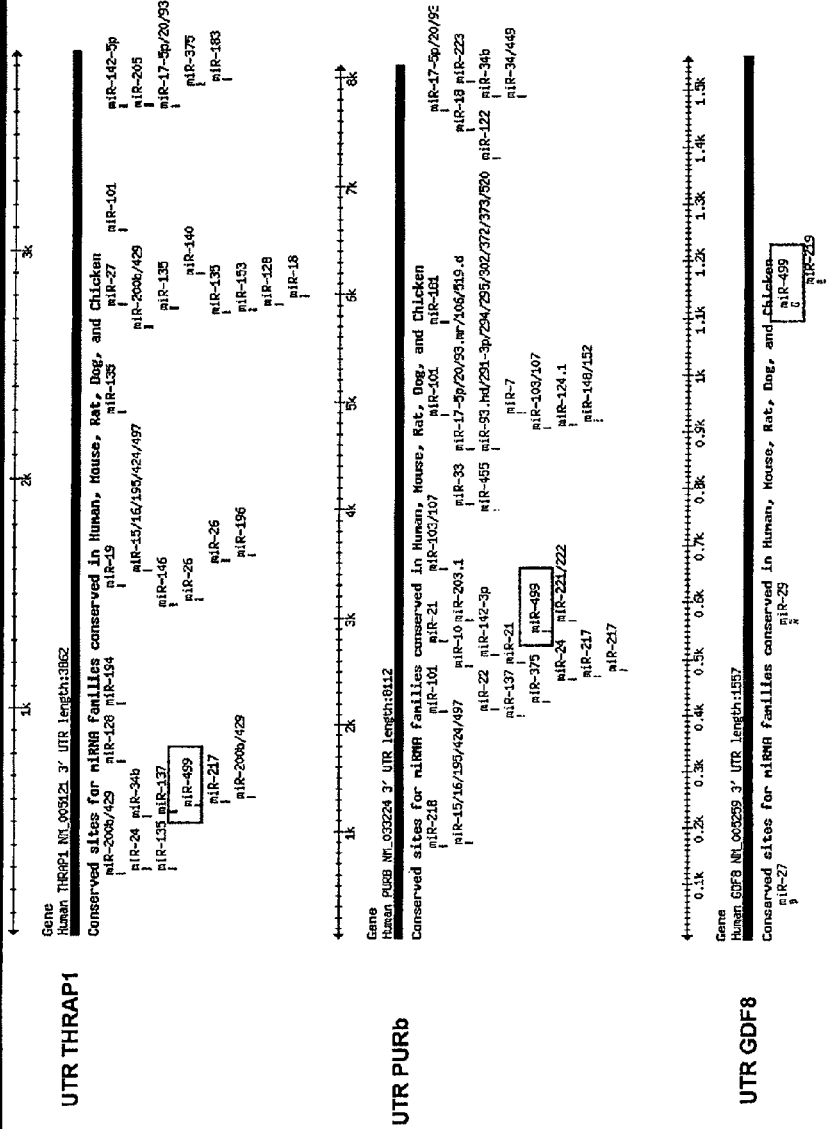
FIG. 20. miR-499 regulates myosin switching and fiber type identity by targeting THRAP1, PURbeta and GDF8 (a.k.a myostatin).
Figure 23:
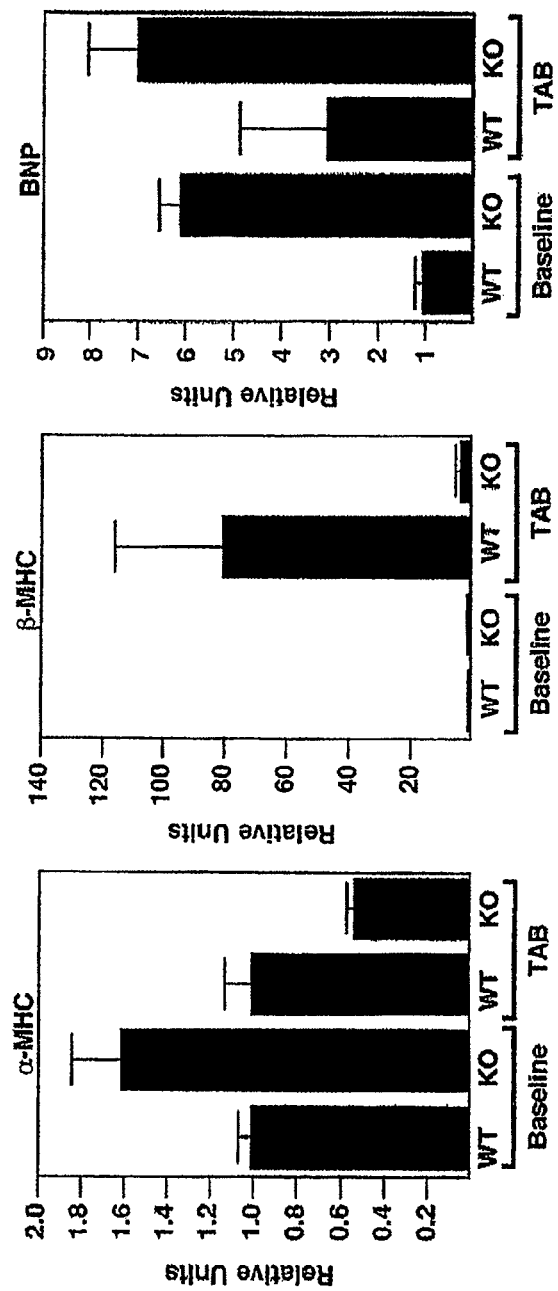
FIG. 23. Dysregulation of cardiac stress response genes in miR-208 knock-out mice.
Figure 24:
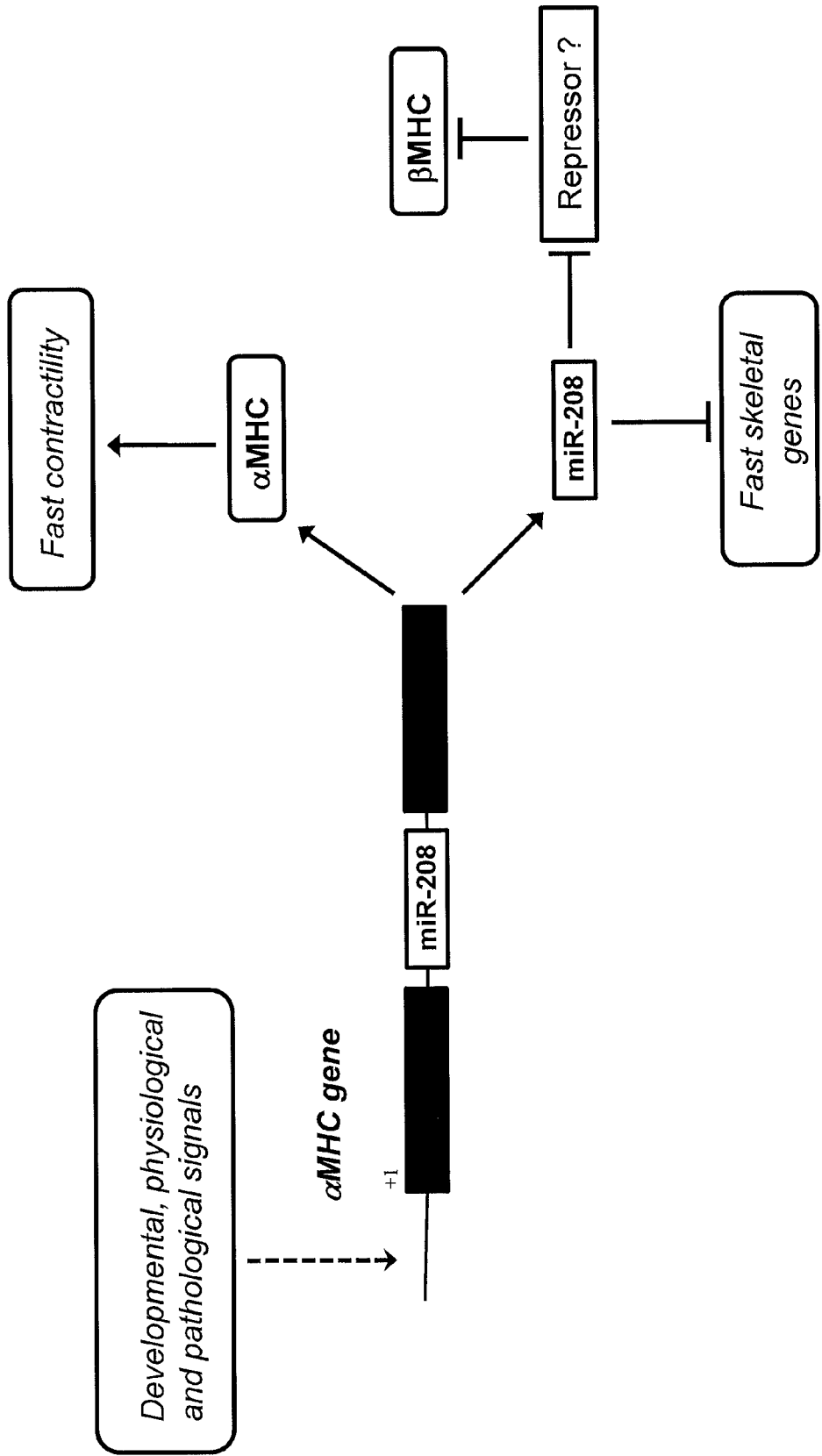
FIG. 24. A model for the role of miR-208 in cardiac gene regulation. The α-MHC gene encodes miR-208, which negatively regulates expression of THRAP1 and skeletal muscle genes among additional targets. The α- and β-MHC genes are linked and miR-208 is required for up-regulation of β-MHC in response to stress signaling and blockade to T3 signaling by PTU. α- and β-MHC promote fast and slow contractility, respectively.

These data indicate that the MEF2-regulated expression of the Myh7b gene additionally induces the expression of a slow muscle and cardiac specific miRNA, miR-499, which downregulates the expression of the fast skeletal muscle gene program. Further, these data provide evidence for miR-499 as a central regulator of skeletal muscle fiber type (FIG. 19). mRNA-499 is predicted to target THRAP1, PURbeta and GDF8 (aka myostatin), genes that are known to be crucial regulators of myosin expression and muscle fiber type, and are likely to be the effectors of miR-499 functionality in myofiber identity (FIG. 20). THRAP1 was previously identified to be targeted by miR-208 and regulates thyroid receptor signaling (van Rooij et al., 2007). Adult skeletal muscle retains the capability of transcriptional reprogramming. This attribute is readily observable in the non-weight-bearing (NWB) soleus muscle, which undergoes a slow-to-fast fiber type transition concurrent with decreased beta-myosin heavy chain (βMyHC) gene expression. This decrease in MyHC gene expression under NWB conditions is mediated by interactions between Sp3, Purα, and Purβ proteins. These data demonstrate that Pur proteins collaborate with Sp3 to regulate a transcriptional program that enables muscle cells to remodel their phenotype (Ji et al., 2007). Since miR-499 directly targets PURβ, the fiber type regulation might be mediated by targeting of PURβ. An additional target involved in muscle regulation is myostatin. Myostatin is a transforming growth factor-β family member that acts as a negative regulator of skeletal muscle growth. In mice, genetic disruption of the myostatin gene leads to a marked increase in body weight and muscle mass. Similarly, pharmacological interference with myostatin in vivo in mdx knockout mice results in a functional improvement of the dystrophic phenotype (Tang et al., 2007). Consequently, myostatin is an important therapeutic target for treatment of diseases associated with muscle wasting. Manipulating the functionality of miR-499 to regulate muscle specific fiber types could have far reaching implications for clinical pathologies, like muscular dystrophy. In addition, these results suggest that strategies to enhance slow fiber gene expression by elevating miR-499 expression will augment insulin sensitivity, endurance and other salutary aspects of the slow fiber gene program.

Example 4

MiR-208 is Counterbalanced by miR-208b

Figure 29:
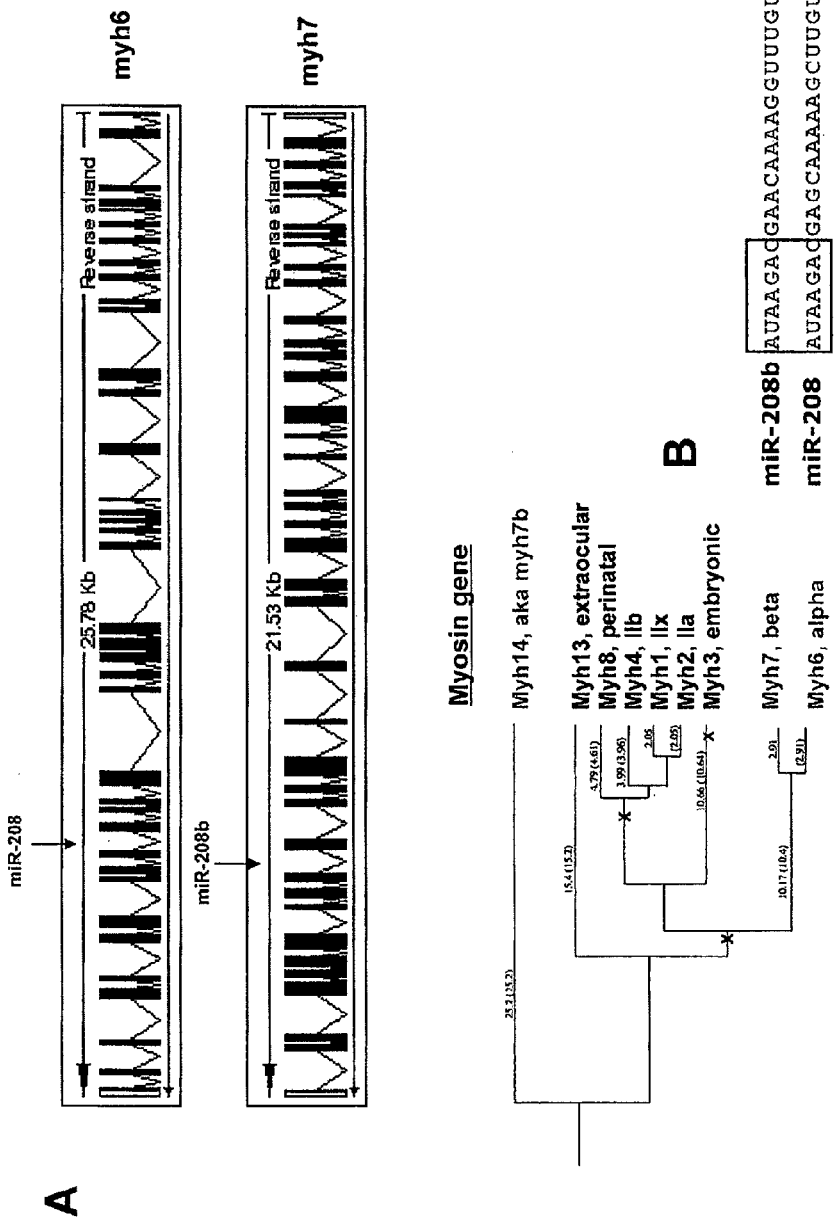
FIG. 29A-B. miR-208 and miR-208b developed due to a genomic duplication of the myosin heavy chain genes (myh6 and myh7, aka α-MHC and β-MHC). miR-208 and miR-208b are co-expressed with α-MHC and β-MHC (FIG. 29A) and share a homologous seed region although the total mature miR5 differ by 3 bases in sequence (FIG. 29B) (SEQ ID NO: 27 and SEQ ID NO: 5).
Figure 30:
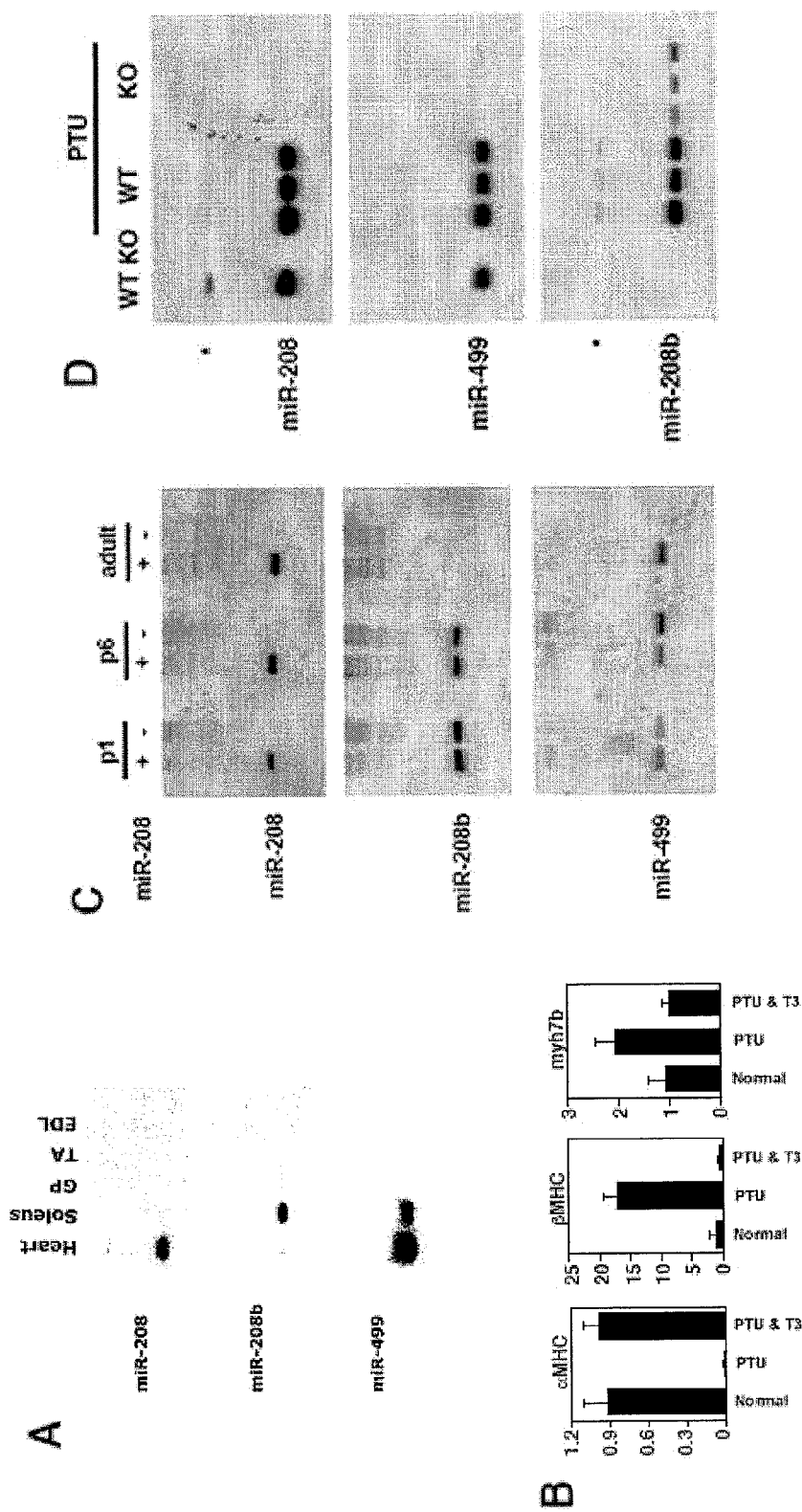
FIG. 30A-D. The myomiRs are co-expressed and co-regulated with their myosin host-gene.

Located within the β-MHC (a.k.a. myh7) gene is miR-208b, which is co-expressed with its host-gene (FIG. 28). The mature miR-208b sequence differs by 3 bases as compared to miR-208, but has an identical seed region. The homology between the two miRNAs and their host genes may have been the result of a genomic duplication that gave rise to α-MHC (myh6) and β-MHC (FIG. 29). Northern blot analysis was conducted to examine the expression pattern of miR-208b. At baseline, miR-208b shows a comparable expression pattern as its host gene (β-MHC), namely expression is predominantly observed in the soleus, a slow skeletal muscle, while little expression is observed in the heart and the fast skeletal muscle types (FIG. 30A).

Figure 31:
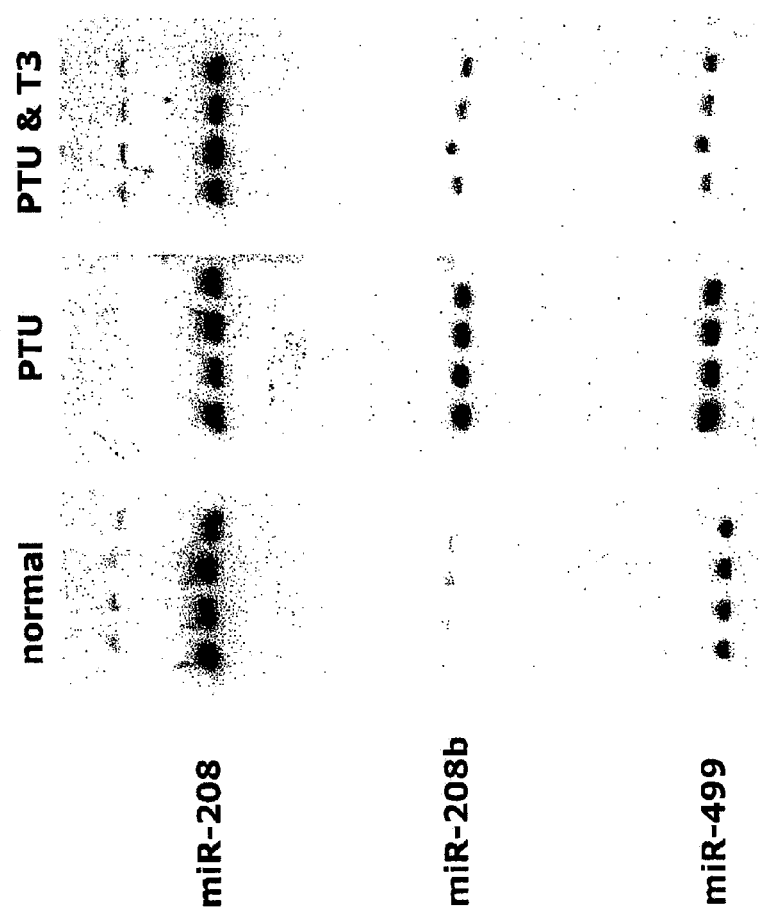
FIG. 31. Hypothyrodism with PTU treatment strongly induces miR-208b expression. Although miR-208b, like β-MHC, is hardly expressed in the heart under baseline conditions, its expression is strongly induced in response to hypothyrodism. This induction can be reversed by subsequent supplementation of thyroid hormone (T3).
Figure 32:
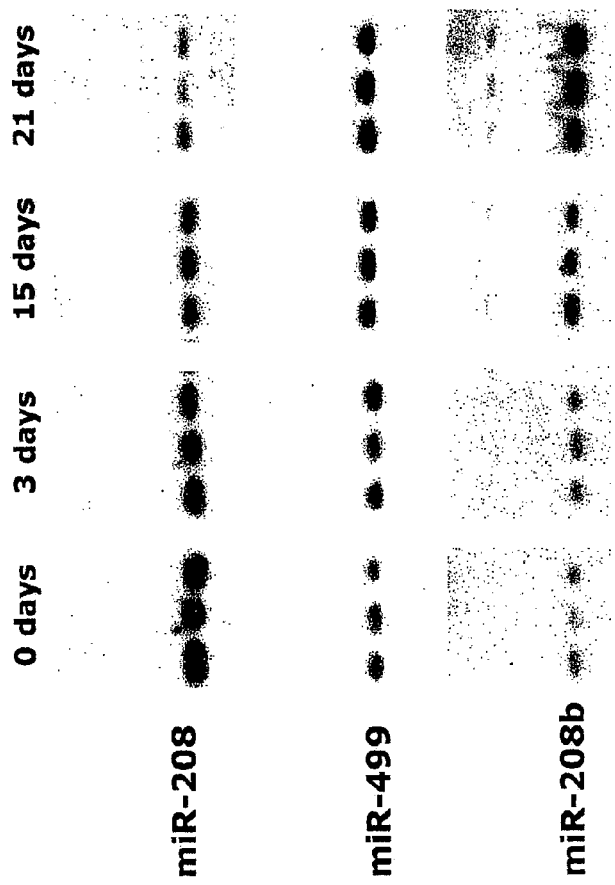
FIG. 32. Time-dependent induction of miR-208b during hypothyroidism with PTU treatment. Induction of miR-208b by PTU treatment is evident after 3 days. This PTU-induced expression of miR-208b increases with duration of PTU treatment.

Post-natally, T3 signaling induces α-MHC transcription via a positive T3 response element (TRE), whereas a negative TRE in the promoter of the β-MHC gene mediates transcriptional repression (Ojamaa et al. (2000) Endocrinology, Vol. 141: 2139-2144). To test the expression of miR-208, miR-208b, and miR-499 (i.e. myomiRs) in response to myosin regulation, rats were fed PTU-containing chow for 2 weeks to block T3 signaling, and subsequently supplemented PTU-treated rats with T3 to reverse the PTU effect. PTU, as expected, induced a decline in α-MHC and an increase in β-MHC in response to PTU, which could be reversed by T3 (FIG. 30B). Although to a lesser extent, the expression of myh7b followed the expression pattern of β-MHC; induced expression in response to PTU, and diminished expression in response to PTU together with T3 (FIG. 30B). Northern blot analysis indicates that miR-208b and miR-499 precisely followed the expression pattern of β-MHC and myh7b, respectively (FIG. 31). This increase appeared to be dose-dependent since longer exposure to PTU increased miR-208b expression over time (FIG. 32).

As α- and β-MHC are counterbalanced in the heart, the expression of miR-208/miR-208b is likely maintained at relatively constant levels. While β-MHC in mice is the dominant MHC gene expressed during embryogenesis and shortly after birth, α-MHC takes over during adulthood. Since the inventors' previous data indicated that miR-208 in the adult heart was required for miR-499 expression, the inventors tested whether miR-208b can substitute for miR-208. Northern analysis for the myomiRs at p1, p6 and in adult heart indicated that in the absence of miR-208, miR-499 remains expressed while miR-208b is present (FIG. 30C). To test whether miR-208b also responds to myosin switching in a comparable way as β-MHC, both wild-type and miR-208 mutant animals were treated with PTU. In response to PTU, α-MHC expression was severely repressed, which resulted in a loss of pre-miRNA-208 (indicated by asterisks) in wild-type animals. As expected, miR-499 was completely absent in the miR-208 mutant animals and only slightly induced in response to PTU in wild-type animals. However, miR-208b, like β-MHC, was strongly induced by PTU, while in the absence of miR-208, this induction was only minor (FIG. 30D). Together, these results suggest that the myomiRs located within the myosin genes regulate the expression levels of the myosin genes and therefore the miRNAs they harbor.

Figure 34:
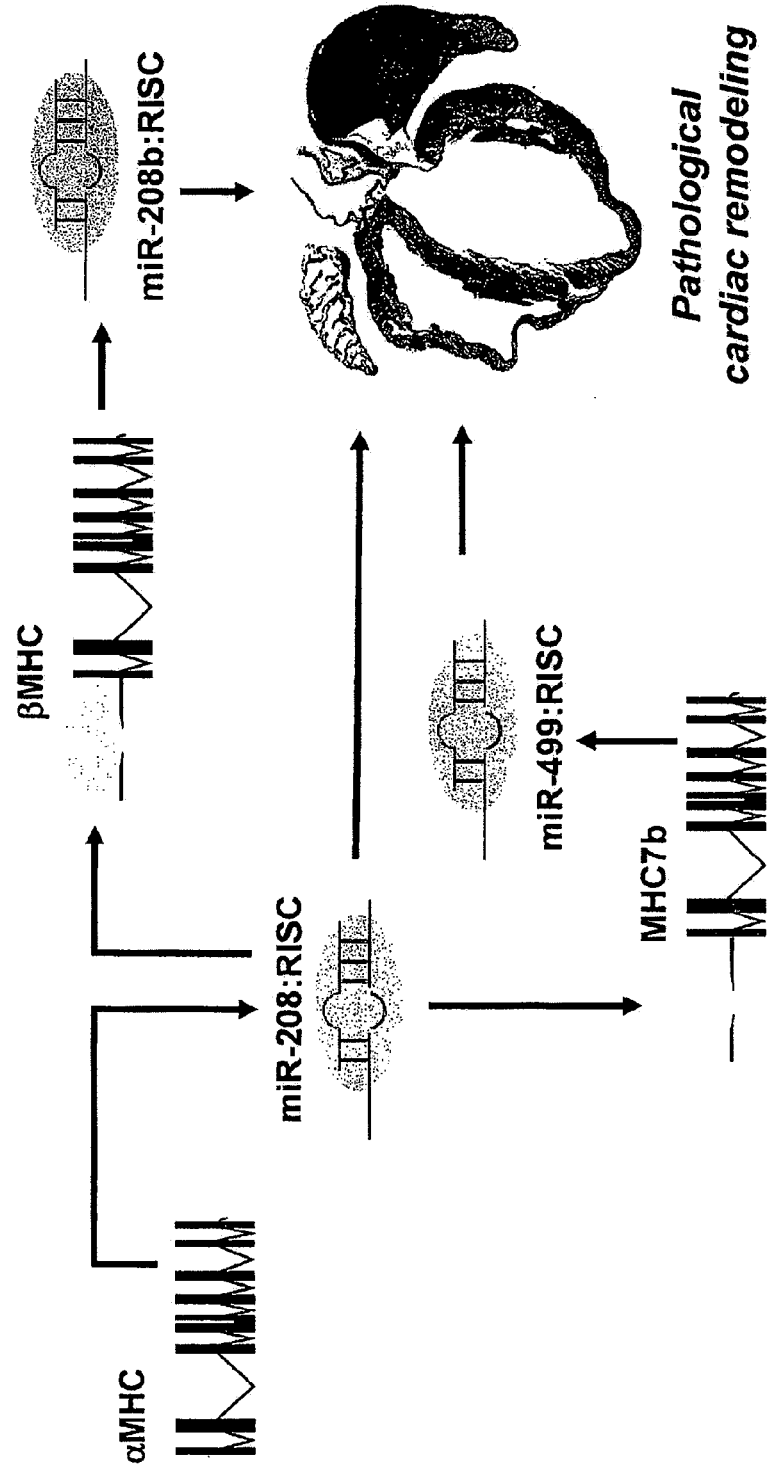
FIG. 34. Schematic model of miR-208 regulation of cardiac remodeling. miR-208 regulates cardiac remodeling either directly or indirectly through the regulation of miR-499 and miR-208b expression.

Previously the inventors showed that cardiac specific deletion of miR-208 inhibited the induction of β-MHC expression by stress stimuli (FIG. 8). Although β-MHC expression is very low at baseline, Northern blotting for miR-208b showed a dose-dependent decrease in miR-208b expression corresponding to the removal of one or both miR-208 alleles (FIG. 33A). However, transgenic overexpression of miR-208, which has been shown to induce β-MHC expression (FIG. 9), induced miR-208b expression (FIG. 33B). These data imply that although miR-208 appears to be the upstream regulator of the effect on cardiac β-MHC expression, pathological cardiac remodeling may also be due to the regulation of miR-499 and miR-208b (FIGS. 33C and 34).

Example 5

MiR-208 and miR-499 Repress the Fast Skeletal Muscle Phenotype

Figure 38:
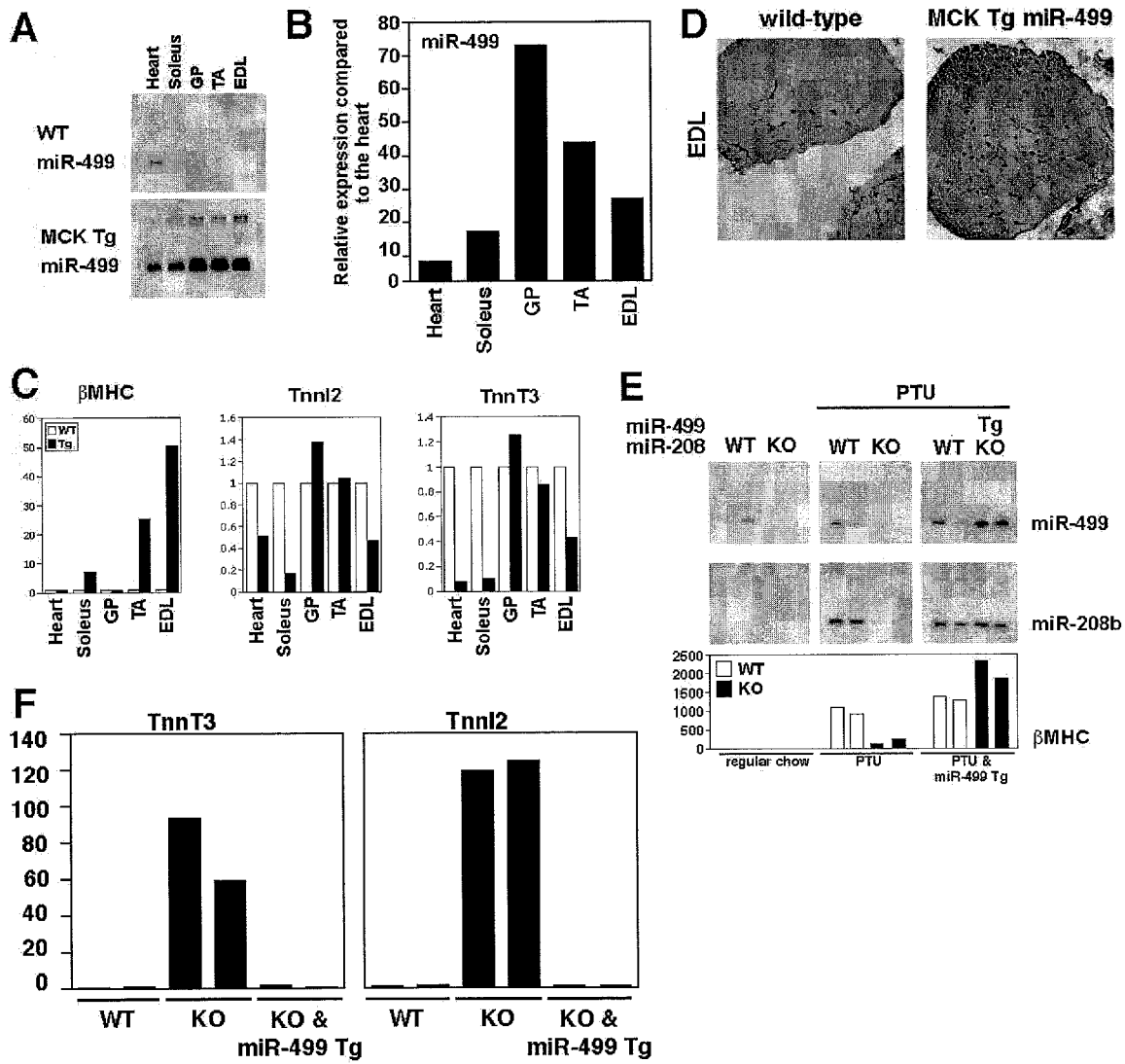
FIG. 38A-F. miR-499 regulates the expression of β-MHC and fast skeletal genes.

The up-regulation of fast skeletal muscle genes in hearts of miR-208 null mice, combined with the slow fiber-specific expression of miR-499 suggested that these miRNAs may function to repress the expression of fast skeletal muscle genes. To address this issue, transgenic mice were generated that expressed miR-499 in fast skeletal muscle under control of the MCK promoter and enhancer. Multiple stable transgenic lines were obtained that expressed miR-499 in fast fibers (FIG. 38A). Compared to cardiac expression, these transgenic animals efficiently overexpressed miR-499 in soleus and fast skeletal muscle types (FIG. 38B). Analysis of fiber type-specific gene expression showed that fast fibers were transformed toward a slow myofiber phenotype by the forced expression of miR-499. Gene expression analysis in all five muscle types in both wild-type and miR-499 transgenic animals indicated that miR-499 is sufficient to drive β-MHC expression in soleus, TA and EDL, while miR-499 represses the fast skeletal troponin I and T in heart, soleus and EDL (FIG. 38C). Fast muscle fibers of these transgenic animals were readily identifiable by their deep red color, indicative of high levels of myoglobin expression and vascularization. Similarly, metachromatic ATPase staining of histological sections showed a dramatic increase in slow myofiber gene expression in fast fibers (EDL) of the transgenic mice (FIG. 38D).

To determine whether the loss of miR-499 in the miR-208 knockout animals was in series or in parallel with the regulation of β-MHC and the fast skeletal genes, miR-499 was transgenically overexpressed in the miR-208 null background. Northern blot analysis and realtime PCR for β-MHC indicates that PTU potently induces β-MHC and miR-208b in wild-type (WT) animals but not in miR-208 mutant animals (KO). However, re-introduction of miR-499 by transgenic overexpression abolishes this repressive effect on β-MHC in the absence of miR-208 (FIG. 38E). Also, the induced expression of fast skeletal troponins in the absence of miR-208 is repressed in the presence of the miR-499 transgene (FIG. 38F). These data indicate that miR-499 is sufficient to drive a slow skeletal fiber phenotype and is responsible for the effects on β-MHC and fast skeletal genes in the miR-208 mutant animals.

Figure 27:
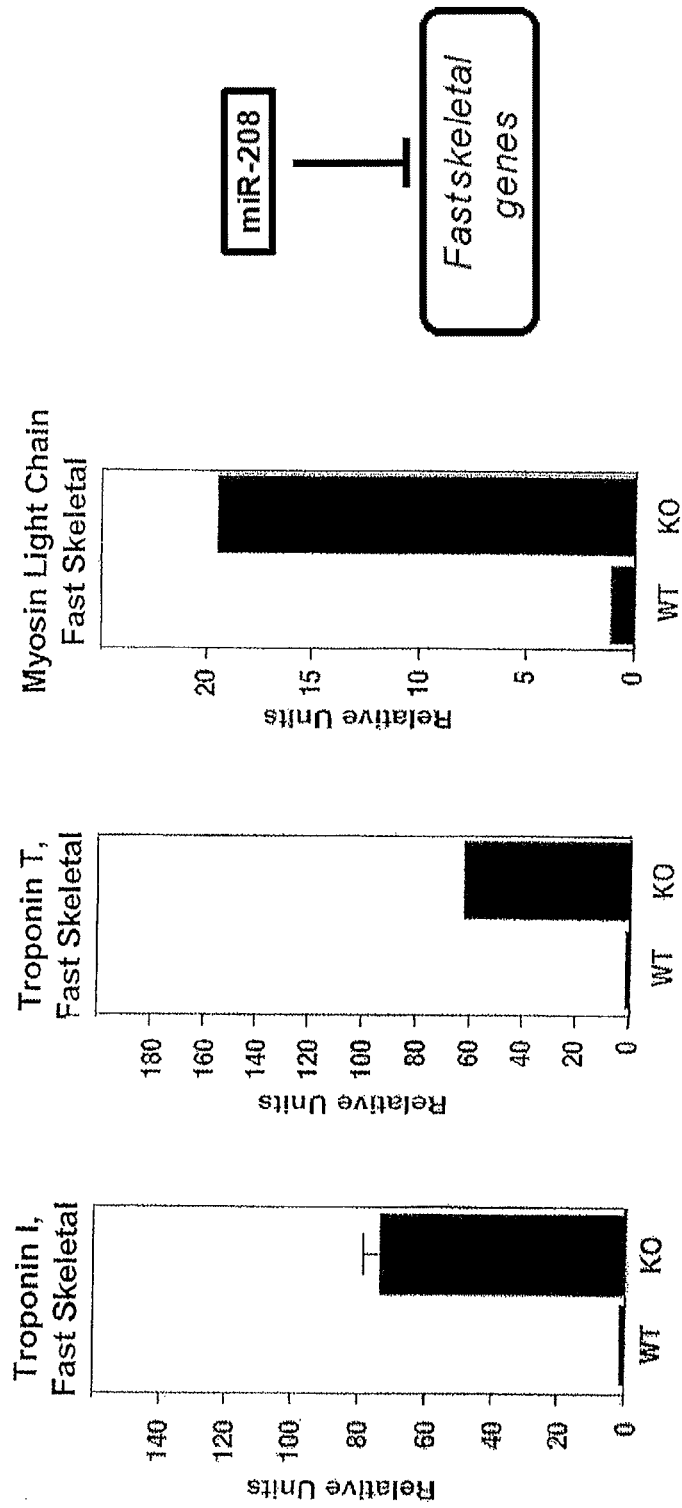
FIG. 27. Up-regulation of fast skeletal muscle genes in hearts of miR 208 mutant mice.
Figure 36:
FIG. 36. Schematic of a transgenic mouse model overexpressing binding site regions for both miR-499 and miR-208b. Skeletal muscle specific overexpression of binding site regions for both miR-499 and miR-208b using a skeletal and heart muscle specific promoter (muscle creatine kinase (MCK)) should scavenge miR-208b and miR-499 in both heart and skeletal muscle, thereby generating a knockdown for both miRNAs (SEQ ID NOS: 5, 26 and 27).

Since miR-208b is expressed in slow skeletal muscle, it is very likely that it regulates fiber type identity in skeletal muscles either directly or through regulation of miR-499. Previous data showed that cardiac removal of miR-208 (a cardiac family member of miR-208b) resulted in a cardiac inhibition of miR-499 and an upregulation of fast skeletal muscle genes (FIGS. 22 and 27). Removal of miR-208b from skeletal muscle will likely inhibit miR-499 expression and produce an expression of fast skeletal muscle genes, thereby inducing a fiber type shift from slow towards fast. To investigate the functional implications of miR-208b in more detail, a targeting strategy was designed to very precisely remove miR-208b from the mouse genome (FIG. 35). An additional approach to scavenge both miR-499 and miR-208b may also be undertaken. Skeletal muscle specific overexpression of binding site regions for both miR-499 and miR-208b using a skeletal and heart muscle specific promoter (muscle creatine kinase (MCK)) should scavenge miR-208b and miR-499 in both heart and skeletal muscle, thereby generating a knockdown for both miRNAs (FIG. 36).

Example 6

Control of Myh7b/miR-499 by miR-208

In the heart, miR-208 is the upstream regulator of a system responsible for maintaining cardiomyocyte identity by repressing fast skeletal gene expression and, in addition, contributes to pathological remodeling in response to stress. miR-208 does so, at least in part, by regulating the expression of an additional miRNA, miR-499, which is located within the myosin gene myh7b. Although miR-208 is absent in skeletal muscle, a closely related miR, miR-208b, is expressed in slow skeletal muscle from the β-MHC transcript.

Based on the restricted expression of miR-499 to slow skeletal muscle fibers, miR-208b may induce miR-499 to repress the fast fiber gene program in slow skeletal muscles. However, our data indicate that miR-499 is required for β-MHC expression, which would generate a feed-forward loop in which β-MHC, through activation of miR-208b and miR-499, stimulates its own expression.

It is remarkable that a 50% reduction in miR-208 expression in hearts of miR-208+/− mice results in a corresponding decrease in Myh7b/miR-499 expression and the absence of miR-208 completely eliminates expression of Myh7b/miR-499. The sensitivity of Myh7b/miR-499 to the level of miR-208 expression suggests that the target(s) of miR-208 are precisely regulated, which is exceptional since miRNAs usually are thought of as fine-tuners of gene expression rather than on-off switches.

The inventors previously determined THRAP1, a thyroid hormone receptor co-regulator, to be a target of miR-208. Due to the significant overlap in seed sequence between miR-208 and miR-499, these miRNAs may have overlapping targets. Thus, miR-499 may regulate THRAP1 and thereby control β-MHC and fast skeletal gene expression. In addition to THRAP1, Sox6, a member of the Sox family of transcription factors, might also contribute to the phenotype. Sox6, which is highly expressed in skeletal muscle and known to negatively regulate β-MHC expression in cardiac and skeletal muscle, contains multiple conserved miR-499 binding sites in its 3' UTR and represents a likely mediator of the effects of miR-499 on muscle gene expression.

Example 7

Regulation of Cardiac Remodeling by miR-208 and miR-499

The most remarkable function of miR-208 was revealed by the aberrant response of miR-208 null mice to cardiac stress (von Rooij et al. (2007) Science, Vol. 316: 575-579). In response to pressure overload by thoracic aortic constriction or signaling by calcineurin, miR-208 null mice showed virtually no hypertrophy or fibrosis and were unable to up-regulate βMHC expression. In contrast, other stress responsive genes, such as those encoding ANF and BNP, were strongly induced in miR-208 mutant animals, demonstrating that miR-208 is dedicated specifically to the control of β-MHC expression, which can be uncoupled from other facets of the cardiac stress response. Since the inventors' data indicate that miR-499 is responsible for some of the gene regulatory effects seen in the miR-208 mutant animals, miR-499 mutant animals may also be resistant to pathological remodeling of the heart, like miR-208 mutant animals. The absence of both miR-208 and miR-499 may be induce the protective effect.

As alpha- and beta-MHC are counterbalanced in the heart, the expression of miR-208/miR-208b is likely maintained at relatively constant levels. However, while alpha-MHC is the dominant MHC isoform in mice and beta-MHC dominates in humans, the relative expression of miR-208 versus miR-208b differs accordingly in mice versus humans. Since miR-208 is required for cardiac beta-MHC expression in response to stress and hypothyroidism in mice, miR-208b may play an important role in the human shift towards beta-MHC during heart disease. Nonetheless, these data indicate that there must exist an intimate form of cross-talk between these miRNAs and the myosin genes. Manipulating the functionality of miR-208b to regulate muscle specific fiber types can have far reaching implications for clinical pathologies, like muscular dystrophy. In addition, these results suggest that strategies to enhance slow fiber gene expression by elevating miR-208b expression will augment insulin sensitivity, endurance and other salutary aspects of the slow fiber gene program.

\* \* \*

All publications, patents and patent applications discussed and cited herein are incorporated herein by reference in their entireties. All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods, and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

References

The following references, to the extent that they provide exemplary procedural or other details supplementary to those set forth herein, are specifically incorporated herein by reference.

U.S. Pat. No. 4,873,191
U.S. Pat. No. 5,604,251
U.S. Pat. No. 5,844,107
U.S. Pat. No. 5,877,302
U.S. Pat. No. 5,972,900
U.S. Pat. No. 5,972,901
U.S. Pat. No. 6,008,336
U.S. Pat. No. 6,077,835
U.S. Pat. No. 6,200,801
U.S. Publn. 20020150626
U.S. Publn. 20030032615
U.S. Publn. 20030203865
U.S. Publn. 20040048787
Abraham et al., *Mol. Med.*, 8:750-760, 2002.
Ambros, *Cell*, 113(6):673-676, 2003.
Angel et al., *Cell*, 49:729, 1987b.
Angel et al., *Mol. Cell. Biol.*, 7:2256, 1987a.
Atchison and Perry, *Cell*, 46:253, 1986.
Atchison and Perry, *Cell*, 48:121, 1987.
Baichwal and Sugden, In: *Gene Transfer*, Kucherlapati (Ed.), Plenum Press, NY, 117-148, 1986.
Baldwin and Haddad, J. *Appl. Physiol.*, 90:345-357, 2001.
Banerji et al., *Cell*, 27(2 Pt 1):299-308, 1981.
Banerji et al., *Cell*, 33(3):729-740, 1983.
Barnes et al., *J. Biol. Chem.*, 272(17):11510-11517, 1997.
Bartel, *Cell*, 116:281-297, 2004.
Benvenisty and Neshif, *Proc. Natl. Acad. Sci. USA*, 83(24):9551-9555, 1986.
Berkhout et al., *Cell*, 59:273-282, 1989.
Bhavsar et al., *Genomics*, 35(1):11-23, 1996.
Blanar et al., *EMBO J.*, 8:1139, 1989.
Bodine and Ley, *EMBO J.*, 6:2997, 1987.
Boshart et al., *Cell*, 41:521, 1985.
Bosze et al., *EMBO J.*, 5(7):1615-1623, 1986.
Braddock et al., *Cell*, 58:269, 1989.
Brennecke et al., *Cell*, 113:25-36, 2003.
Brinster et al., *Proc. Natl. Acad. Sci. USA*, 82(13):4438-4442, 1985.
Bristow, *Cardiology*, 92:3-6, 1999.
Bulla and Siddiqui, *J. Virol.*, 62:1437, 1986.
Calin et al., *Proc. Natl. Acd. Sci. USA*, 99:15524-15529, 2002.
Campbell and Villarreal, *Mol. Cell. Biol.*, 8:1993, 1988.
Campere and Tilghman, *Genes and Dev.*, 3:537, 1989.
Campo et al., *Nature*, 303:77, 1983.
Carrington et al. *Science*, 301(5631):336-338, 2003.
Celander and Haseltine, *J. Virology*, 61:269, 1987.
Celander et al., *J. Virology*, 62:1314, 1988.
Chandler et al., *Cell*, 33:489, 1983.
Chang and Karin, *Nature*, 410(6824):37-40, 2001.
Chang et al., *Biochim. Biophys. Acta*, 1092(2):153-160, 1991.
Chang et al., *Mol. Cell. Biol.*, 9:2153, 1989.
Chang et al., *Nature*, 430(7001):785-789, 2004.
Chatterjee et al., *Proc. Natl. Acad. Sci. USA*, 86:9114, 1989.
Chen and Okayama, *Mol. Cell. Biol.*, 7(8):2745-2752, 1987.
Chen et al., *Science*, 303(5654):83-86, 2004.
Choi et al., *Cell*, 53:519, 1988.
Coffin, In: *Virology*, Fields et al. (Eds.), Raven Press, NY, 1437-1500, 1990.
Cohen et al., *J. Cell. Physiol.*, 5:75, 1987.
Costa et al., *Mol. Cell. Biol.*, 8:81, 1988.
Couch et al., *Am. Rev. Resp. Dis.*, 88:394-403, 1963.
Coupar et al., *Gene*, 68:1-10, 1988.
Cripe et al., *EMBO J.*, 6:3745, 1987.
Culotta and Hamer, *Mol. Cell. Biol.*, 9:1376, 1989.
Dandolo et al., *J. Virology*, 47:55-64, 1983.
De Villiers et al., *Nature*, 312(5991):242-246, 1984.
Deschamps et al., *Science*, 230:1174-1177, 1985.
Dubensky et al., *Proc. Natl. Acad. Sci. USA*, 81:7529-7533, 1984.
Durand et al., *Ann. Med.*, 27:311-317, 1995.
Edbrooke et al., *Mol. Cell. Biol.*, 9:1908, 1989.
Edgerton and Roy, *J. Appl. Physiol.*, 89:1224-1231, 2000.
Edlund et al., *Science*, 230:912-916, 1985.
Eichhorn and Bristow, *Circulation*, 94:2285-2296, 1996.
EPO 0273085
Fatkin et al., *J. Clin. Invest.*, 106:1351-1359, 2000.
Fechheimer, et al., *Proc Natl. Acad. Sci. USA*, 84:8463-8467, 1987.
Feng and Holland, *Nature*, 334:6178, 1988.
Ferkol et al., *FASEB J.*, 7:1081-1091, 1993.
Firak and Subramanian, *Mol. Cell. Biol.*, 6:3667, 1986.
Fitts et al., *J. Appl. Physiol.*, 89:823-839, 2000.
Foecking and Hofstetter, *Gene*, 45(1):101-105, 1986.
Fraley et al., *Proc. Natl. Acad. Sci. USA*, 76:3348-3352, 1979.

Franz et al., *Cardioscience*, 5(4):235-43, 1994.
Friedman et al., *Genes Devel.*, 3:1314, 1989.
Fujita et al., *Cell*, 49:357, 1987.
Ghosh and Bachhawat, In: *Liver Diseases, Targeted Diagnosis and Therapy Using Specific Receptors and Ligands*, Wu et al. (Eds.), Marcel Dekker, NY, 87-104, 1991.
Ghosh-Choudhury et al., *EMBO J.*, 6:1733-1739, 1987.
Gilles et al., *Cell*, 33:717, 1983.
Gloss et al., *EMBO J.*, 6:3735, 1987.
Godbout et al., *Mol. Cell. Biol.*, 8:1169, 1988.
Gomez-Foix et al., *J. Biol. Chem.*, 267:25129-25134, 1992.
Goodbourn and Maniatis, *Proc. Natl. Acad. Sci. USA*, 85:1447, 1988.
Goodbourn et al., *Cell*, 45:601, 1986.
Gopal, *Mol. Cell. Biol.*, 5:1188-1190, 1985.
Gopal-Srivastava et al., *J. Mol. Cell. Biol.* 15(12):7081-7090, 1995.
Graham and Prevec, In: *Methods in Molecular Biology: Gene Transfer and Expression Protocol*, Murray (Ed.), Humana Press, Clifton, N.J., 7:109-128, 1991.
Graham and Van Der Eb, *Virology*, 52:456-467, 1973.
Graham et al., *J. Gen. Virl.*, 36(1):59-74, 1977.
Greene et al., *Immunology Today*, 10:272, 1989
Grishok et al., *Cell*, 106:23-34, 2001.
Grosschedl and Baltimore, *Cell*, 41:885, 1985.
Grunhaus and Horwitz, *Seminar in Virology*, 3:237-252, 1992.
Harland and Weintraub, *J. Cell Biol.*, 101(3):1094-1099, 1985.
Haslinger and Karin, *Proc. Natl. Acad. Sci. USA*, 82:8572, 1985.
Hauber and Cullen, *J. Virology*, 62:673, 1988.
Hen et al., *Nature*, 321:249, 1986.
Hensel et al., *Lymphokine Res.*, 8:347, 1989.
Hermonat and Muzycska, *Proc. Natl. Acad. Sci. USA*, 81:6466-6470, 1984.
Herr and Clarke, *Cell*, 45:461, 1986.
Hersdorffer et al., *DNA Cell Biol.*, 9:713-723, 1990.
Herz and Gerard, *Proc. Natl. Acad. Sci. USA*, 90:2812-2816, 1993.
Hirochika et al., *J. Virol.*, 61:2599, 1987.
Hirsch et al., *Mol. Cell. Biol.*, 10:1959, 1990.
Holbrook et al., *Virology*, 157:211, 1987.
Horlick and Benfield, *Mol. Cell. Biol.*, 9:2396, 1989.
Horwich et al. *J. Virol.*, 64:642-650, 1990.
Huang et al., *Cell*, 27:245, 1981.
Hug et al., *Mol. Cell. Biol.*, 8:3065, 1988.
Hutvagner et al., *PLoS Biol.*, 2(4):E98, 2004.
Hwang et al., *Mol. Cell. Biol.*, 10:585, 1990.
Imagawa et al., *Cell*, 51:251, 1987.
Imbra and Karin, *Nature*, 323:555, 1986.
Imler et al., *Mol. Cell. Biol.*, 7:2558, 1987.
Imperiale and Nevins, *Mol. Cell. Biol.*, 4:875, 1984.
Ito and Roeder, *Trends Endocrinol. Metab.*, 12:127-134, 2001.
Jakobovits et al., *Mol. Cell. Biol.*, 8:2555, 1988.
Jameel and Siddiqui, *Mol. Cell. Biol.*, 6:710, 1986.
Jaynes et al., *Mol. Cell. Biol.*, 8:62, 1988.
Ji et al., *Mol. Cell. Biol.* 27(4):1531-43, 2006.
Johnson et al., *Mol. Cell. Biol.*, 9:3393, 1989.
Jones and Shenk, *Cell*, 13:181-188, 1978.
Kadesch and Berg, *Mol. Cell. Biol.*, 6:2593, 1986.
Kaneda et al., *Science*, 243:375-378, 1989.
Karin et al., *Mol. Cell. Biol.*, 7:606, 1987.
Karin et al., *Mol. Cell. Biol.*, 7:606, 1987.
Karlsson et al., *EMBO J.*, 5:2377-2385, 1986.
Katinka et al., *Cell*, 20:393, 1980.
Katinka et al., *Nature*, 290:720, 1981.
Kato et al, *J. Biol. Chem.*, 266:3361-3364, 1991.
Kawamoto et al., *Mol. Cell. Biol.*, 8:267, 1988.
Kelly et al., *J. Cell Biol.*, 129(2):383-396, 1995.
Kiledjian et al., *Mol. Cell. Biol.*, 8:145, 1988.
Kimura et al., *Dev. Growth Differ.* 39(3):257-265, 1997.
Kiriazis and Kranias, *Annu. Rev. Physiol.*, 62:321-351, 2000.
Klamut et al., *Mol. Cell. Biol.*, 10:193, 1990.
Klein et al., *Nature*, 327:70-73, 1987.
Koch et al., *Mol. Cell. Biol.*, 9:303, 1989.
Krek et al., *Nature Genetics*, 37:495-500, 2005.
Krenz and Robbins, *J. Am. Coll. Cardiol.*, 44:2390-2397, 2004.
Kriegler and Botchan, In: *Eukaryotic Viral Vectors*, Gluzman (Ed.), Cold Spring Harbor: Cold Spring Harbor Laboratory, NY, 1982.
Kriegler and Botchan, *Mol. Cell. Biol.*, 3:325, 1983a.
Kriegler et al., *Cell*, 38:483, 1984.
Kriegler et al., *Cell*, 53:45, 1988.
Kriegler et al., In: *Gene Expression*, Alan Liss (Ed.), Hamer and Rosenberg, New York, 1983b.
Krützfeldt et al., *Nature*, 438:685-689, 2005.
Kuhl et al., *Cell*, 50:1057, 1987.
Kunz et al., *Nucl. Acids Res.*, 17:1121, 1989.
Lagos-Quintana et al., *Science*, 294(5543):853-858, 2001.
LaPointe et al., *Hypertension* 27(3 Pt 2):715-22, 1996.
LaPointe et al., *J. Biol. Chem.*, 263(19):9075-8, 1988.
Larsen et al., *Proc Natl. Acad. Sci. USA*, 83:8283, 1986.
Laspia et al., *Cell*, 59:283, 1989.
Latimer et al., *Mol. Cell. Biol.*, 10:760, 1990.
Lau et al., *Science*, 294(5543):858-862, 2001.
Le Gal La Salle et al., *Science*, 259:988-990, 1993.
Lee and Ambros, *Science*, 294(5543):862-864, 2001.
Lee et al., *Nature*, 294:228, 1981.
Lee et al., *Nucleic Acids Res.*, 12:4191-206, 1984.
Leung et al., *Proc. Natl. Acad. Sci. USA*, 48:18125-18130, 2006.
Levinson et al., *Nature*, 295:79, 1982.
Levrero et al., *Gene*, 101:195-202, 1991.
Lin et al., *Mol. Cell. Biol.*, 10:850, 1990.
Lowes et al., *J. Clin. Invest.*, 100:2315-2324, 1997.
Luria et al., *EMBO J.*, 6:3307, 1987.
Lusky and Botchan, *Proc. Natl. Acad. Sci. USA*, 83:3609, 1986.
Lusky et al., *Mol. Cell. Biol.*, 3:1108, 1983.
Macejak and Sarnow, *Nature*, 353:90-94, 1991.
Majors and Varmus, *Proc. Natl. Acad. Sci. USA*, 80:5866, 1983.
Mann et al., *Cell*, 33:153-159, 1983.
Markowitz et al., *J. Virol.*, 62:1120-1124, 1988.
McKinsey and Olson, *J. Clin. Invest.*, 115:538-546, 2005.
McNeall et al., *Gene*, 76:81, 1989.
Meister and Tuschl, *Nature*, 431:343-9, 2004.
Miksicek et al., *Cell*, 46:203, 1986.
Miyata et al., *Circ. Res.*, 86:386-390, 2000.
Mordacq and Linzer, *Genes and Dev.*, 3:760, 1989.
Moreau et al., *Nucl. Acids Res.*, 9:6047, 1981.
Morkin, *Microsc. Res. Tech.*, 50:522-531, 2000.
Moss et al., *Biol. Chem.*, 271(49):31688-31694, 1996.
Muesing et al., *Cell*, 48:691, 1987.
Nakao et al., *J. Clin. Invest.*, 100:2362-2370, 1997.
Naya et al., *J Biol Chem*, 275(7):4545-4548, 2000.
Ng et al., *Nuc. Acids Res.*, 17:601, 1989.
Nicolas and Rubinstein, In: *Vectors: A survey of molecular cloning vectors and their uses*, Rodriguez and Denhardt (Eds), Stoneham: Butterworth, 494-513, 1988.

Nicolau and Sene, *Biochim. Biophys. Acta*, 721:185-190, 1982.
Nicolau et al., *Methods Enzymol.*, 149:157-176, 1987.
Ondek et al., *EMBO J.*, 6:1017, 1987.
Ornitz et al., *Mol. Cell. Biol.*, 7:3466, 1987.
Palmiter et al., *Nature*, 300:611, 1982.
Pantos et al., *Horm. Metab. Res.*, 38:308-313, 2006.
Paskind et al., *Virology*, 67:242-248, 1975.
Pasquinelli and Ruvkun, *Ann. Rev. Cell Dev. Biol.*, 18:495-513, 2002.
PCT Appln. WO 0071096
PCT Appln. WO 98/33791
Pech et al., *Mol. Cell. Biol.*, 9:396, 1989.
Pelletier and Sonenberg, *Nature*, 334(6180):320-325, 1988.
Perales et al., *Proc. Natl. Acad. Sci. USA*, 91:4086-4090, 1994.
Perez-Stable and Constantini, *Mol. Cell. Biol.*, 10:1116, 1990.
Physicians Desk Reference
Picard and Schaffner, *Nature*, 307:83, 1984.
Pinkert et al., *Genes and Dev.*, 1:268, 1987.
Ponta et al., *Proc. Natl. Acad. Sci. USA*, 82:1020, 1985.
Porton et al., *Mol. Cell. Biol.*, 10:1076, 1990.
Potter et al., *Proc. Natl. Acad. Sci. USA*, 81:7161-7165, 1984.
Queen and Baltimore, *Cell*, 35:741, 1983.
Quinn et al., *Mol. Cell. Biol.*, 9:4713, 1989.
Racher et al., *Biotechnology Techniques*, 9:169-174, 1995.
Ragot et al., *Nature*, 361:647-650, 1993.
Redondo et al., *Science*, 247:1225, 1990.
Reisman and Rotter, *Mol. Cell. Biol.*, 9:3571, 1989.
Remington's Pharmaceutical Sciences, 15th ed., pages 1035-1038 and 1570-1580, Mack Publishing Company, Easton, Pa., 1980.
Renan, *Radiother. Oncol.*, 19:197-218, 1990.
Resendez Jr. et al., *Mol. Cell. Biol.*, 8:4579, 1988.
Rich et al., *Hum. Gene Ther.*, 4:461-476, 1993.
Ridgeway, In: *Vectors: A Survey of Molecular Cloning Vectors and Their Uses*, Rodriguez et al. (Eds.), Stoneham: Butterworth, 467-492, 1988.
Ripe et al., *Mol. Cell. Biol.*, 9:2224, 1989.
Rippe, et al., *Mol. Cell. Biol.*, 10:689-695, 1990.
Rittling et al., *Nuc. Acids Res.*, 17:1619, 1989.
Rosen et al., *Cell*, 41:813, 1988.
Rosenfeld et al., *Science*, 252:431-434, 1991.
Rosenfeld, et al., *Cell*, 68:143-155, 1992.
Roux et al., *Proc. Natl. Acad. Sci. USA*, 86:9079-9083, 1989.
Sakai et al., *Genes and Dev.*, 2:1144, 1988.
Sambrook and Russell, Molecular Cloning: A Laboratory Manual 3rd Ed., Cold Spring Harbor Laboratory Press, 2001.
Satake et al., *J. Virology*, 62:970, 1988.
Schaffner et al., *J. Mol. Biol.*, 201:81, 1988.
Searle et al., *Mol. Cell. Biol.*, 5:1480, 1985.
Sharp and Marciniak, *Cell*, 59:229, 1989.
Shaul and Ben-Levy, *EMBO J.*, 6:1913, 1987.
Sherman et al., *Mol. Cell. Biol.*, 9:50, 1989.
Sleigh and Lockett, *J. EMBO*, 4:3831, 1985.
Spalholz et al., *Cell*, 42:183, 1985.
Spandau and Lee, *J. Virology*, 62:427, 1988.
Spandidos and Wilkie, *EMBO J.*, 2:1193, 1983.
Stephens and Hentschel, *Biochem. J.*, 248:1, 1987.
Stratford-Perricaudet and Perricaudet, In: *Human Gene Transfer*, Eds, Cohen-Haguenauer and Boiron, John Libbey Eurotext, France, 51-61, 1991.
Stratford-Perricaudet et al., *Hum. Gene. Ther.*, 1:241-256, 1990.
Stuart et al., *Nature*, 317:828, 1985.
Sullivan and Peterlin, *Mol. Cell. Biol.*, 7:3315, 1987.
Swartzendruber and Lehman, *J. Cell. Physiology*, 85:179, 1975.
Takebe et al., *Mol. Cell. Biol.*, 8:466, 1988.
Tang et al., *Muscle Nerve*, 36(3), 342-8, 2007.
Tavernier et al., *Nature*, 301:634, 1983.
Taylor and Kingston, *Mol. Cell. Biol.*, 10:165, 1990a.
Taylor and Kingston, *Mol. Cell. Biol.*, 10:176, 1990b.
Taylor et al., *J. Biol. Chem.*, 264:15160, 1989.
Temin, In: *Gene Transfer*, Kucherlapati (Ed.), NY, Plenum Press, 149-188, 1986.
The Merck Index, Eleventh Edition
Thiesen et al., *J. Virology*, 62:614, 1988.
Top et al., *J. Infect. Dis.*, 124:155-160, 1971.
Treisman, *Cell*, 46(4):567-174, 1986
Tronche et al., *Mol. Biol. Med.*, 7:173, 1990.
Tronche et al., *Mol. Cell. Biol.*, 9(11):4759-4766, 1989.
Trudel and Constantini, *Genes and Dev.*, 6:954, 1987.
Tsika et al., *Am. J. Physiol. Cell Physiol.*, 283:C1761-C1775, 2002.
Tur-Kaspa et al., *Mol. Cell. Biol.*, 6:716-718, 1986.
Tyndell et al., *Nuc. Acids. Res.*, 9:6231, 1981.
van Rooij et al., *Proc. Natl. Acad. Sci. USA*, 103(48):18255-18260, 2006.
van Rooij et al. *Science* 316(5824):575-9. 2007.
Vannice and Levinson, *J. Virology*, 62:1305, 1988.
Varmus et al., *Cell*, 25:23-36, 1981.
Vasseur et al., *Proc Natl. Acad. Sci. USA*, 77:1068, 1980.
Wagner et al., *Proc. Natl. Acad. Sci. USA* 87(9):3410-3414, 1990.
Wang and Calame, *Cell*, 47:241, 1986.
Weber et al., *Cell*, 36:983, 1984.
Wei et al., *J. Endocrinol. Invest.*, 28:8-11, 2005.
Weinberger et al. *Mol. Cell. Biol.*, 8:988, 1984.
Winoto and Baltimore, *Cell*, 59:649, 1989.
Wong et al., *Gene*, 10:87-94, 1980.
Wu and Wu, *Adv. Drug Delivery Rev.*, 12:159-167, 1993.
Wu and Wu, *Biochemistry*, 27: 887-892, 1988.
Wu and Wu, *J. Biol. Chem.*, 262:4429-4432, 1987.
Xu et al., *Curr. Biol.*, 13:790-795, 2003.
Yamauchi-Takihara, et. al., *Proc. Natl. Acad. Sci. USA*, 86(10):3504-3508, 1989.
Yang and Russell, *Proc. Natl. Acad. Sci. USA*, 87:4144-4148, 1990.
Yao and Eghbali, *Circ. Res.*, 71:831-839, 1992.
Young et al., In: *Handbook of Applied Therapeutics*, 7.1-7.12 and 9.1-9.10, 1989.
Yutzey et al. *Mol. Cell. Biol.*, 9:1397, 1989.
Zelenin et al., *FEBS Lett.*, 287(1-2):118-120, 1991.
Zeng et al., *Mol. Cell.*, 9(6):1327-33, 2002.
Zhao et al., *Nature*, 436:214-220, 2005.
Ziober and Kramer, *J. Bio. Chem.*, 271(37):22915-22, 1996.

The invention claimed is:

1. A method for treating pathologic cardiac hypertrophy, heart failure, or myocardial infarction in a subject in need thereof comprising administering to the subject:

a miR-499 inhibitor, wherein the miR-499 inhibitor is an antisense oligonucleotide comprising a sequence that is at least 85% complementary to a miR-499 sequence over the entire length of the antisense oligonucleotide; and a miR-208/miR-208b inhibitor, wherein the miR-208/miR-208b inhibitor is an antisense oligonucleotide comprising a sequence that is at least 85% complementary to a miR-208 or miR-208b sequence over the entire length of the antisense oligonucleotide, wherein the expression or activity of miR-499 and miR-208 or miR-208b is inhibited in the heart cells of the subject following administration of the miR-499 inhibitor and the miR-208/miR-208b inhibitor.

2. The method of claim 1, wherein the miR-499 inhibitor is an antisense oligonucleotide comprising a sequence that is at least 95% complementary to SEQ ID NO: 26 over the entire length of the antisense oligonucleotide.

3. The method of claim 1, wherein the miR-499 inhibitor is an antisense oligonucleotide comprising a sequence that is 100% complementary to SEQ ID NO: 26 over the entire length of the antisense oligonucleotide.

4. The method of claim 1, wherein the miR-208/miR-208b inhibitor is an antisense oligonucleotide comprising a sequence that is at least 95% complementary to SEQ ID NO: 5 or SEQ ID NO: 27 over the entire length of the antisense oligonucleotide.

5. The method of claim 1, wherein the miR-208/miR-208b inhibitor is an antisense oligonucleotide comprising a sequence that is 100% complementary to SEQ ID NO: 5 or SEQ ID NO: 27 over the entire length of the antisense oligonucleotide.

6. The method of claim 1, wherein the miR-208/miR-208b inhibitor is an antisense oligonucleotide comprising a sequence that is at least 95% complementary to a pre-miR-208 sequence over the entire length of the antisense oligonucleotide.

7. The method of claim 6, wherein the pre-miR-208 sequence is SEQ ID NO: 14, SEQ ID NO: 15, SEQ ID NO: 16, or SEQ ID NO: 17.

8. The method of claim 1, wherein the miR-208/miR-208b inhibitor is an antisense oligonucleotide comprising a sequence that is at least 95% complementary to a pre-miR-208b sequence.

9. The method of claim 8, wherein the pre-miR-208b sequence is SEQ ID NO: 30, SEQ ID NO: 31, SEQ ID NO: 32, SEQ ID NO: 33, SEQ ID NO: 34, SEQ ID NO: 35, or SEQ ID NO: 36.

10. The method of claim 1, wherein the miR-499 inhibitor is an antisense oligonucleotide comprising a sequence that is at least 95% complementary to a pre-miR-499 sequence.

11. The method of claim 10, wherein the pre-miR-499 sequence is SEQ ID NO: 18, SEQ ID NO: 19, SEQ ID NO: 20, SEQ ID NO: 21, SEQ ID NO: 22, SEQ ID NO: 23, or SEQ ID NO: 24.

12. The method of claim 1, wherein the miR-499 inhibitor and/or the miR-208/miR-208b inhibitor is about 15 to about 50 nucleotides in length.

13. The method of claim 1, wherein the miR-499 inhibitor and/or the miR-208/miR-208b inhibitor is about 19 to about 25 nucleotides in length.

14. The method of claim 1, wherein the miR-499 inhibitor and/or the miR-208/miR-208b inhibitor comprises at least one chemical modification.

15. The method of claim 14, wherein the chemical modification is a sugar and/or backbone modification.

16. The method of claim 15, wherein the sugar modification is a modification selected from the group consisting of 2'-O-alkyl, 2'-O-methyl, 2'-O-methoxyethyl, 2'-fluoro, and a locked nucleic acid.

17. The method of claim 15, wherein the backbone modification is a phosphorothioate linkage.

18. The method of claim 1, wherein the miR-499 inhibitor and/or the miR-208/miR-208b inhibitor is conjugated to cholesterol.

19. The method of claim 1, wherein the miR-499 inhibitor and/or the miR-208/miR-208b inhibitor is administered by intradermal, subcutaneous, intramuscular, intraperitoneal, intravenous, oral, transdermal, sustained release, controlled release, delayed release, suppository, catheter, or sublingual administration or direct injection into cardiac tissue.

20. A method of preventing pathologic cardiac hypertrophy or heart failure in a subject identified as being at risk of developing pathologic cardiac hypertrophy or heart failure comprising:

administering to the subject a miR-499 inhibitor, wherein the miR-499 inhibitor is an antisense oligonucleotide comprising a sequence that is at least 85% complementary to a miR-499 sequence over the entire length of the antisense oligonucleotide; and administering to the subject a miR-208/miR-208b inhibitor, wherein the miR-208/miR-208b inhibitor is an antisense oligonucleotide comprising a sequence that is at least 85% complementary to a miR-208 or miR-208b sequence over the entire length of the antisense oligonucleotide, wherein the expression or activity of miR-499 and miR-208 or miR-208b is inhibited in the heart cells of the subject following administration of the miR-499 inhibitor and the miR-208/miR-208b inhibitor.

21. The method of claim 20, wherein the subject identified as being at risk exhibits one or more risk factors selected from the group consisting of long standing uncontrolled hypertension, uncorrected valvular disease, chronic angina, recent myocardial infarction, or congenital predisposition to heart disease.

22. The method of claim 20, wherein the subject identified as being at risk has been diagnosed as having a genetic predisposition to cardiac hypertrophy.

23. The method of claim 20, wherein the subject identified as being at risk has a familial history of cardiac hypertrophy.

24. The method of claim 20, wherein the miR-499 inhibitor is an antisense oligonucleotide comprising a sequence that is at least 95% complementary to SEQ ID NO: 26 over the entire length of the antisense oligonucleotide.

25. The method of claim 20, wherein the miR-499 inhibitor is an antisense oligonucleotide comprising a sequence that is 100% complementary to SEQ ID NO: 26 over the entire length of the antisense oligonucleotide.

26. The method of claim 20, wherein the miR-208/miR-208b inhibitor is an antisense oligonucleotide comprising a sequence that is at least 95% complementary to SEQ ID NO: 5 or SEQ ID NO: 27 over the entire length of the antisense oligonucleotide.

27. The method of claim 20, wherein the miR-208/miR-208b inhibitor is an antisense oligonucleotide comprising a sequence that is 100% complementary to SEQ ID NO: 5 or SEQ ID NO: 27 over the entire length of the antisense oligonucleotide.

28. The method of claim 20, wherein the miR-208/miR-208b inhibitor is an antisense oligonucleotide comprising a sequence that is at least 95% complementary to a pre-miR-208 sequence over the entire length of the antisense oligonucleotide.

29. The method of claim 28, wherein the pre-miR-208 sequence is SEQ ID NO: 14, SEQ ID NO: 15, SEQ ID NO: 16, or SEQ ID NO: 17.

30. The method of claim 20, wherein the miR-208/miR-208b inhibitor is an antisense oligonucleotide comprising a sequence that is at least 95% complementary to a pre-miR-208b sequence over the entire length of the antisense oligonucleotide.

31. The method of claim 30, wherein the pre-miR-208b sequence is SEQ ID NO: 30, SEQ ID NO: 31, SEQ ID NO: 32, SEQ ID NO: 33, SEQ ID NO: 34, SEQ ID NO: 35, or SEQ ID NO: 36.

32. The method of claim 20, wherein the miR-499 inhibitor is an antisense oligonucleotide comprising a sequence that is at least 95% complementary to a pre-miR-499 sequence over the entire length of the antisense oligonucleotide.

33. The method of claim 32, wherein the pre-miR-499 sequence is SEQ ID NO: 18, SEQ ID NO: 19, SEQ ID NO: 20, SEQ ID NO: 21, SEQ ID NO: 22, SEQ ID NO: 23, or SEQ ID NO: 24.

34. The method of claim 20, wherein the miR-499 inhibitor and/or the miR-208/miR-208b inhibitor is about 15 to about 50 nucleotides in length.

35. The method of claim 20, wherein the miR-499 inhibitor and/or the miR-208/miR-208b inhibitor is about 19 to about 25 nucleotides in length.

36. The method of claim 20, wherein the miR-499inhibitor and/or the miR-208b /miR-208b inhibitor comprises at least one chemical modification.

37. The method of claim 36, wherein the chemical modification is a sugar and/or backbone modification.

38. The method of claim 37, wherein the sugar modification is a modification selected from the group consisting of 2'-O-alkyl, 2'-O-methyl, 2'-O-methoxyethyl, 2'-fluoro, and a locked nucleic acid.

39. The method of claim 37, wherein the backbone modification is a phosphorothioate linkage.

40. The method of claim 20, wherein the miR-499 inhibitor and/or the miR-208/miR-208b inhibitor is conjugated to cholesterol.

41. The method of claim 20, wherein the miR-499 inhibitor and/or the miR-208/miR-208b inhibitor is administered by intradermal, subcutaneous, intramuscular, intraperitoneal, intravenous, oral, transdermal, sustained release, controlled release, delayed release, suppository, catheter, or sublingual administration or direct injection into cardiac tissue.

\* \* \* \* \*

SEQUENCE LISTING

<160> NUMBER OF SEQ ID NOS: 39

<210> SEQ ID NO 1

```
<211> LENGTH: 71
<212> TYPE: DNA
<213> ORGANISM: Homo sapiens

<400> SEQUENCE: 1
tgacgggcga gcttttggcc cgggttatac ctgatgctca cgtataagac gagcaaaaag    60
cttgttggtc a                                                         71

<210> SEQ ID NO 2
<211> LENGTH: 71
<212> TYPE: DNA
<213> ORGANISM: Mus sp.

<400> SEQUENCE: 2
tgacgggtga gcttttggcc cgggttatac ctgactctca cgtataagac gagcaaaaag    60
cttgttggtc a                                                         71

<210> SEQ ID NO 3
<211> LENGTH: 71
<212> TYPE: DNA
<213> ORGANISM: Rattus sp.

<400> SEQUENCE: 3
tgacgggtga gcttttggcc cgggttatac ctgactctca cgtataagac gagcaaaaag    60
cttgttggtc a                                                         71

<210> SEQ ID NO 4
<211> LENGTH: 71
<212> TYPE: DNA
<213> ORGANISM: Canis sp.

<400> SEQUENCE: 4
tgacgcatga gcttttggct cgggttatac ctgatgctca cgtataagac gagcaaaaag    60
cttgttggtc a                                                         71

<210> SEQ ID NO 5
<211> LENGTH: 22
<212> TYPE: RNA
<213> ORGANISM: Unknown
<220> FEATURE:
<223> OTHER INFORMATION: Mature miR-208 sequence

<400> SEQUENCE: 5
auaagacgag caaaaagcuu gu                                             22

<210> SEQ ID NO 6
<211> LENGTH: 69
<212> TYPE: RNA
<213> ORGANISM: Homo sapiens

<400> SEQUENCE: 6
uucuugcuuu aaagcaauug gucuaaaaua uauguaaucg ucuuaauuaa aaaguugcag    60
uagguuugc                                                            69

<210> SEQ ID NO 7
<211> LENGTH: 69
<212> TYPE: RNA
<213> ORGANISM: Pan sp.

<400> SEQUENCE: 7
uucuugcuuu aaagcaauug gucuaaaaua uauguaaucg ucuuaauuaa aacguugcag    60
```

```
                                          uaggguugc                                               69

<210> SEQ ID NO 8
<211> LENGTH: 69
<212> TYPE: RNA
<213> ORGANISM: Mus sp.

<400> SEQUENCE: 8
uucuugcuuu aaagcaauug gucuaaaaua uauguaaucg ucuuaauuaa aagcuugcag       60
uaggguugc                                                             69

<210> SEQ ID NO 9
<211> LENGTH: 69
<212> TYPE: RNA
<213> ORGANISM: Rattus sp.

<400> SEQUENCE: 9
uucuugcuuu aaagcaauug gucuaaaaua uauguaaucg ucuuaauuaa aacguugcag       60
uaggguugc                                                             69

<210> SEQ ID NO 10
<211> LENGTH: 69
<212> TYPE: RNA
<213> ORGANISM: Canis sp.

<400> SEQUENCE: 10
uucuugcuuu aaagcaauug gucuaaaaua uauguaaucg ucuuaauuaa aacguugcag       60
uaggguugc                                                             69

<210> SEQ ID NO 11
<211> LENGTH: 69
<212> TYPE: RNA
<213> ORGANISM: Gallus sp.

<400> SEQUENCE: 11
uucuugcuuu aaagcaauug gucuaaaaua uauguaaucg ucuuaauuaa aacguugcag       60
uaggguugc                                                             69

<210> SEQ ID NO 12
<211> LENGTH: 72
<212> TYPE: RNA
<213> ORGANISM: Takifugu

<400> SEQUENCE: 12
uuccugcuuu aagcaauugg uugaaaauau auguauguaa uggucuuaau uaaaaaaaca       60
aacuaagaca aa                                                         72

<210> SEQ ID NO 13
<211> LENGTH: 69
<212> TYPE: RNA
<213> ORGANISM: Danio sp.

<400> SEQUENCE: 13
uuccugcuuu aaagcaauug gucuaaaaua uauguaaucg ucuucauuac aaaaacgaac       60
caucaaacg                                                             69

<210> SEQ ID NO 14
<211> LENGTH: 71
<212> TYPE: DNA
```

<213> ORGANISM: Homo sapiens

<400> SEQUENCE: 14
acgggcgagc ttttggcccg ggttatacct gatgctcacg tataagacga gcaaaaagct    60
tgttggtcag a                                                         71

<210> SEQ ID NO 15
<211> LENGTH: 71
<212> TYPE: DNA
<213> ORGANISM: Mus sp.

<400> SEQUENCE: 15
acgggtgagc ttttggcccg ggttatacct gactctcacg tataagacga gcaaaaagct    60
tgttggtcag a                                                         71

<210> SEQ ID NO 16
<211> LENGTH: 71
<212> TYPE: DNA
<213> ORGANISM: Rattus sp.

<400> SEQUENCE: 16
acgggtgagc ttttggcccg ggttatacct gactctcacg tataagacga gcaaaaagct    60
tgttggtcag a                                                         71

<210> SEQ ID NO 17
<211> LENGTH: 71
<212> TYPE: DNA
<213> ORGANISM: Canis sp.

<400> SEQUENCE: 17
acgcatgagc ttttggctcg ggttatacct gatgctcacg tataagacga gcaaaaagct    60
tgttggtcag a                                                         71

<210> SEQ ID NO 18
<211> LENGTH: 76
<212> TYPE: DNA
<213> ORGANISM: Mus sp.

<400> SEQUENCE: 18
tccctgtgtc ttgggtgggc agctgttaag acttgcagtg atgtttagct cctctgcatg    60
tgaacatcac agcaag                                                    76

<210> SEQ ID NO 19
<211> LENGTH: 74
<212> TYPE: DNA
<213> ORGANISM: Rattus sp.

<400> SEQUENCE: 19
tccctgtctt gggtgggcag ctgttaagac ttgcagtgat gtttagctcc tctccatgtg    60
aacatcacag caag                                                      74

<210> SEQ ID NO 20
<211> LENGTH: 76
<212> TYPE: DNA
<213> ORGANISM: Homo sapiens

<400> SEQUENCE: 20
cccctgtgcc ttgggcgggc ggctgttaag acttgcagtg atgtttaact cctctccacg    60
tgaacatcac agcaag                                                    76

<210> SEQ ID NO 21
<211> LENGTH: 76
<212> TYPE: DNA
<213> ORGANISM: Canis sp.

<400> SEQUENCE: 21
cccttgcacc ctgggcgggc ggccgttaag acttgcagtg atgtttaact cctctccacg    60
tgaacatcac agcaag                                                    76

<210> SEQ ID NO 22
<211> LENGTH: 76
<212> TYPE: DNA
<213> ORGANISM: Monodelphis sp.

<400> SEQUENCE: 22
cccctgcctc cccggcgggc agctgttaag acttgcagtg atgtttaatt cttctctatg    60
tgaacatcac aacaag                                                    76

<210> SEQ ID NO 23
<211> LENGTH: 62
<212> TYPE: DNA
<213> ORGANISM: Gallus sp.

<400> SEQUENCE: 23
ggagcggcag ttaagacttg tagtgatgtt tagataatgt attacatgga catcacttta    60
ag                                                                    62

<210> SEQ ID NO 24
<211> LENGTH: 68
<212> TYPE: DNA
<213> ORGANISM: Xenopus tropicalis

<400> SEQUENCE: 24
gtcttagcga ggcagttaag acttgcagtg atgtttagtt aaaatctttt catgaacatc    60
actttaag                                                              68

<210> SEQ ID NO 25
<211> LENGTH: 79
<212> TYPE: RNA
<213> ORGANISM: Unknown
<220> FEATURE:
<223> OTHER INFORMATION: Pre-miR-499 sequence

<400> SEQUENCE: 25
gggugggcag cuguuaagac uugcagugau guuuagcucc ucugcaugug aacaucacag    60
caagucugug cugcugccu                                                  79

<210> SEQ ID NO 26
<211> LENGTH: 21
<212> TYPE: RNA
<213> ORGANISM: Unknown
<220> FEATURE:
<223> OTHER INFORMATION: miR-499 sequence

<400> SEQUENCE: 26
uuaagacuug cagugauguu u                                               21

<210> SEQ ID NO 27
<211> LENGTH: 22
<212> TYPE: RNA

```
<213> ORGANISM: Unknown
<220> FEATURE:
<223> OTHER INFORMATION: miR-208b sequence

<400> SEQUENCE: 27
auaagacgaa caaaagguuu gu                                              22

<210> SEQ ID NO 28
<211> LENGTH: 17
<212> TYPE: DNA
<213> ORGANISM: Unknown
<220> FEATURE:
<223> OTHER INFORMATION: U6 forward primer

<400> SEQUENCE: 28
gtgctcgctt cggcagc                                                    17

<210> SEQ ID NO 29
<211> LENGTH: 28
<212> TYPE: DNA
<213> ORGANISM: Unknown
<220> FEATURE:
<223> OTHER INFORMATION: U6 reverse primer

<400> SEQUENCE: 29
aaaatatgga acgcttcacg aatttgcg                                        28

<210> SEQ ID NO 30
<211> LENGTH: 43
<212> TYPE: DNA
<213> ORGANISM: Homo sapiens

<400> SEQUENCE: 30
tttctgatcc gaatataaga cgaacaaaag gtttgtctga ggg                       43

<210> SEQ ID NO 31
<211> LENGTH: 43
<212> TYPE: DNA
<213> ORGANISM: Mus sp.

<400> SEQUENCE: 31
tttctgatcc gaatataaga cgaacaaaag gtttgtctga ggg                       43

<210> SEQ ID NO 32
<211> LENGTH: 43
<212> TYPE: DNA
<213> ORGANISM: Rattus sp.

<400> SEQUENCE: 32
tttctgatcc gaatataaga cgaacaaaag gtttgtctga ggg                       43

<210> SEQ ID NO 33
<211> LENGTH: 43
<212> TYPE: DNA
<213> ORGANISM: Canis sp.

<400> SEQUENCE: 33
tttctgatcc gaatataaga cgaacaaaag gtttgtctga ggg                       43

<210> SEQ ID NO 34
<211> LENGTH: 43
<212> TYPE: DNA
<213> ORGANISM: Monodelphis sp.

<400> SEQUENCE: 34
```

```
tttttggatct gaatataaga cgaacaaaag gtttgtctgt gtg          43

<210> SEQ ID NO 35
<211> LENGTH: 43
<212> TYPE: DNA
<213> ORGANISM: Xenopus tropicalis

<400> SEQUENCE: 35
ttttctgttg ttgtataaga cgagcataaa gcttgtttgt tag          43

<210> SEQ ID NO 36
<211> LENGTH: 77
<212> TYPE: RNA
<213> ORGANISM: Unknown
<220> FEATURE:
<223> OTHER INFORMATION: Pre miR-208b sequence

<400> SEQUENCE: 36
ccucucaggg aagcuuuuug cucgcguuau guuucucauc cgaauauaag acgaacaaaa     60
gguuugucug agggcug                                                   77

<210> SEQ ID NO 37
<211> LENGTH: 71
<212> TYPE: RNA
<213> ORGANISM: Unknown
<220> FEATURE:
<223> OTHER INFORMATION: Pre miR-208 sequence

<400> SEQUENCE: 37
ugacgggcga gcuuuuggcc cggguuauac cugaugcuca cguauaagac gagcaaaaag     60
cuuguugguc a                                                         71

<210> SEQ ID NO 38
<211> LENGTH: 24
<212> TYPE: RNA
<213> ORGANISM: Unknown
<220> FEATURE:
<223> OTHER INFORMATION: miR-208 sequence

<400> SEQUENCE: 38
auaagacgag caaaaagcuu guuu                                            24

<210> SEQ ID NO 39
<211> LENGTH: 23
<212> TYPE: RNA
<213> ORGANISM: Unknown
<220> FEATURE:
<223> OTHER INFORMATION: miR-499 sequence

<400> SEQUENCE: 39
uuaagacuug cagugauguu uaa                                             23
```